United States Patent
Starkebaum et al.

(10) Patent No.: US 9,937,344 B2
(45) Date of Patent: Apr. 10, 2018

(54) WAVEFORMS FOR ELECTRICAL STIMULATION THERAPY

(75) Inventors: Warren L. Starkebaum, Plymouth, MN (US); Roland C. Maude-Griffin, Edina, MN (US); Elizabeth D. Firestone, St. Paul, MN (US); Carl A. Schu, Plymouth, MN (US); Orhan Soykan, Shoreview, MN (US)

(73) Assignee: Medtronic, Inc., Minneapolis, MN (US)

(*) Notice: Subject to any disclaimer, the term of this patent is extended or adjusted under 35 U.S.C. 154(b) by 975 days.

(21) Appl. No.: 12/887,149

(22) Filed: Sep. 21, 2010

(65) Prior Publication Data

US 2011/0071589 A1 Mar. 24, 2011

Related U.S. Application Data

(60) Provisional application No. 61/244,431, filed on Sep. 21, 2009.

(51) Int. Cl.
*A61N 1/36* (2006.01)

(52) U.S. Cl.
CPC ...... *A61N 1/36007* (2013.01); *A61N 1/36085* (2013.01); *A61N 1/36171* (2013.01); *A61N 1/36175* (2013.01)

(58) Field of Classification Search
CPC ............... A61N 1/0507; A61N 1/0509; A61N 1/36007; A61N 1/36167; A61N 1/36175; A61N 1/36178

(Continued)

(56) References Cited

U.S. PATENT DOCUMENTS

| 2,865,376 A | 12/1958 | Pellier et al. |
| 3,563,247 A * | 2/1971 | Bowers ............... 607/13 |

(Continued)

FOREIGN PATENT DOCUMENTS

| CN | 1956749 A | 5/2007 |
| DE | 44 02 058 | 4/1995 |

(Continued)

OTHER PUBLICATIONS

Notification of Transmittal of the International Search Report and the Written Opinion of the International Searching Authority for corresponding patent application No. PCT/US2010/049676, dated Jan. 10, 2011, 9 pages.

(Continued)

*Primary Examiner* — Eugene T Wu
(74) *Attorney, Agent, or Firm* — Shumaker & Sieffert, P.A.

(57) ABSTRACT

In some examples, the disclosure relates to a systems, devices, and techniques for delivering electrical stimulation therapy to a patient. In one example, the disclosure relates to a method including delivering a series of pulses with alternating pulse polarities to a gastrointestinal tract of a patient. The series of pulses includes at least a first pulse of a first polarity, a second pulse of a second polarity, and a third pulse of the first polarity, where the first, second and third pulses are delivered in direct succession and in that order. The first and second pulses are separated by a first time delay and the second and third pulses are separated by a second time delay. In some examples, each of the first and second time delays depend on the frequency that the series of pulses are delivered.

47 Claims, 22 Drawing Sheets

(58) Field of Classification Search
USPC .................................... 607/40, 72, 74, 133
See application file for complete search history.

(56) References Cited

U.S. PATENT DOCUMENTS

| | | | |
|---|---|---|---|
| 3,589,370 A * | 6/1971 | McDonald | 607/70 |
| 3,760,812 A | 9/1973 | Timm et al. | |
| 3,946,745 A * | 3/1976 | Hsiang-Lai et al. | 607/74 |
| 4,444,207 A | 4/1984 | Robicsek | |
| 4,475,560 A | 10/1984 | Tarjan et al. | |
| 4,524,771 A | 6/1985 | McGregor et al. | |
| 4,612,934 A | 9/1986 | Borkan | |
| 4,813,418 A * | 3/1989 | Harris | 607/156 |
| 4,901,722 A | 2/1990 | Noguchi | |
| 5,059,207 A | 10/1991 | Shah | |
| 5,063,929 A | 11/1991 | Bartelt et al. | |
| 5,100,431 A | 3/1992 | Buster et al. | |
| 5,109,847 A | 5/1992 | Liss et al. | |
| 5,188,104 A | 2/1993 | Wernicke et al. | |
| 5,217,471 A | 6/1993 | Burkhart | |
| 5,242,458 A | 9/1993 | Bendel et al. | |
| 5,263,480 A | 11/1993 | Wernicke et al. | |
| 5,292,344 A | 3/1994 | Douglas | |
| 5,350,414 A | 9/1994 | Kolen | |
| 5,423,872 A | 6/1995 | Cigaina | |
| 5,423,876 A | 6/1995 | Camps et al. | |
| 5,433,728 A | 7/1995 | Kim | |
| 5,450,739 A | 9/1995 | Bogart et al. | |
| 5,484,404 A | 1/1996 | Schulman et al. | |
| 5,489,294 A | 2/1996 | McVenes et al. | |
| 5,512,057 A | 4/1996 | Reiss et al. | |
| 5,540,730 A | 7/1996 | Terry, Jr. et al. | |
| 5,562,717 A * | 10/1996 | Tippey et al. | 607/41 |
| 5,690,691 A * | 11/1997 | Chen et al. | 607/40 |
| 5,716,392 A | 2/1998 | Bourgeois et al. | |
| 5,776,170 A | 7/1998 | MacDonald et al. | |
| 5,836,994 A | 11/1998 | Bourgeois | |
| 5,861,014 A | 1/1999 | Familoni | |
| 5,995,872 A | 11/1999 | Bourgeois | |
| 6,041,258 A | 3/2000 | Cigaina et al. | |
| 6,083,249 A * | 7/2000 | Familoni | 607/40 |
| 6,091,992 A | 7/2000 | Bourgeois et al. | |
| 6,097,984 A | 8/2000 | Douglas | |
| 6,098,672 A | 8/2000 | Kiholm | |
| 6,104,955 A | 8/2000 | Bourgeois | |
| 6,115,635 A | 9/2000 | Bourgeois | |
| 6,146,391 A | 11/2000 | Cigaina | |
| 6,026,326 A | 12/2000 | Bardy | |
| 6,216,039 B1 | 4/2001 | Bourgeois | |
| 6,233,488 B1 | 5/2001 | Hess | |
| 6,238,423 B1 | 5/2001 | Bardy | |
| 6,243,607 B1 | 6/2001 | Mintchev et al. | |
| 6,321,124 B1 | 11/2001 | Cigaina | |
| 6,327,503 B1 | 12/2001 | Familoni | |
| 6,449,511 B1 | 9/2002 | Mintchev et al. | |
| 6,453,199 B1 | 9/2002 | Kobozev | |
| 6,510,332 B1 | 1/2003 | Greenstein | |
| 6,542,776 B1 | 4/2003 | Gordon et al. | |
| 6,564,101 B1 | 5/2003 | Zikria | |
| 6,571,127 B1 | 5/2003 | Ben-Haim et al. | |
| 6,591,137 B1 | 7/2003 | Fischell et al. | |
| 6,600,953 B2 | 7/2003 | Flesler et al. | |
| 6,606,523 B1 | 8/2003 | Jenkins | |
| 6,615,084 B1 | 9/2003 | Cigaina | |
| 6,678,561 B2 | 1/2004 | Forsell | |
| 6,684,104 B2 | 1/2004 | Gordon et al. | |
| 6,745,078 B1 * | 6/2004 | Buchner | 607/72 |
| 6,895,278 B1 | 5/2005 | Gordon | |
| 6,990,376 B2 * | 1/2006 | Tanagho et al. | 607/40 |
| 6,993,391 B2 | 1/2006 | Flesler et al. | |
| 7,006,871 B1 | 2/2006 | Darvish et al. | |
| 7,065,403 B1 | 6/2006 | Mouchawar et al. | |
| 7,120,497 B2 | 10/2006 | Ben-Haim et al. | |
| 7,177,693 B2 | 2/2007 | Starkebaum | |
| 7,221,978 B2 | 5/2007 | Ben-Haim et al. | |
| 7,330,753 B2 | 2/2008 | Policker et al. | |
| 7,359,751 B1 * | 4/2008 | Erickson et al. | 607/27 |
| 7,483,748 B2 * | 1/2009 | Torgerson et al. | 607/46 |
| 7,502,649 B2 | 3/2009 | Ben-Haim et al. | |
| 7,512,442 B2 | 3/2009 | Flesler et al. | |
| 7,765,008 B2 | 7/2010 | Ben-Haim et al. | |
| 7,937,158 B2 * | 5/2011 | Erickson et al. | 607/59 |
| 8,180,445 B1 * | 5/2012 | Moffitt | 607/2 |
| 2002/0072780 A1 | 6/2002 | Foley | |
| 2002/0099412 A1 | 7/2002 | Fischell et al. | |
| 2002/0161414 A1 | 10/2002 | Flesler et al. | |
| 2002/0165589 A1 | 11/2002 | Imran et al. | |
| 2002/0198470 A1 | 12/2002 | Imran et al. | |
| 2003/0009202 A1 | 1/2003 | Levine | |
| 2003/0018367 A1 | 1/2003 | DiLorenzo | |
| 2003/0054463 A1 | 3/2003 | Baker et al. | |
| 2003/0055464 A1 | 3/2003 | Darvish et al. | |
| 2003/0144708 A1 | 7/2003 | Starkebaum | |
| 2003/0195581 A1 | 10/2003 | Meadows et al. | |
| 2003/0236558 A1 | 12/2003 | Whitehurst et al. | |
| 2004/0049240 A1 | 3/2004 | Gerber et al. | |
| 2004/0088022 A1 | 5/2004 | Chen | |
| 2004/0088023 A1 | 5/2004 | Imran et al. | |
| 2004/0162595 A1 | 8/2004 | Foley | |
| 2004/0193229 A1 | 9/2004 | Starkebaum et al. | |
| 2004/0236381 A1 | 11/2004 | Dinsmoor et al. | |
| 2004/0236382 A1 | 11/2004 | Dinsmoor et al. | |
| 2004/0267333 A1 | 12/2004 | Kronberg | |
| 2005/0021101 A1 | 1/2005 | Chen et al. | |
| 2005/0033375 A1 * | 2/2005 | Marchal et al. | 607/40 |
| 2005/0131486 A1 | 6/2005 | Boveja et al. | |
| 2005/0137643 A1 | 6/2005 | Mintchev | |
| 2005/0149141 A1 | 7/2005 | Starkebaum | |
| 2005/0149142 A1 * | 7/2005 | Starkebaum | 607/40 |
| 2005/0209653 A1 | 9/2005 | Herbert et al. | |
| 2005/0222637 A1 | 10/2005 | Chen | |
| 2005/0222638 A1 | 10/2005 | Foley et al. | |
| 2005/0240239 A1 | 10/2005 | Boveja et al. | |
| 2005/0245957 A1 | 11/2005 | Starkebaum et al. | |
| 2006/0058856 A1 | 3/2006 | Morrell | |
| 2006/0085045 A1 | 4/2006 | Harel et al. | |
| 2006/0167498 A1 | 7/2006 | DiLorenzo | |
| 2006/0184207 A1 | 8/2006 | Darvish et al. | |
| 2006/0212086 A1 * | 9/2006 | Mintchev et al. | 607/40 |
| 2006/0247717 A1 | 11/2006 | Starkebaum | |
| 2006/0247718 A1 * | 11/2006 | Starkebaum | 607/40 |
| 2006/0257445 A1 | 11/2006 | Tropsha et al. | |
| 2006/0257446 A1 | 11/2006 | Tropsha et al. | |
| 2007/0027493 A1 | 2/2007 | Ben-Haim et al. | |
| 2007/0060812 A1 | 3/2007 | Harel et al. | |
| 2007/0078494 A1 | 4/2007 | Mintchev | |
| 2007/0104754 A1 | 5/2007 | Sterling et al. | |
| 2007/0104755 A1 | 5/2007 | Sterling et al. | |
| 2007/0150021 A1 | 6/2007 | Chen et al. | |
| 2007/0162084 A1 | 7/2007 | Chen et al. | |
| 2007/0162085 A1 * | 7/2007 | DiLorenzo | 607/40 |
| 2007/0255154 A1 | 11/2007 | Lu et al. | |
| 2007/0282387 A1 * | 12/2007 | Starkebaum | 607/40 |
| 2007/0299320 A1 | 12/2007 | Policker et al. | |
| 2007/0299482 A1 * | 12/2007 | Littlewood et al. | 607/46 |
| 2008/0058871 A1 | 3/2008 | Libbus et al. | |
| 2008/0178684 A1 | 7/2008 | Spehr | |
| 2008/0281368 A1 * | 11/2008 | Bulkes et al. | 607/4 |
| 2008/0281375 A1 * | 11/2008 | Chen | 607/40 |
| 2008/0300656 A1 * | 12/2008 | Donders et al. | 607/60 |
| 2009/0076561 A1 * | 3/2009 | Libbus et al. | 607/11 |
| 2009/0088817 A1 * | 4/2009 | Starkebaum et al. | 607/40 |
| 2009/0118797 A1 | 5/2009 | Kliger et al. | |
| 2009/0132010 A1 | 5/2009 | Kronberg | |
| 2009/0157149 A1 | 6/2009 | Wahlgren et al. | |
| 2009/0204063 A1 | 8/2009 | Policker et al. | |
| 2009/0240294 A1 * | 9/2009 | Forsell | 607/3 |
| 2009/0264951 A1 * | 10/2009 | Sharma | 607/40 |
| 2009/0281449 A1 | 11/2009 | Thrower et al. | |
| 2010/0152817 A1 | 6/2010 | Gillbe | |
| 2010/0228105 A1 | 9/2010 | Policker et al. | |
| 2010/0228313 A1 * | 9/2010 | Starkebaum et al. | 607/40 |
| 2010/0331916 A1 * | 12/2010 | Parramon et al. | 607/60 |

(56) References Cited

U.S. PATENT DOCUMENTS

FOREIGN PATENT DOCUMENTS

| WO | 97/41921 | 11/1997 |
|---|---|---|
| WO | 02/087657 | 11/2002 |
| WO | 03066154 A2 | 8/2003 |
| WO | 2004007018 A1 | 1/2004 |
| WO | 2008121891 A1 | 10/2008 |
| WO | 2009/045294 A1 | 4/2009 |
| WO | 2009/097542 A2 | 8/2009 |

OTHER PUBLICATIONS

Office Action from U.S. Appl. No. 11/804,312, dated Dec. 19, 2011, 6 pp.
Response to Office Action dated Dec. 19, 2011, from U.S. Appl. No. 11/804,312, filed Feb. 21, 2012, 5 pp.
Notice of Allowance from U.S. Appl. No. 11/804,312, dated Mar. 13, 2012, 8 pp.
Office action for U.S. Appl. No. 11/804,312, dated Mar. 9, 2010, 9 pages.
Response to office action for U.S. Appl. No. 11/804,312, filed Jun. 9, 2011, 12 pages.
H. Abrahamsson, "Vagal Relaxation of the Stomach Induced from the Gastric Antrum", Acta physiol. scand. 1973, 89, pp. 406-414.
Final office action for U.S. Appl. No. 11/804,312, dated Jul. 29, 2011, 7 pages.
Pre-Appeal Brief Request for Review for U.S. Appl. No. 11/804,312, filed Oct. 31, 2011, 3 pages.
"DDW 2006 Rules for Abstract Submission", Digestive Disease Week 2006, Los Angeles Convention Center, May 20-25, 2006, 3 pages.
Carlyon et al., "Effect of inter-phase gap on the sensitivity of cochlear implant users to electrical stimulation," Hearing Research 205 (2005), 210-224.
Chen et al., "Electrical Pacing Accelerates Intestinal Transit Slowed by Fat-Induced Ileal Brake", Digestive Diseases and Sciences, vol. 48, No. 2, Feb. 2003, pp. 251-256.
Chen et al., "Gastric Electrical Stimulation for Obesity: is there a need for a new generation device?", VA Research Foundation, Oklahoma City, OK, USA, 1 page, submitted for Digestive Disease Week 2006, Los Angeles Convention Center, May 20-25, 2006, (see also "DDW 2006 Rules for Abstract Submission", Digestive Disease Week 2006, Los Angeles Convention Center, May 20-25, 2006, 3 pages.).
Chen, "Gastric Electrical Stimulation With Short Pulses Reduces Vomiting but not Dysrhythmias in Dogs," Gastroenterology 2003;124:401-409.
Chen et al., "Gastric electrical stimulation reduces visceral sensitivity in healthy canines," abstract presented at International Electrogastrography Society, 2005, 1 pg.
Cigaina, "Implantable Gastric Stimulation for the Treatment of Morbid Obesity", Transneuronix, Inc., Revision 1, Oct. 3, 1999, 12 pages.
Cigaina, "Implantable Gastric Stimulation for the Treatment of Morbid Obesity", Transneuronix, Inc., Revision 2, Nov. 1, 1999, 11 pages.
Dickens et al., "Identification of rhythmically active cells in guinea-pig stomach," Journal of Physiology, vol. 514, No. 2, pp. 515-531 (Jan. 1999).
Eddington et al., "Speech Processors for Auditory Prostheses," NIH Contract NO1-DC-2-1001, Final Progress Report, Jan. 1, 2002-Jun. 30, 2005, 14 pp.
Endo et al., "An obese rat model of bariatric surgery with gastric banding," Obes Surg. 2007 17(6):815-9.
Huizinga, "Gastrointestinal Peristalsis: Joint Action of Enteric Nerves, Smooth Muscle, and Interstitial Cells of Cajal," Microscopy Research and Technique, vol. 47, No. 4, pp. 239-247 (Dec. 1999).

Kampe et al., "A rodent model of adjustable gastric band surgery-implications for the understanding of underlying mechanisms," Obes Surg 2009 19(5):625-31.
Kanno et al., "Rat gastric banding model for bariatric surgery," J Nippon Med Sch. 2008 75(4):202-6.
Lei et al., "Effects and Mechanisms of Implantable Gastric Stimulation on Gastric Distention in Conscious Dogs," Obesity Surgery, vol. 15, pp. 528-533, 2005.
Lei et al., "Gastric electrical stimulation induced gastric distention in obese rats," BIOSIS/BIOSIS, XP-002579955, Apr. 28, 2010, 2 pages.
Lei et al., "The effect of short-pulse gastric electrical stimulation (Enterra Therapy) on gastric tone varies with the sites and parameters of stimulation", Transneuronix Inc and Veterans Research Foundation, Oklahoma City, OK, May 2005, 1 page.
Lei et al., "Effects of dual pulse gastric electrical stimulation on gastric tone and compliance in dogs," Digestive and Liver Disease, 2008, Dig Liver Dis (2008), doi:10.1016/j.dld.2008.07.312.
Lei et al., "Effects of dual pulses gastric electrical stimulation on gastric tone and compliance," abstract presented at International Electrogastrography Society, 2005, 1 pg.
Lin et al., "Electrical Stimulation of the Small Intestine in Dogs", Proceedings—19$^{th}$ International Conference—IEEE/EMBS, Oct. 30-Nov. 2, 1997, Chicago, IL., 4 pages.
Liu et al., "Therapeutic potentials of a novel mthod of dual-pulse gastric electrdical stimulation for gastric dysrhythmia and symptoms of nausea and vomiting," The American Journal of Surgery 191 (2006): 255-261.
Luo et al., "Effects and Mechanisms of Gastric Electrical Stimulation on Gastric Tone in Rats", VA Research Foundation, Oklahoma City, OK, USA, 1 page, submitted for Digestive Disease Week 2006, Los Angeles Convention Center, May 20-25, 2006, (see also "DDW 2006 Rules for Abstract Submission", Digestive Disease Week 2006, Los Angeles Convention Center, May 20-25, 2006, 3 pages.).
Macherey et al., "Asymmetric Pulses in Cochlear Implants: Effects of Pulse Shape, Polarity, and Rate," JARO 7: 255-266 (2006), pp. 253-266.
McIntyre et al., "Extracellular Stimulation of Central Neurons: Influence of Stimulus Waveform and Frequency on Neuronal Output," J Neurophysiol 88: 1592-1604, 2002.
Miller et al., "Electrically evoked single-fiber action potentials from cat: responses to monopolar, monophasic stimulation," Hearing Research 130 (1999), 197-218.
Monteiro et al., "A rat model of restrictive bariatric surgery with gastric banding," Obes Surg 2006 16(1):48-51.
Monteiro et al., "Increase in ghrelin levels after weight loss in obese Zucker rats is prevented by gastric banding," Obes Surg. 2007 17(12):1599-607.
Monteiro et al., "Rats submitted to gastric banding are leaner and show distinctive feeding patterns," Obes Surg. 2006 16(5):597-602.
Ouyang et al., "Gastric or intestinal electrical stimulation-induced increase in gastric volume is correlated with reduced food intake," Scandinavian Journal of Gastroenterology, vol. 41, pp. 1261-1266, 2006.
Ouyang et al., "Gastrointestinal Electrical Stimulation-Induced Increase in Gastric volume is Correlated with Reduced Food Intake", Transneuronix and Veterans Research & Education Foundation, Oklahoma City, OK, Mar. 2, 2006, 23 pages.
Personalized Itinerary Planner and Abstract Book, DDW, May 20-25, 2006, 127 pages.
Qi et al., "Dual pulse intestinal electrical stimulation normalizes intestinal dysrhythmia and improves symptoms induced by vasopressin in fed state in dogs," Neurogastroenterol Motil (2007) 19: 411-418.
Qi et al., "Normalization of intestinal dysrhythmia and improvement of symptoms with a novel method of dual pulse intestinal electrical stimulation in dogs," abstract presented at International Electrogastrography Society, 2005, 1 pg.
Rubinstein et al., "Analysis of Monophasic Biphasic Electrical Stimulation of Nerve," IEEE Transactions on Biomedical Engineering, vol. 48, No. 10, Oct. 2001, pp. 1065-1070.

(56) References Cited

OTHER PUBLICATIONS

Shepherd et al., "Chronic Electrical Stimulation of the Auditory Nerve using Non-charge-balanced Stimuli," Acta Otolayngol (Stockh) 1999;119:674-684.
Shepherd et al., "Electrical stimulation of the auditory nerve: II. Effect of stimulus waveshape on single fibre response properties," Hearing Research 130 (1999): 171-188.
Song et al., "A novel method of 2-channel dual-pulse gastric electrical stimulation improves solid gastric emptying in dogs," Surgery 2008;143:72-8.
Song et al., "Effects of dual pulse gastric electrical stimulation on vasopressin-induced dysmotility in dogs," abstract presented at International Electrogastrography Society, 2005, 1 pg.
Stylopoulos et al., "Roux-en-Y gastric bypass enhances energy expenditure and extends lifespan in diet-induced obese rats," *Obesity*, 2009 17(10):1839-47.
Sun et al. "Intestinal Electric Stimulation Decreases Fat Absorption in Rats: Therapeutic Potential for Obesity," Obesity Research, vol. 12, No. 8 (Aug. 2004), pp. 1235-1242.
Thirteenth International Workshop on Electrogastrography, Meeting-at-a-Glance, The Feinberg Pavilion, Northwestern University Medical Center, Chicago, Illinois, May 18-19, 2005, 58 pages.
Van Wieringen, "Effects of waveform shape on human sensitivity to electrical stimulation of the inner ear," Hearing Research 200 (2005), pp. 73-86.
Vantrappen et al., "Gastrointestinal Motility Disorders," Digestive Diseases and Sciences, vol. 31, No. 9, pp. 5S-25S, (Sep. 1986 Supplement).
Zhang et al., "Central neuronal mechanisms of GES and effects of stimulation parameters and locations in regular and diet-induced obese rats," BIOSIS/BIOSIS, XP-002579956, Apr. 28, 2010, 2 pages.
Office Action from U.S. Appl. No. 13/445,718 dated Aug. 20, 2013, 8 pp.
Response to Office Action dated Aug. 20, 2013 from U.S. Appl. No. 13/445,718, filed Dec. 20, 2013, 9 pp.
Examination Report No. 1 for Australian patent application No. 2010295275, dated Aug. 15, 2012, 4 pages.
Office action for patent U.S. Appl. No. 12/715,993, dated Oct. 5, 2012, 9 pages.
Response to Office Action dated Oct. 5, 2012, from U.S. Appl. No. 12/715,993, filed Jan. 7, 2013, 9 pages.
Final Office action for U.S. Appl. No. 12/715,993, dated Jan. 31, 2013, 10 pages.
Response to Final Office Action dated Jan. 31, 2013, from U.S. Appl. No. 12/715,993, filed Mar. 29, 2013, 8 pages.
Notice of Allowance dated May 16, 2013, from U.S. Appl. No. 12/715,993, 9 pages.
Examination report from corresponding European Patent Application No. 10 757 921.1-2305, dated Jan. 11, 2013, 5 pages.
Office action for U.S. Appl. No. 13/355,122, dated Jan. 16, 2013, 17 pages.
Response to Office Action dated Jan. 16, 2013, from U.S. Appl. No. 13/355,122, filed May 16, 2013, 9 pages.
Response to Final Office Action dated Jul. 9, 2013, from U.S. Appl. No. 13/355,122, filed Oct. 9, 2013, 12 pages.
U.S. Appl. No. 14/026,854, by Warren L. Starkebaum, filed Sep. 13, 2013.
Office Action from corresponding Japanese Patent Application No. 2012-529976, dated May 27, 2013, 6 pages.
Office action from U.S. Appl. No. 13/355,122, dated Jul. 9, 2013, 15 pp.
Office Action U.S. Appl. No. 13/355,122, dated Dec. 24, 2013, 15 pp.
Office Action from U.S. Appl. No. 14/026,854, dated Feb. 3, 2014, 9 pp.
Final Office Action from U.S. Appl. No. 13/355,122, dated Jun. 4, 2014, 15 pp.
Japanese Decision of Rejection from counterpart Japanese Application No. 2012-529976, dated Feb. 28, 2014, 4 pp.
Chinese Office Action from Chinese Application No. 20108003872.8, dated Jan. 23, 2014, 10 pp.
Response to Office Action dated Dec. 24, 2013, from U.S. Appl. No. 13/355,122, filed Mar. 21, 2014, 11 pp.
Pre-Appeal Brief Request for Review for U.S. Appl. No. 13/355,122, dated Sep. 4, 2014, 5 pp.
Notice of Appeal for U.S. Appl. No. 13/355,122, dated Sep. 4, 2014, 1 pp.
Second Office Action from Counterpart Chinese Application No. 201080033872.8, dated Sep. 2, 2014, 26 pp.

* cited by examiner

WAVEFORMS FOR ELECTRICAL STIMULATION THERAPY

This application claims the benefit of U.S. Provisional Application No. 61/244,431 by Starkebaum et al., entitled, "WAVEFORMS FOR ELECTRICAL STIMULATION THERAPY" and filed on Sep. 21, 2009, the entire content of which is incorporated herein by reference.

TECHNICAL FIELD

The disclosure relates to medical devices and, more particularly, medical devices for delivery of electrical stimulation therapy.

BACKGROUND

Obesity is a serious health problem for many people. Patients who are overweight often have problems with mobility, sleep, high blood pressure, and high cholesterol. Some other serious risks also include diabetes, cardiac arrest, stroke, kidney failure, and mortality. In addition, an obese patient may experience psychological problems associated with health concerns, social anxiety, and generally poor quality of life.

Certain diseases or conditions can contribute to additional weight gain in the form of fat, or adipose tissue. However, healthy people may also become overweight as a net result of excess energy consumption and insufficient energy expenditure. Reversal of obesity is possible but difficult. Once the patient expends more energy than is consumed, the body will begin to use the energy stored in the adipose tissue. This process will slowly remove the excess fat from the patient and lead to better health. Some patients require intervention to help them overcome their obesity. In these severe cases, nutritional supplements, prescription drugs, or intense diet and exercise programs may not be effective.

Surgical intervention is a last resort treatment for some obese patients who are considered morbidly obese. One common surgical technique is the Roux-en-Y gastric bypass surgery. In this technique, the surgeon staples or sutures off a large section of the stomach to leave a small pouch that holds food. Next, the surgeon severs the small intestine a point between the distal and proximal sections, and attaches the distal section of the small intestine to the pouch portion of the stomach. This procedure limits the amount of food the patient can ingest to a few ounces and limits the amount of time that ingested food may be absorbed through the shorter length of the small intestine. While this surgical technique may be very effective, it poses significant risks of unwanted side effects, including malnutrition, and death.

Electrical stimulation therapy is an alternative to surgical intervention and may be effective in treating obesity either alone or in combination with diet, exercise and/or other therapies (e.g., drugs, biologics, devices). For electrical stimulation therapy, a patient may be fitted with an implanted electrical stimulator that delivers electrical stimulation pulses to the patient's stomach via electrodes carried by one or more leads. The electrical stimulation therapy may be configured to induce a sensation of fullness or nausea in the patient, thereby discouraging excessive food intake. Alternatively or additionally, the electrical stimulation therapy may be configured to increase or decrease gastric motility, reduce appetite or increase satiety, or induce a sensation of abdominal discomfort on ingestion of a meal, which may result in reduced caloric absorption and/or reduced caloric intake. Hence, electrical stimulation therapy may be effective in causing weight loss by discouraging food intake and/or reducing caloric absorption.

SUMMARY

The disclosure is directed to medical devices, systems, and techniques for delivery of electrical stimulation therapy to treat one or more patient conditions. A medical device may deliver electrical stimulation therapy, which includes a series of electrical stimulation pulses, via one or more electrodes to one or more tissue sites of a patient. The series of electrical stimulation pulses may be delivered to the one or more tissues sites in a manner that effectively treats the patient condition. In some examples, the medical device may be configured to generate and deliver electrical stimulation therapy, e.g., gastric electrical stimulation, to a patient using one or more example waveforms described in this disclosure.

In one aspect, the disclosure is related to a method comprising delivering a series of pulses with alternating pulse polarities to a gastrointestinal tract of a patient, wherein the series of pulses includes at least a first pulse of a first polarity, a second pulse of a second polarity, and a third pulse of the first polarity, wherein the first, second and third pulses are delivered in succession, and wherein the first and second pulses are separated by a first time delay and the second and third pulses are separated by a second time delay.

In another aspect, the disclosure is related to a device comprising a stimulation generator configured to generate and deliver a series of pulses having alternating pulse polarities to a patient; and a processor configured to control the series of pulses generated and delivered by the stimulation generator, wherein the series of pulses includes at least a first pulse of a first polarity, a second pulse of a second polarity, and a third pulse of the first polarity, wherein the first, second and third pulses are delivered in direct succession, in that order, wherein the first and second pulses are separated by a first time delay and the second and third pulses are separated by a second time delay, and wherein the device is configured to deliver the series of pulses to a gastrointestinal tract of the patient.

In another aspect, the disclosure is related to a device comprising means for delivering a series of pulses with alternating pulse polarities to a gastrointestinal tract of a patient, wherein the series of pulses includes at least a first pulse of a first polarity, a second pulse of a second polarity, and a third pulse of the first polarity, wherein the first, second and third pulses are delivered in succession, and wherein the first and second pulses are separated by a first time delay and the second and third pulses are separated by a second time delay.

In another aspect, the disclosure relates to a method comprising delivering a series of pulses with alternating pulse polarities to a patient, wherein the series of pulses includes at least a first pulse of a first polarity, a second pulse of a second polarity, and a third pulse of the first polarity, wherein the first, second and third pulses are delivered in direct succession, in that order, wherein the first and second pulses are separated by a first time delay and the second and third pulses are separated by a second time delay, and wherein the series of pulses are delivered at frequency between approximately 0.05 Hz and 40 Hz.

In another aspect, the disclosure relates to a medical device system comprising a stimulation generator configured to generate and deliver a series of pulses having alternating pulse polarities to a patient; and a processor configured to control the series of pulses generated and delivered by the stimulation generator, wherein the series of pulses includes at least a first pulse of a first polarity, a second pulse of a second polarity, and a third pulse of the first polarity, wherein the first, second and third pulses are delivered in direct succession, in that order, wherein the first and second pulses are separated by a first time delay and the second and third pulses are separated by a second time delay, and wherein the series of pulses are delivered at frequency between approximately 0.05 Hz and 40 Hz.

In another aspect, the disclosure relates to a medical device system comprising means for delivering a series of pulses with alternating pulse polarities to a patient, wherein the series of pulses includes at least a first pulse of a first polarity, a second pulse of a second polarity, and a third pulse of the first polarity, wherein the first, second and third pulses are delivered in direct succession, in that order, wherein the first and second pulses are separated by a first time delay and the second and third pulses are separated by a second time delay, and wherein the series of pulses are delivered at frequency between approximately 0.05 Hz and 40 Hz.

In another aspect, the disclosure relates to a method comprising delivering a series of pulses with alternating pulse polarities to a patient, wherein the series of pulses includes at least a first pulse of a first polarity, a second pulse of a second polarity, and a third pulse of the first polarity, wherein the first, second and third pulses are delivered in direct succession, in that order, wherein the first and second pulses are separated by a first time delay and the second and third pulses are separated by a second time delay, and wherein the series of pulses are delivered with a controlled current.

In another aspect, the disclosure relates to a medical device system comprising a stimulation generator configured to generate and deliver a series of pulses having alternating pulse polarities to a patient; and a processor configured to control the series of pulses generated and delivered by the stimulation generator, wherein the series of pulses includes at least a first pulse of a first polarity, a second pulse of a second polarity, and a third pulse of the first polarity, wherein the first, second and third pulses are delivered in direct succession, in that order, wherein the first and second pulses are separated by a first time delay and the second and third pulses are separated by a second time delay, and wherein the series of pulses are delivered with a controlled current.

In another aspect, the disclosure relates to a medical device system comprising means for delivering a series of pulses with alternating pulse polarities to a patient, wherein the series of pulses includes at least a first pulse of a first polarity, a second pulse of a second polarity, and a third pulse of the first polarity, wherein the first, second and third pulses are delivered in direct succession, in that order, wherein the first and second pulses are separated by a first time delay and the second and third pulses are separated by a second time delay, and wherein the series of pulses are delivered with a controlled current.

In another aspect, the disclosure is directed to a computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein. The computer-readable storage medium may be an article of manufacture, and may be non-transitory.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1:
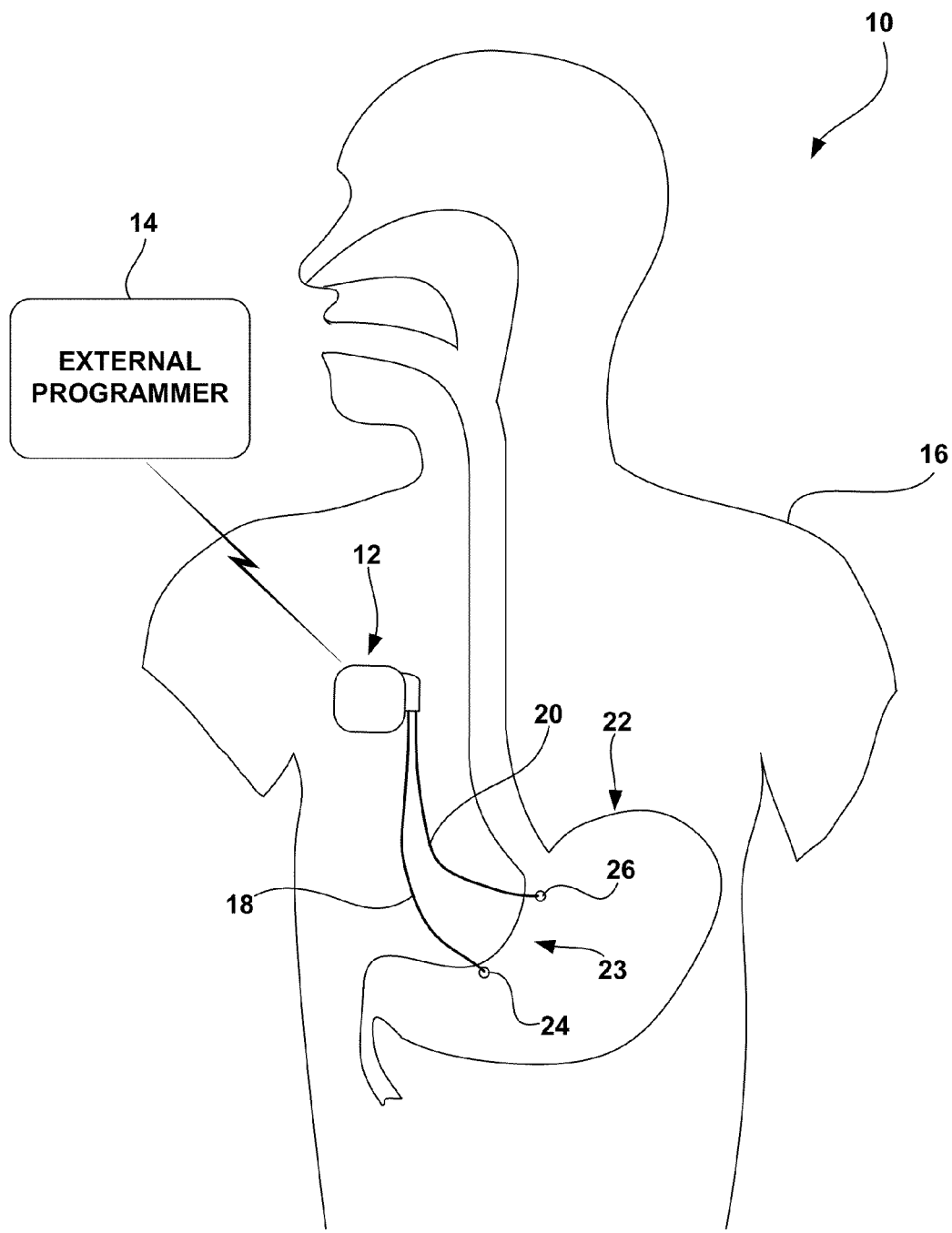
FIG. 1 is a schematic diagram illustrating an example implantable gastric electrical stimulation system.

The disclosure is directed to medical devices, systems, and techniques for delivery of electrical stimulation therapy to treat one or more patient conditions. A medical device may deliver electrical stimulation therapy including a series of electrical stimulation pulses via one or more electrodes to one or more tissue sites of patient. The series of electrical stimulation pulses may be delivered to the one or more tissues sites in a manner that effectively treats the patient condition. Example waveforms are described which represent example series of electrical stimulation pulses that may be delivered to a patient for electrical stimulation therapy.

In some examples, a medical device may generate and deliver gastric electrical stimulation therapy to one or more tissue sites of the gastrointestinal (GI) tract to treat a disorder of the GI tract. Gastric electrical stimulation generally refers to electrical stimulation areas of the gastrointestinal tract including the esophagus (including lower and upper esophageal sphincters), stomach (including pylorus), duodenum, small bowel, large bowel, and anal sphincter. Gastric electrical stimulation may be alternatively referred to as gastrointestinal electrical stimulation. A medical device system for providing gastric electrical stimulation to a patient may include an implantable medical device (IMD) that generates and delivers electrical stimulation pulses or signals to GI tract tissue site(s) via one or more electrodes carried on one or more implantable leads. In some examples, the electrical stimulation may be generated by an external stimulator such as an external trial stimulator. An external stimulator may deliver stimulation to the desired GI tract tissue sites via one or more electrodes carried on one or more percutaneously implantable leads. In other examples, the electrical stimulator may be a leadless electrical stimulator.

Gastric electrical stimulation therapy may be delivered to the gastrointestinal tract, e.g., the stomach and/or small intestine, to treat a disease or disorder such as obesity or gastroparesis. In the case of obesity therapy, for example, electrical stimulation of the stomach may be configured to cause the stomach to undergo a change in gastric muscle tone, which may be indicated by distention, and induce a feeling of satiety within the patient. As a result, the patient may reduce caloric intake because the patient has a reduced urge to eat. Alternatively, or additionally, electrical stimulation of the stomach may be configured to induce nausea in the patient and thereby discourage eating. In addition, electrical stimulation of the duodenum may be configured to increase motility in the small intestine, thereby reducing caloric absorption and/or altering the dynamics of nutrient absorption in ways the promote earlier satiation, thereby reducing caloric intake. In some examples, gastric electrical stimulation therapy may be delivered to the gastrointestinal tract to treat diabetes. For example, the reduction in caloric intake described above may help treat or manage diabetes, such as, e.g., in the case of Type II Diabetes. In addition, gastric stimulation of the stomach and/or duodenum may be configured to delay gastric emptying, slowing the delivery of nutrients into the small intestine following meals, thereby reducing the occurrence of episodes of post-meal hyperglycemia in Type II Diabetic patients or pre-Diabetic patients with impaired glycemic control. In the case of gastroparesis, gastric stimulation of the stomach and/or duodenum may be configured to increase or regulate motility. Alternatively or additionally, gastric stimulation may result in changes in neural signaling and/or hormonal secretion/signaling that may result in improved glycemia, possibly via changes in insulin secretion and/or sensitivity. In some examples, gastric stimulation of the stomach and/or duodenum may be configured to normalize motility (e.g., by increasing the rate of gastric emptying when a patient has delayed gastric emptying, or retarding the rate of gastric emptying when a patient has rapid gastric emptying).

The effectiveness of the gastric electrical stimulation therapy in treating a patient disease or disorder can depend on one or more properties of the electrical stimulation energy generated and delivered from a gastric stimulator to the patient. For example, values for pulse width, pulse frequency, constant voltage or constant current amplitude, and electrode polarity (anode or cathode) may be defined for a series of electrical stimulation pulses delivered to a patient to treat a disorder or disease, in addition to microduty and/or macroduty cycles for the stimulation therapy. The relationship between each of these parameter values may be expressed as a waveform, e.g., the waveform defined by the series of electrical stimulation pulses plotted in terms of amplitude (controlled current or controlled voltage) versus time. In some examples, the delivery of gastric electrical stimulation therapy in a manner consistent with one or more particular electrical stimulation waveforms may be utilized to effectively treat one or more patient disease or disorders using electrical stimulation therapy.

In some examples, a gastric stimulator may deliver electrical stimulation therapy to a patient such that the electrical stimulation energy is charge balanced. As used herein, charge balance may generally refer to the property of the net charge of one or more stimulation pulses being approximately equal to zero. For example, when a pair of single phase pulses having opposite polarity are substantially charged balanced, the charge of the first pulse substantially offsets the charge of the second pulse such that the net charge of the pulses is substantially zero. Graphically, in terms of two pulses having opposite polarity, charge balance implies that the area between the amplitude curve and the zero amplitude line for a first pulse having a first polarity is equal to the area between the amplitude curve and the zero amplitude line for the second pulse having the opposite polarity. In general, charge balance may be desirable for limiting electrochemical reactions on the surface of the stimulation electrodes that can cause corrosion of the electrodes, formation of noxious compounds at the stimulation site, and transfer of electrode material into the surrounding tissue.

Figure 6A:
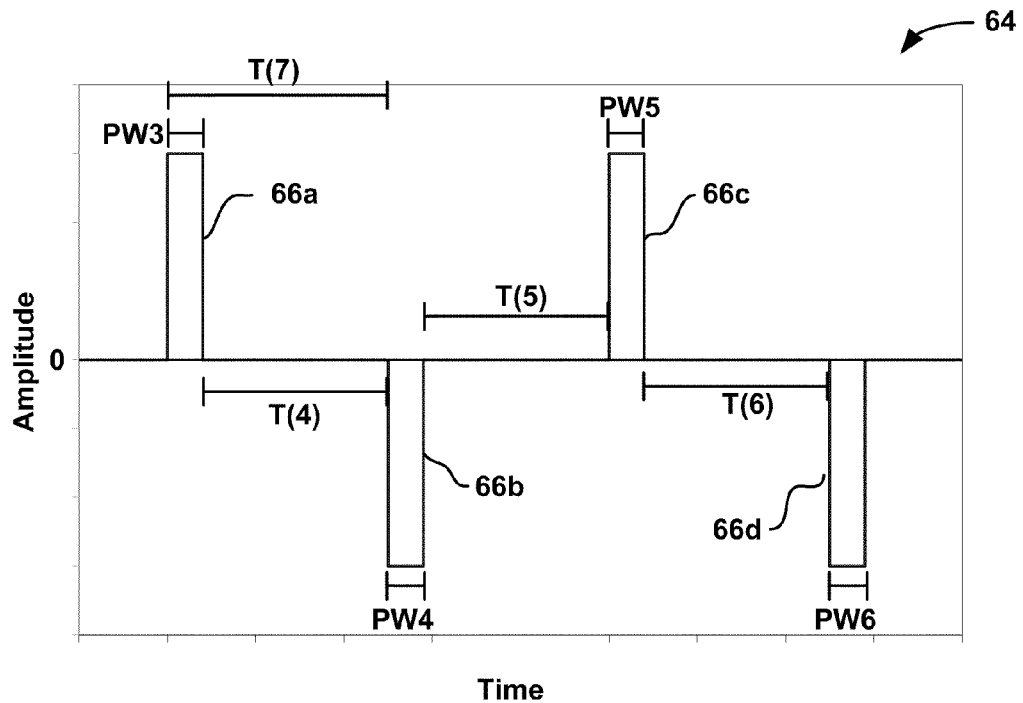
FIG. 6A is a plot illustrating another example waveform representing an example series of electrical stimulation for delivery to a patient.

As will be described in greater detail below, one example electrical stimulation waveform that may be utilized for gastric electrical stimulation may include monophasic rectangular pulses with alternating pulse polarities. Such a waveform may also be referred to as "alternating monophasic pulses waveform" or "alternating monophasic waveform." An example of an alternating monophasic waveform is shown in FIG. 6A. In an alternating monophasic waveform, each pulse has a single stimulus phase of one polarity and is followed in direct succession by a second pulse having a single stimulus phase with the opposite polarity of that of the preceding pulse. For purposes of this disclosure, delivery of two or more pulses in direct succession refers to the delivery of the pulses without the delivery of another pulse in between the pulses. In an alternating monophasic waveform, charge balance may be achieved by alternating the polarity of each successive monophasic stimulus pulse, where each pulse delivers substantially the same charge. Each successive monophasic pulse may be separated by a time interval (i.e., delay) that is greater than zero, during which no or substantially no stimulation pulse is delivered.

Figure 7:
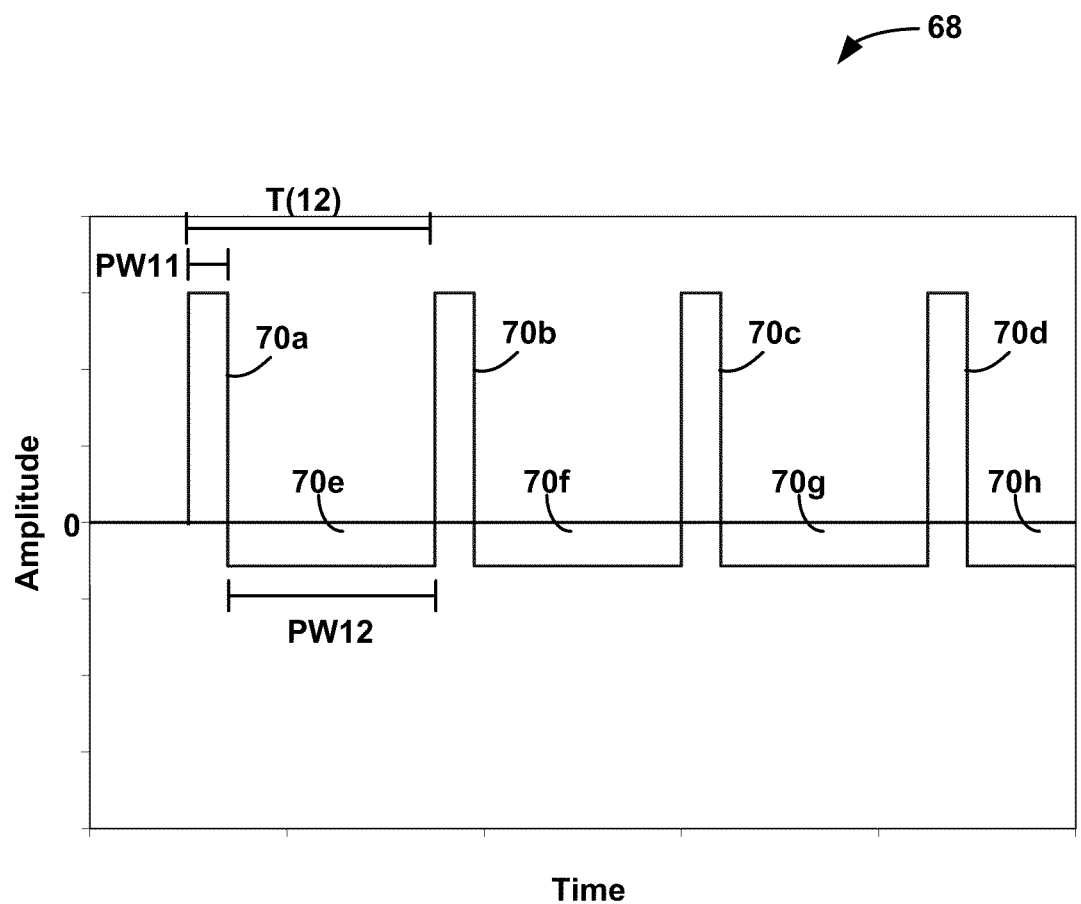
FIG. 7 is a plot illustrating another example waveform representing an example series of electrical stimulation for delivery to a patient.

Another example waveform that may be utilized for gastric electrical stimulation may include the example waveform is shown in FIG. 7. In some examples, such a waveform may be referred to as a "asymmetric biphasic rectangular pulse waveform," or "asymmetric biphasic pulses waveform," or "asymmetric biphasic waveform." As will be described in greater detail below, in FIG. 7, a first rectangular stimulation pulse followed by a second, rectangular pulse of opposite polarity. The first and second pulses may be coupled pulse pairs, which is described in further detail below. The second pulse lasts until the leading edge of the subsequent pulse, which may be the first of another coupled pulse pair. The amplitude of the second pulse may be selected to exactly offset the charge delivered in the first pulse based on the pulse width of the second pulse. In such examples, the amplitude of the second pulse is the minimum amplitude that allows the first and second pulses to be substantially charged balanced.

While examples of the disclosure are generally described with regard to gastric stimulation therapy and, in particular, the delivery of stimulation therapy to the stomach or other gastrointestinal organs of a patient, examples are not limited to such applications. In some examples, examples of the disclosure may apply to other types of stimulation therapy in a manner that effectively treats a patient condition other than that of a GI tract condition. For example, in some examples, such electrical stimulation may be generated and delivered to a patient to provide for electrical stimulation of the urinary bladder, urinary sphincter electrical stimulation, and/or skeletal muscles, e.g., via one or more intramuscular electrodes. Skeletal muscle stimulation may be used to cause limb movement, e.g., in the case of paralysis of the stimulated limbs.

In some examples, such electrical stimulation may be generated and delivered to provide for electrical stimulation of one or more patient nerve structures or sites. For example, a medical device may be configured to generate and deliver electrical stimulation in accordance with one or more aspects of this disclosure to the brain of a patient via one or more deep brain stimulating electrodes. Such stimulation may be referred to as deep brain stimulation (DBS) therapy. In one example, example DBS may include stimulation of the thalamic nucleus, subthalamic nucleus (STN), substantia nigra, and/or globus pallidus internus (GPi) according to one or more of the example techniques of the disclosure to treat or manage movement disorders. In another example, example DBS may include stimulation of the hypothalamus according to one or more of the example techniques of the disclosure to treat or manage pain and/or eating disorders including obesity. In another example, example DBS may include stimulation of the lateral or ventral medial hypothalamus, arcuate nucleus, paraventricular nucleus, nucleus accumbens, nucleus tractus solatarius, and/or ventral tegmental area according to one or more of the example techniques of the disclosure to treat or manage the eating disorders including obesity. In another example, example DBS may include stimulation of the frontal cortex, striatum, thalamus, hypothalamus, subgenual cingulate, and/or nucleus accumbens according to one or more of the example techniques of the disclosure to treat or manage depression or OCD.

As another example, a medical device may generate and deliver spinal cord stimulation (SCS), peripheral nerve stimulation, and/or peripheral nerve field stimulation (PNFS) in accordance with one or more of the examples described herein. In one example, stimulation may be delivered to the spinal cord to treat neuropathic pain. In another example, stimulation may be delivered to the one or more sacral nerves (e.g. S3 or S4) for treatment of urinary incontinence, constipation, or fecal incontinence. In another example, stimulation may be delivered to the vagus nerve for treatment of eating disorders, anxiety, schizophrenia, depression, epilepsy, or hormonal disorders. In another example, stimulation may be delivered to the hypoglossal nerve for treatment of sleep apnea. In another example, diaphragm stimulation may be provided, for example, to manage respiration of a patient. For example, such stimulation may be delivered to the phrenic nerve of a patient to induce or otherwise manage respiration of a patient.

As another example, a medical device may generate and deliver electrical stimulation to other non-GI tract body organs including, e.g., diaphragm, heart, liver, pancreas, kidney, and/or blood vessels, in accordance with one or more examples described herein. In one example, stimulation may be delivered to the heart for cardiac pacing for treatment of brachycardia.

In each case described above, the electrical stimulation therapy may be configured to effectively treat one or more patient conditions associated with the particular type of stimulation therapy.

The various techniques and features described in this disclosure may be implemented within an external programmer, an external or implantable gastric electrical stimulator, or a combination of both. The external programmer may be a patient programmer that accompanies a patient through a daily routine. Various examples of programmers, stimulators and associated functionality are provided for illustration, but without limitation of the various aspects of the disclosure as broadly embodied and described herein.

FIG. 1 is a schematic diagram illustrating an example implantable gastric stimulation system 10. System 10 is configured to deliver gastric stimulation therapy to the GI tract of patient 16. Patient 16 may be a human or non-human patient. However, system 10 will generally be described in the context of delivery of gastric stimulation therapy to a human patient, e.g., to treat obesity or gastroparesis.

As shown in FIG. 1, system 10 may include an IMD 12 and an external patient programmer 14, both shown in conjunction with a patient 16. In some examples, IMD 12 may be referred to generally as an implantable stimulator. Patient programmer 14 and IMD 12 may communicate with one another to exchange information such as commands and status information via wireless telemetry.

IMD 12 may deliver electrical stimulation energy, which may be constant current or constant voltage based pulses, to one or more targeted locations within patient 16 via one or more electrodes 24 and 26 carried on implantable leads 18 and 20. IMD 12 may generate and deliver the electrical stimulation pulses based on the stimulation parameters defined by one or more programs used to control delivery of stimulation energy. The parameter information defined by the stimulation programs may include information identifying which electrodes have been selected for delivery of stimulation according to a stimulation program, the polarities of the selected electrodes, i.e., the electrode configuration for the program, voltage or current amplitude, pulse rate, pulse shape, and pulse width of stimulation delivered by the electrodes. Delivery of stimulation pulses will be described for purposes of illustration. However, stimulation may be delivered in other forms, such as continuous waveforms. In some embodiments, system 10 may further include a drug delivery device that delivers drugs or other agents to the patient for obesity or gastric motility therapy, or for other nongastric related therapies. Again, system 10 may use an external, rather than implanted, stimulator, e.g., with percutaneously implanted leads and electrodes.

As will be described in greater detail below, IMD 12 may generate and deliver electrical stimulation using one or more waveforms described herein. For example, IMD 12 may generate and deliver electrical stimulation including a series of pulses represented by any of the example waveforms shown in FIGS. 5-9. The delivery of electrical stimulation using the example waveforms shown in FIGS. 5-9, and FIGS. 6A, 6B, and 7 in particular may effectively treat one or more patient conditions such as obesity, e.g., by inducing gastric distension of stomach 22.

Leads 18 and 20 each may include one or more electrodes 24 and 26 for delivery of the electrical stimulation pulses to stomach 22. In an example in which leads 18 and 20 each carry multiple electrodes, the multiple electrodes may be referred to as an electrode array. Combinations of two or more electrodes on one or both of leads 18, 20 may form bipolar or multipolar electrode pairs. For example, two electrodes on a single lead may form a bipolar arrangement. Similarly, one electrode on a first lead and another electrode on a second lead may form a bipolar arrangement. Various multipolar arrangements also may be realized. A single electrode 24, 26 on leads 18, 20 may form a unipolar arrangement with an electrode carried on a housing of IMD 12. Although the electrical stimulation, e.g., pulses or continuous waveforms, may be delivered to other areas within the gastrointestinal tract, such as, e.g., the esophagus, duodenum, small intestine, and/or large intestine, delivery of stimulation pulses to stomach 22 will generally be described in this disclosure for purposes of illustration. In the example of FIG. 1, electrodes 24, 26 are placed in lesser curvature 23 of stomach 22. Alternatively, or additionally, electrodes 24, 26 could be placed in the greater curvature of stomach 22 or at some other location of stomach 22.

In some examples, system 10 may be configured to deliver electrical stimulation therapy in a manner that influences that gastric distension of stomach 22 of patient 12. Gastric distension may generally refer to an increase in gastric volume or a relaxation in gastric muscle tone. Hence, a volumetric increase associated with gastric distension may be indicative of a state or relaxation of gastric muscle tone. In general, in accordance with this disclosure, gastric distention, increase in gastric volume and relaxation of gastric muscle tone may be used interchangeably to generally refer to a relative state of contraction or relaxation of the stomach muscle. In some cases, increased gastric distention may correlate with reduced food intake by a patient.

The state of contraction or relaxation of the stomach muscle may be evaluated using a device called a balloon barostat. The Distender Series II™, manufactured by G&J Electronics, Inc., Toronto, Ontario, Canada, is an example of a balloon barostat system that may be used to diagnose certain gastric motility disorders. Using this system, a balloon is inserted into the stomach, and inflated to a pressure just above the abdominal pressure, referred to the minimum distending pressure. The barostat is configured so that the pressure in the balloon is maintained at a constant pressure. If the state of contraction of stomach muscle decreases, i.e., the state of relaxation of the stomach muscle increases, then the balloon volume will increase. A decrease in the state of stomach muscle contraction, if measured under conditions of constant balloon pressure, indicates a change in gastric muscle tone, i.e., gastric muscle relaxation, and is sometimes referred to as a change in gastric distention, gastric volume, or gastric tone. More particularly, a decrease in muscle contraction corresponds to an increase in muscle relaxation and promotes distention, which may be measure in terms of an increase in gastric volume using balloon barostat evaluation.

Gastric stimulation therapy is generally described herein as being provided to cause gastric distension, which may be associated with an increase in gastric volume and an increase in gastric muscle tone relaxation. Alternatively or additionally, gastric stimulation therapy may be delivered by system 10 to induce nausea, cause regurgitation or vomiting (e.g., if too much food is consumed), or cause other actions to treat certain patient disorders. In some examples, gastric stimulation therapy may be delivered by system 10 to prevent regurgitation or reflux (e.g., in the case of gastroesophageal reflux disease (GERD)). In other embodiments, gastric stimulation therapy parameters may be selected to induce or regulate gastric motility, while in other embodiments the gastric stimulation therapy parameters are selected not to induce or regulate gastric motility but to promote gastric distension.

Inducing gastric distension in patient 16 may cause patient 16 to feel prematurely satiated before or during consumption of a meal. Increased gastric distension and volume are generally consistent with a decreased state of stomach muscle contraction, which conversely may be referred to as an increased state of stomach muscle relaxation. While gastric stimulation therapy is shown in this disclosure to be delivered to stomach 22, the gastric stimulation therapy may be delivered to other portions of patient 16, such as the duodenum or other portions of the small intestine.

Gastric distension tends to induce a sensation of fullness and thereby discourages excessive food intake by the patient. The therapeutic efficacy of gastric electrical stimulation in managing obesity depends on a variety of factors including the values selected for one or more electrical stimulation parameters and target stimulation site. Electrical stimulation may have mechanical, neuronal and/or hormonal effects that result in a decreased appetite and increased satiety. In turn, decreased appetite results in reduced food intake and weight loss. Gastric distension, in particular, causes a patient to experience a sensation of satiety, which may be due to expansion of the stomach, biasing of stretch receptors, and signaling fullness to the central nervous system.

In some examples, system 10 may be configured to provide multi-site gastric stimulation to patient 16 to vary the location of electrical stimulation to extend efficacious therapy of stomach 22. Multiple electrodes may be located on stomach 22 and connected to IMD 12. For example, electrodes 24, 26 may be electrode arrays in which IMD 12 may selectively activate one or more electrodes of the arrays during therapy to select different electrode combinations. The electrode combinations may be associated with different positions on the stomach or other gastrointestinal organ. For example, the electrode combinations may be located at the different positions or otherwise positioned to direct stimulation to the positions. In this manner, different electrode combinations may be selected to deliver stimulation to different tissue sites. In some examples, IMD 12 may deliver electrical stimulation to stomach 22 via a single electrode that forms a unipolar arrangement with a reference electrode on the housing of IMD 12.

The selection of electrodes forming an electrode combination used for delivery of electrical therapy at one time may change to a different selection of electrodes forming an electrode combination for delivery of electrical therapy at a different time. The selection may vary between each delivery of stimulation or a predetermined number of delivery periods or total amount of delivery time. The electrical stimulation therapies delivered at respective site may be configured to produce a substantially identical therapeutic result. The different electrode combinations at each site may provide different stimulation channels. As an example, stimulation delivered via the first and second channels may be configured to produce gastric distention, nausea or discomfort to discourage food intake by the patient. In some cases, the stimulation may be configured to regulate gastric motility. In other cases, the stimulation may be configured to not regulate motility, and instead promote distention, nausea or discomfort.

Figure 4A:
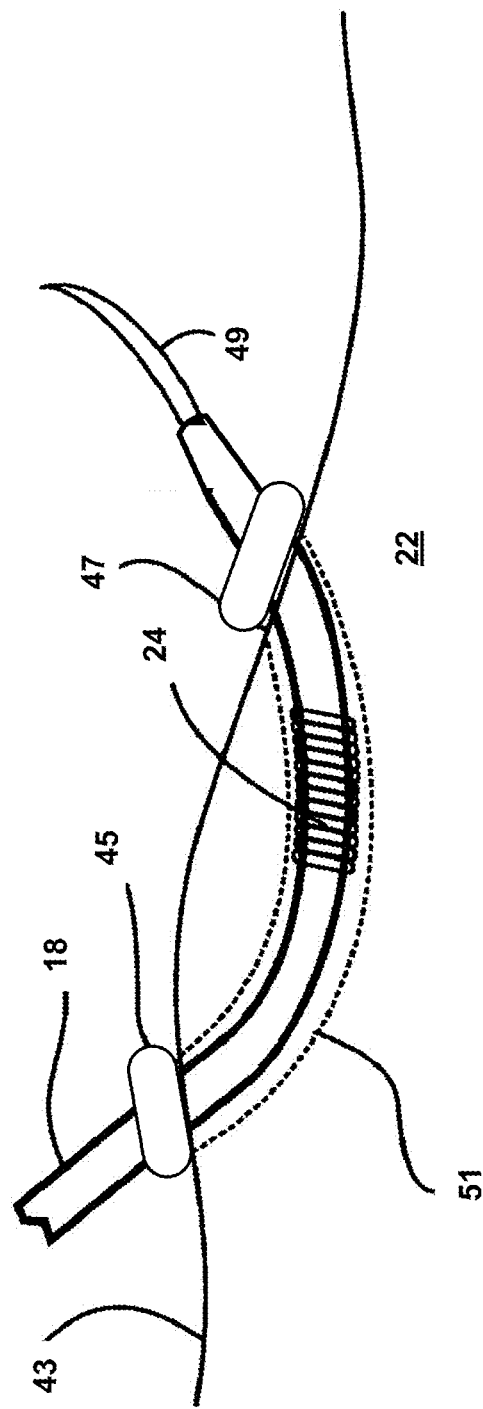
FIG. 4A is a conceptual diagram illustrating example lead including an example electrode positioned on the stomach of the patient for gastric electrical stimulation.

With further reference to FIG. 1, at the outer surface of stomach 22, e.g., along the lesser curvature 23, leads 18, 20 penetrate into tissue such that electrodes 24 and 26 are positioned to deliver stimulation to stomach 22. For example, lead 24 may be tunneled into and out of the wall of stomach 22 and then anchored in a configuration that allows electrode 24 carried on lead 24 to be located within the wall of stomach 22. Electrode 24 may then form a unipolar arrangement with a reference electrode on the housing of IMD 13 to deliver electrical stimulation to the tissue of stomach 22. Such an example is shown in FIG. 4A below.

As mentioned above, the parameters of the stimulation pulses generated by IMD 12 may be selected to distend stomach 22 and thereby induce a sensation of fullness, i.e., satiety. In some embodiments, the parameters of the stimulation pulses also may be selected to induce a sensation of nausea. In each case, the induced sensation of satiety and/or nausea may reduce a patient's desire to consume large portions of food. Alternatively, the parameters may be selected to regulate motility, e.g., for gastroparesis. Again, the stimulation pulses may be delivered elsewhere within the gastrointestinal tract, either as an alternative to stimulation of lesser curvature 23 of stomach 22, or in conjunction with stimulation of the lesser curvature of the stomach. As one example, stimulation pulses could be delivered to the greater curvature of stomach 22 located opposite lesser curvature 23.

IMD 12 may be constructed with a biocompatible housing, such as titanium, stainless steel, or a polymeric material, and is surgically implanted within patient 16. The implantation site may be a subcutaneous location in the side of the lower abdomen or the side of the lower back. IMD 12 is housed within the biocompatible housing, and includes components suitable for generation of electrical stimulation pulses. IMD 12 may be responsive to patient programmer 14, which generates control signals to adjust stimulation parameters. In some examples, IMD 12 may be formed as an RF-coupled system in which an external controller such as patient programmer 14 or another device provides both control signals and inductively coupled power to an implanted pulse generator.

Electrical leads 18 and 20 are flexible and include one or more internal conductors that are electrically insulated from body tissues and terminated with respective electrodes 24 and 26 at the distal ends of the respective leads. The leads may be surgically or percutaneously tunneled to stimulation sites on stomach 22. The proximal ends of leads 18 and 20 are electrically coupled to the pulse generator of IMD 12 via internal conductors to conduct the stimulation pulses to stomach 22 via electrodes 24, 26.

Leads 18, 20 may be placed into the muscle layer or layers of stomach 22 via an open surgical procedure, or by laparoscopic surgery. Leads also may be placed in the mucosa, submucosa, and/or muscularis by endoscopic techniques or by an open surgical procedure. Electrodes 24, 26 may form a bipolar pair of electrodes. Alternatively, IMD 12 may carry a reference electrode to form an "active can" or unipolar arrangement, in which one or both of electrodes 24, 26 are unipolar electrodes referenced to the electrode on the pulse generator. The housing of IMD 12 may itself serve as a reference electrode for the active can arrangement. A variety of polarities and electrode arrangements may be used. Each lead 18, may carry a single electrode or an electrode array of multiple electrodes, permitting selection of different electrode combinations, including different electrodes in a given electrode array, and selection of different polarities among the leads for delivery of stimulation.

In some examples, IMD 12 may be a leadless implantable device that is attached to the outside of stomach muscle, implanted inside of stomach 22, or inside or outside at any location of the gastrointestinal tract of patient 12. In some examples, such as those in which IMD 12 is implanted inside of stomach 22, IMD 12 may be implanted using a an esophageal approach, which may be a relatively simple medical procedure. In either case, IMD 12 may include at least two individual electrodes to deliver the stimulation to stomach 12. In some examples, the housing of IMD 12 may act as one electrode, where at least one non-housing electrode can be an electrically isolated electrode referenced to the housing of IMD 12 to deliver stimulation. IMD 12 may be secured inside or outside at desired position of stomach 22 using any suitable attachment technique, including screwing-in, hooking and clamping of IMD 12. Leadless IMD 12 may deliver stimulation to patient 12 according to one or more examples described in the disclosure.

Patient programmer 14 transmits instructions to IMD 12 via wireless telemetry. Accordingly, IMD 12 includes telemetry interface electronics to communicate with patient programmer 14. Patient programmer 14 may be a small, battery-powered, portable device that accompanies patient 16 throughout a daily routine. Patient programmer 14 may have a simple user interface, such as a button or keypad, and a display or lights. Patient programmer also may include any of a variety of audible, visual, graphical or tactile output media. Patient programmer 14 may be a hand-held device configured to permit activation of stimulation and adjustment of stimulation parameters.

Alternatively, patient programmer 14 may form part of a larger device including a more complete set of programming features including complete parameter modifications, firmware upgrades, data recovery, or battery recharging in the event IMD 12 includes a rechargeable battery. Patient programmer 14 may be a patient programmer, a physician programmer, or a patient monitor. In some embodiments, patient programmer 14 may be a general purpose device such as a cellular telephone, a wristwatch, a personal digital assistant (PDA), or a pager.

Electrodes 24, 26 carried at the distal ends of lead 18, 20, respectively, may be attached to the wall of stomach 22 in a variety of ways. For example, the electrode may be formed as a gastric electrode that is surgically sutured onto the outer wall of stomach 22 or fixed by penetration of anchoring devices, such as hooks, needles, barbs or helical structures, within the tissue of stomach 22. Also, surgical adhesives may be used to attach the electrodes. In some cases, the electrodes 24, 26 may be placed in the lesser curvature 23 on the serosal surface of stomach 22, within the muscle wall of the stomach, or within the mucosal or submucosal region of the stomach. Alternatively, or additionally, electrodes 24, 26 may be placed in the greater curvature of stomach 22 such that stimulation is delivered to the greater curvature.

In some examples, system 10 may include multiple stimulators 12 or multiple leads 18, 20 to stimulate a variety of regions of stomach 22. Stimulation delivered by the multiple stimulators may be coordinated in a synchronized manner, or performed without communication between stimulators. Also, the electrodes may be located in a variety of sites on the stomach, or elsewhere in the gastrointestinal tract, dependent on the particular therapy or the condition of patient 16. Stimulation delivered by the multiple stimulators may be coordinated in a synchronized manner, or performed independently without communication between stimulators. As an example, one stimulator may control other stimulators by wireless telemetry, all stimulators may be controlled by patient programmer 14, or the stimulators may act autonomously subject to parameter adjustment or downloads from patient programmer 14.

Figure 2:
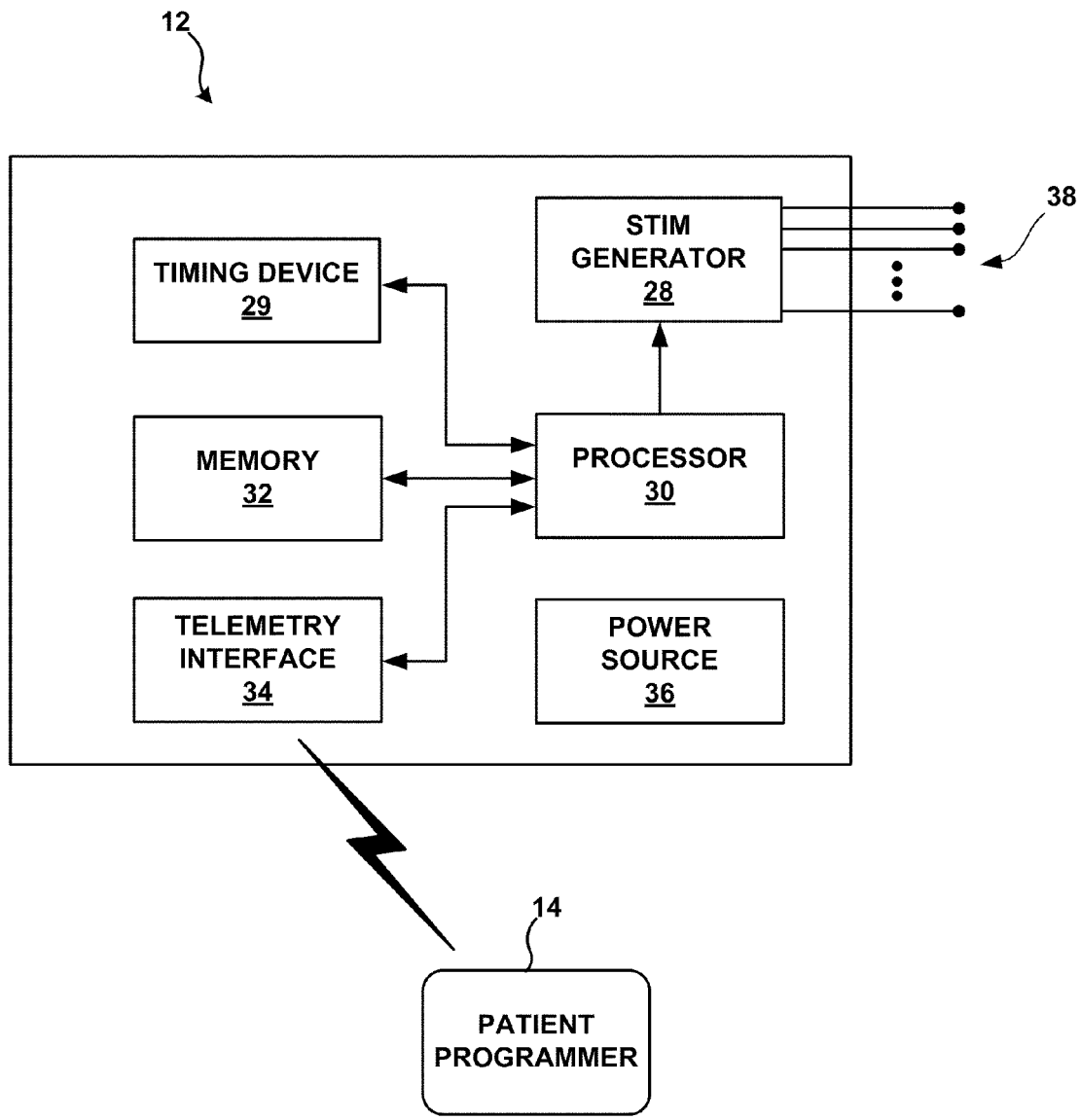
FIG. 2 is a block diagram illustrating example components of an implantable gastric electrical stimulator that delivers gastric electrical stimulation therapy.

FIG. 2 is a block diagram illustrating example components of IMD 12 that delivers gastric stimulation therapy to patient 16. In the example of FIG. 2, IMD 12 includes stimulation generator 28, processor 30, memory 32, wireless telemetry interface 34 and power source 36. In some embodiments, IMD 12 may generally conform to the Medtronic Itrel 3 Neurostimulator, manufactured and marketed by Medtronic, Inc., of Minneapolis, Minn. However, the structure, design, and functionality of IMD 12 may be subject to wide variation without departing from the scope of the disclosure as broadly embodied and described in this disclosure.

Processor 30 controls stimulation generator 28 by setting and adjusting stimulation parameters such as pulse amplitude, pulse rate, pulse width and duty cycle, in the case that stimulation generator 28 generates pulses. Alternative embodiments may direct stimulation generator 28 to generate continuous electrical signals, e.g., a sine wave. Processor 30 may be responsive to parameter adjustments or parameter sets received from patient programmer 14 via telemetry interface 34. Hence, patient programmer 14 may program IMD 12 with different sets of operating parameters. In some embodiments, stimulation generator 28 may include a switch matrix. Processor 30 may control the switch matrix to selectively deliver stimulation pulses from stimulation generator 28 to different electrodes 38 carried by one or more leads 18, 20 (FIG. 1). In some examples, processor 30 may control stimulation generator to deliver electrical stimulation including a series of pulse consistent with one or more example waveforms described herein. In some embodiments, IMD 12 may deliver different stimulation programs to patient 16 on a time-interleaved basis with one another.

Memory 32 stores instructions for execution by processor 30, including operational commands and programmable parameter settings. Example storage areas of memory 32 may include instructions associated with one or more therapy programs, which may include each program used by IMD 12 to define parameters and electrode combinations for gastric stimulation therapy. Memory 32 may store one or more therapy programs containing instructions for delivering a series of electrical stimulation pulses consistent with one or more example waveform described herein.

Processor 30 may access a clock or other timing device 29 within IMD 12 to determine pertinent times, e.g., for enforcement of therapy schedules, lockout periods, and therapy windows, and may synchronize such times with times maintained by patient programmer 14. Memory 32 may include one or more memory modules constructed, e.g., as random access memory (RAM), read-only memory (ROM), non-volatile random access memory (NVRAM), electrically erasable programmable read-only memory (EEPROM), and/or FLASH memory. Processor 30 may access memory 32 to retrieve instructions for control of stimulation generator 28 and telemetry interface 34, and may store information in memory 32, such as operational information.

Wireless telemetry in IMD 12 may be accomplished by radio frequency (RF) communication or proximal inductive interaction of IMD 12 with patient programmer 14 via telemetry interface 34. Processor 30 controls telemetry interface 34 to exchange information with patient programmer 14. Processor 30 may transmit operational information and receive stimulation parameter adjustments or parameter sets via telemetry interface 34. Also, in some embodiments, IMD 12 may communicate with other implanted devices, such as stimulators or sensors, via telemetry interface 34. In some examples, telemetry interface 34 may be configured to wirelessly communicate with other devices using non-inductive telemetry.

Power source 36 delivers operating power to the components of IMD 12. Power source 36 may include a battery and a power generation circuit to produce the operating power. In some embodiments, the battery may be rechargeable to allow extended operation. Recharging may be accomplished through proximal inductive interaction between an external charger and an inductive charging coil within IMD 12. In other embodiments, an external inductive power supply may transcutaneously power IMD 12 whenever stimulation therapy is to occur.

IMD 12 is coupled to electrodes 38, which may correspond to electrodes 24 and 26 illustrated in FIG. 1, via one or more leads 18, 20. IMD 12 provides stimulation therapy to the gastrointestinal tract of patient 16. Stimulation generator 28 includes suitable signal generation circuitry for generating a voltage or current waveform with a selected amplitude, pulse width, pulse rate, and duty cycle. As described in this disclosure, the series of electrical stimulation pulses generated by stimulation generator 28 may be formulated with particular parameter values to define a waveform that is suitable to cause gastric distention of stomach 22 of patient 16. For example, as will be described in further detail below, the electrical stimulation delivered by IMD 12 may include monophasic rectangular pulses with alternating polarity.

In the example of FIGS. 1 and 2, IMD 12 includes leads 18, 20. In other embodiments, IMD 12 may be a leadless stimulator, sometimes referred to as a microstimulator, or combination of such stimulators. In this case, the housing of IMD 12 may include multiple electrodes to form electrode combinations for delivery of stimulation to the stomach, intestines, or other organs within patient 16. In additional embodiments, IMD 12 may include one, three, or more than three leads.

Figure 3:
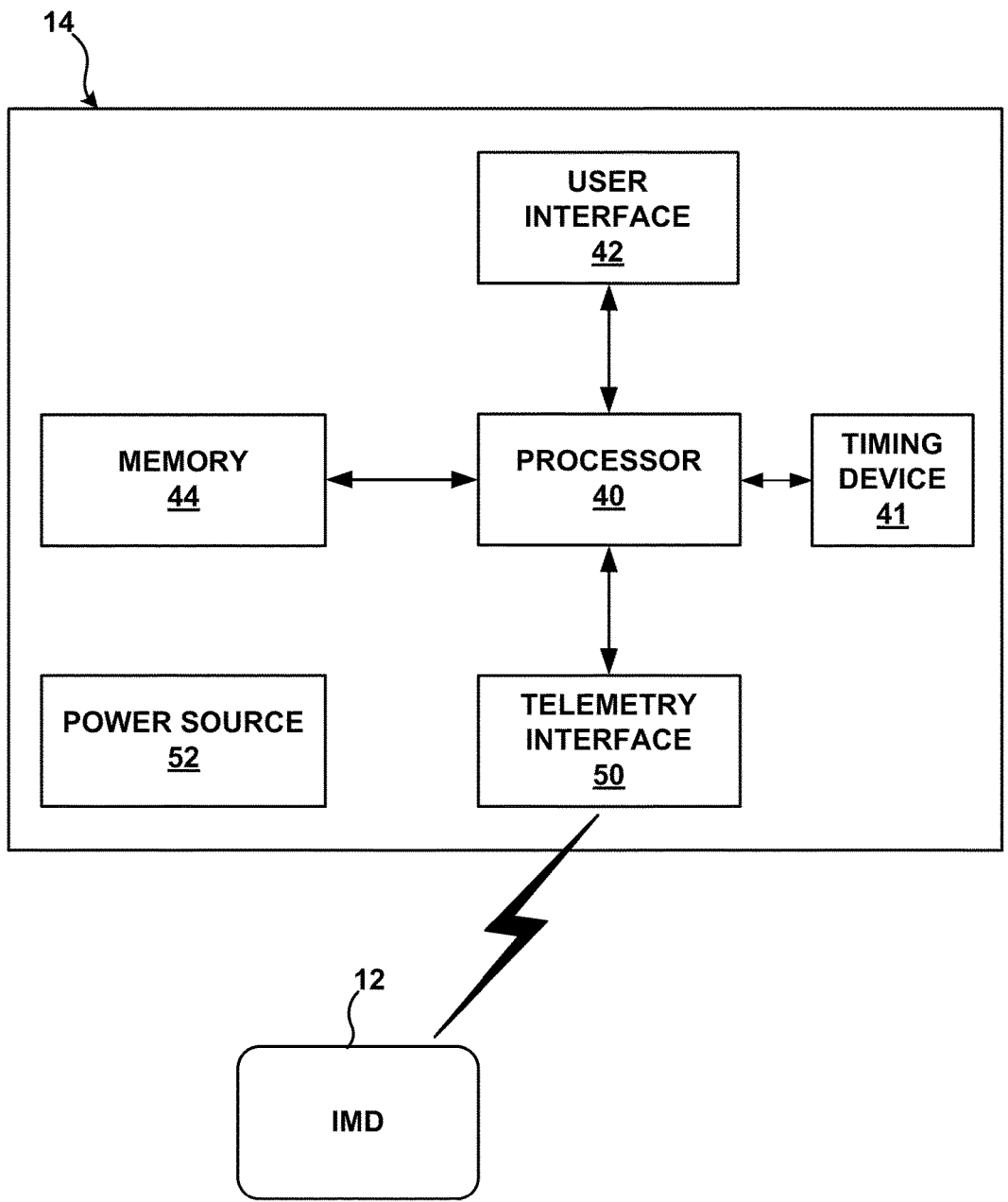
FIG. 3 is a block diagram illustrating example components of a patient programmer that receives patient input and communicates with a gastric electrical stimulator.

FIG. 3 is a block diagram illustrating example components of patient programmer 14 that receives patient input and communicates with IMD 12. As shown in FIG. 3, patient programmer is an external programmer that patient 16 uses to control the gastric stimulation therapy delivered by IMD 12. Patient programmer 14 includes processor 40, user interface 42, memory 44, telemetry interface 50 and power source 52. In addition, processor 40 may access a clock or other timing device 41 to adhere to lockout periods, therapy windows, and therapy schedules, as applicable. Patient 16 may carry patient programmer 14 throughout therapy so that the patient can initiate, stop and/or adjust stimulation as needed.

While patient programmer 14 may be any type of computing device, the patient programmer may preferably be a hand-held device with a display and input mechanism associated with user interface 42 to allow interaction between patient 16 and patient programmer 14. Patient programmer 14 may be similar to a clinician programmer used by a clinician to program IMD 12. The clinician programmer may differ from patient programmer by having additional features not offered to patient 16 for security, performance, or complexity reasons.

User interface 42 may include display and keypad (not shown), and may also include a touch screen or peripheral pointing devices. User interface 42 may be designed to receive an indication from patient 16 to deliver gastric stimulation therapy. The indication may be in the form of a patient input in the form of pressing a button representing the start of therapy or selecting an icon from a touch screen, for example. In alternative examples, user interface 42 may receive an audio cue from patient 16, e.g., the patient speaks to a microphone in order to perform functions such as beginning stimulation therapy. Patient programmer 14 acts as an intermediary for patient 16 to communicate with IMD 12 for the duration of therapy.

User interface 42 may provide patient 16 with information pertaining, for example, to the status of an indication or a gastric stimulation function. Upon receiving the indication to start stimulation, user interface 42 may present a confirmation message to patient 16 that indicates stimulation has begun. The confirmation message may be a picture, icon, text message, sound, vibration, or other indication that communicates the therapy status to patient 16.

Processor 40 may include one or more processors such as a microprocessor, a controller, a DSP, an ASIC, an FPGA, discrete logic circuitry, or the like. Processor 40 may control information displayed on user interface 42 and perform certain functions when requested by patient 16 via input to the user interface. Processor 40 may retrieve data from and/or store data in memory 44 in order to perform the functions of patient programmer 14 described herein. For example, processor 40 may generate a series of electrical stimulation pulses consistent with one or more examples waveforms described herein based upon instructions stored in memory 44, and processor 40 may then store the selection in memory 44.

Memory 44 may store information relating to the one or more stimulation programs used to define therapy delivered to patient 16. When a new program is requested by IMD 12 or patient 16, parameter information corresponding to one or more of the therapy programs may be retrieved from memory 44 and transmitted to IMD 12 in order adjust the gastric stimulation therapy. Alternatively, patient 16 may generate a new program during therapy and store it within memory 44. Memory 44 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

While patient programmer 14 is generally described as a hand-held computing device, the patient programmer may be a notebook computer, a cell phone, or a workstation, for example. In some embodiments, patient programmer 14 may comprise two or more separate devices that perform the functions ascribed to the patient programmer. For example, patient 16 may carry a key fob that is only used to start or stop stimulation therapy. The key fob may then be connected to a larger computing device having a screen via a wired or wireless connection when information between the two needs to be synchronized. Alternatively, patient programmer 14 may simply be small device having one button, e.g., a single "start" button, that only allows patient 16 to start stimulation therapy when the patient feels hungry or is about to eat.

FIG. 4A is a conceptual diagram illustrating lead 18 and electrode 24 positioned to deliver electrical stimulation to stomach 22 of patient 16. As shown, a portion of lead 18 is routed into and out the wall of stomach 22. The proximal end of lead 18 includes needle 49, which is used to penetrate the outer surface 43 of stomach 22 and tunnel lead 18 back out of the wall of stomach 22 to form tunnel 51 in the stomach wall. Anchors 45 and 47 fixate lead 18 at the entry and exit points, respectively, to maintain the position of lead 18 within tunnel 51 in the wall of stomach 22.

As shown, lead 18 is positioned within the wall of stomach 22 such that electrode 24 carried on lead 18 is located within tunnel 51 in the wall of stomach 22. Electrode 24 is a coil electrode having a conductive outer surface which is positioned adjacent to tissue of stomach 22. In some examples, to deliver electrical stimulation to stomach 22 from IMD 12, electrode 24 is referenced back to an electrode on the housing of IMD 12 to form a unipolar arrangement. In some examples, lead 18 may carry more than one electrode, each of which may be positioned within tunnel 51 to deliver electrical stimulation using a multipolar (e.g., bipolar) arrangement or unipolar arrangement.

Figure 4B:
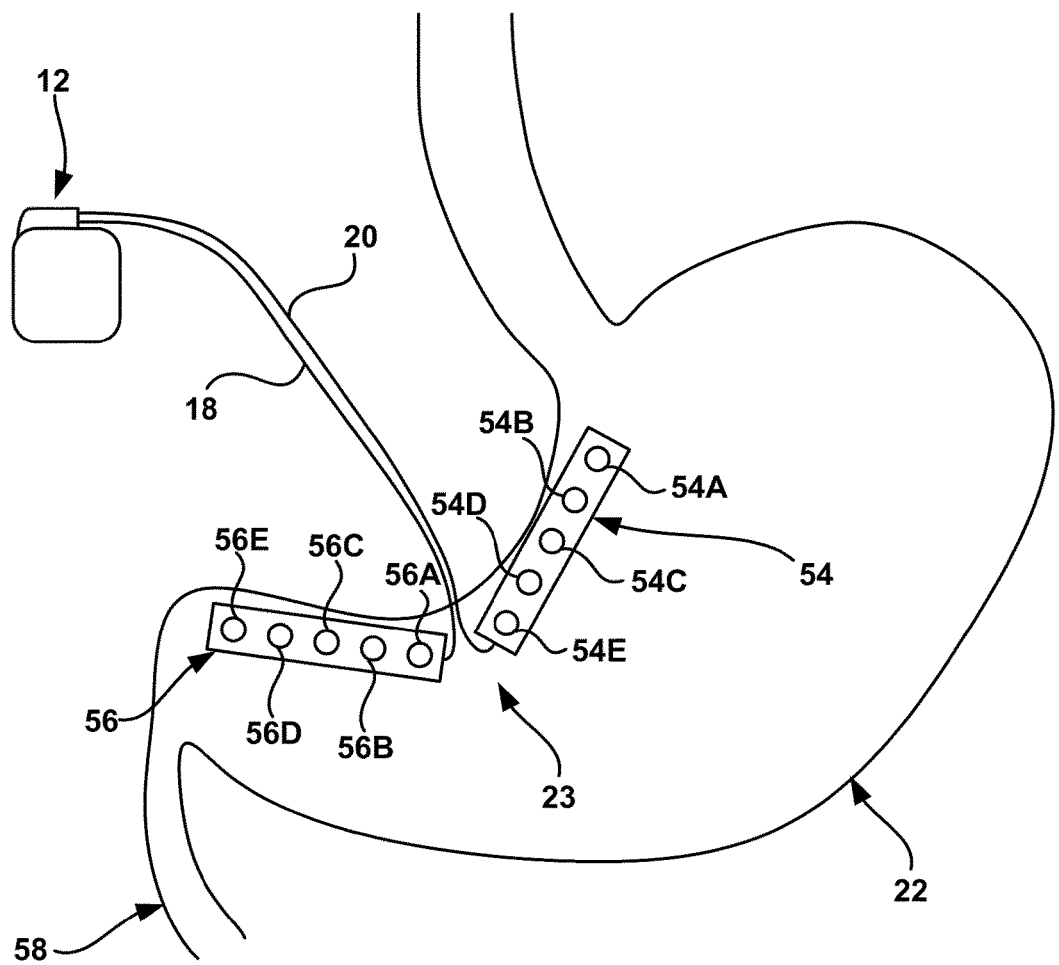
FIG. 4B is a conceptual diagram illustrating example electrode arrays positioned on the stomach of the patient for delivery of gastric electrical stimulation.

FIG. 4B is a conceptual diagram illustrating example electrode arrays 54 and 56 positioned on stomach 22 of patient 16. As shown in FIG. 4B, electrode arrays 54 and 56 are attached to the outside of stomach 22. Electrode array 54 includes five discrete electrodes 54A, 54B, 54C, 54D and 54E (collectively "electrodes 54") and electrode array 56 includes five discrete electrodes 56A, 56B, 56C, 56D and 56E (collectively "electrodes 56"). Electrode arrays 54 and 56 are positioned along lesser curvature 23 of stomach 22, but the electrode arrays may be positioned anywhere upon stomach 22 as desired by the clinician. In addition, one or both electrode arrays 54 may be positioned at different sites, such as on the duodenum or elsewhere along the small intestine.

Electrode arrays 54 and 56 are provided in place of electrodes 24 and 26 of FIG. 1. In this manner, electrode arrays 54 and 56 may be used as part of a multi-site electrical stimulation feature to distribute electrical stimulation energy among a larger number of varied tissue sites, instead of concentrating stimulation at a single tissue site. For example, electrode arrays 54, 56 may be used to support selection of different electrode combinations associated with different positions, or tissue sites, on a gastrointestinal organ such as the stomach. Each electrode array 54, 56 may include a plurality of electrodes, e.g., electrodes 54A-54E and electrodes 56A-56E, that may be individually selected to form a variety of electrode combinations that distribute electrical stimulation therapy to different therapy sites. Electrode combinations may include selected electrodes on different leads or the same lead. For example, an electrode combination may combine electrodes from array 54, array 56, or both array 54 and 56, as well as electrodes from other arrays, if provided.

In the example of FIG. 4B, electrode arrays 54 and 56 and electrodes 54A-54E and 56A-56E may not necessarily be sized in proportion to stomach 22. For example, electrode arrays 54 and 56 may be configured to be a smaller size so that the electrodes can be packed into a smaller area of stomach 22. Alternatively, electrode arrays 54 and 56 and their corresponding electrodes may differ in size on stomach 22. For example, electrodes in array 54 may each have a larger surface area than each of the electrodes in array 56. In addition, electrodes 54 may have differing surface areas between each of the electrodes. In this manner, varying electrode surface area may act as an additional anti-desensitization feature to slightly alter the stimulation therapy over time.

IMD 12 may deliver electrical stimulation to stomach 22 using one or more electrodes of electrode arrays 54 and 56. Each of the electrodes in arrays 54, 56 may be coupled to IMD 12 via a respective electrical conductor within leads 18, 20, and may be individually selectable. Each lead 18, 20 may include multiple conductors, each of which is coupled at a distal end to one of the electrodes in a respective electrode array 54, 56 and at the proximal end to a terminal of a switch device by which IMD 12 directs stimulation energy to selected electrodes, e.g., as anodes or cathodes. In some examples, as mentioned above, IMD 12 may deliver stimulation using one electrode from each of electrode arrays 54 and 56, multiple electrodes from one array and a single electrode from another array, or multiple electrodes in a single array.

IMD 12 may periodically deliver a low level electrical current to measure the electrical impedance between the IMD 12 and the electrodes 26 and or 24, or simply between the electrodes 26 and 24. This current could be on the order of 50 micro-amperes and be an alternating current with a frequency of at least 10 Hz, and preferably more than 250 Hz. Resulting voltage drop can be measured the estimate the electrical impedance of the path that the electrical current traverses. Changes in this electrical impedance would be resulting from the distension of the stomach and would be interpreted as the IMD as food intake by the subject. Therefore, the IMD could detect the onset of the meal consumption and turn on the stimulation. Furthermore, the changes in the impedance signal could be used to modulate the duration or the intensity of the stimulation, forming a closed loop control system. In one example, the stimulus is applied between the IMD 12 and electrode 24, while the resulting voltage is measured between the IMD 12 and the electrode 26, forming a three-lead configuration.

IMD 12 may cycle through or randomly select different electrodes from each of electrode arrays 54 and 56 to produce different electrode combinations to vary the stimulation tissue sites throughout therapy. In other examples, IMD 12 may deliver stimulation using a combination of any electrodes from only electrode array 54, only electrode array 56, or a combination of electrodes from electrode arrays 54 and 56. In alternative examples, the housing of IMD 12 may also be used as an electrode, e.g., in a unipolar arrangement in conjunction with one or more electrodes carried by one or more leads. The housing of IMD 12 may be referred to as a can electrode, return electrode, or active can electrode, as mentioned above.

While electrode arrays 54 and 56 are shown as each having five electrodes, electrode arrays 54 and 56 may have any number of electrodes desired by the clinician or necessary for efficacious therapy. Electrode arrays 54 and 56 may have differing numbers of electrodes, and IMD 12 may be connected to a different number of electrode arrays, such as only one array or more than three arrays. In addition, electrode arrays 54 and 56 may have corresponding electrodes configured in a different orientation than the linear orientation shown in FIG. 4B. For example, electrode arrays 54 and 56 may have electrodes oriented in a circular pattern, rectangular grid pattern, curved pattern, star pattern, or another pattern that may enhance the anti-desensitization feature of electrode arrays 54 and 56.

In general, multiple electrodes implanted at multiple tissue sites, as shown in FIG. 4B, may permit stimulation to be delivered to different stimulation sites at different times. For example, stimulation having substantially similar parameters or different parameters may be applied to different tissue sites during different therapy windows or therapy schedule time periods such that different tissue sites are stimulated. The stimulation parameters may be selected to achieve similar therapeutic effects, e.g., gastric distention, even though the stimulating is delivered to different tissue sites.

As described above, according to some examples of the disclosure, a medical device, such as, e.g., IMD 12 (FIG. 1), may be configured to generate and deliver electrical stimulation therapy to patient 12. The electrical stimulation therapy generated and delivered to patient from the medical device may include a series of pulses that are consistent with one or more example waveforms described herein. FIGS. 5-9 illustrate example waveforms defined by a series of pulses of electrical stimulation therapy which may be generated and delivered to a patient by a medical device, e.g., to treat one or more gastric disorders or diseases. For purposes of illustration, the example waveforms of FIGS. 5-9 are described with regard to therapy system 10 of FIG. 1. However, examples of the disclosure may be incorporated into any suitable medical system or device capable of delivering electrical stimulation to a patient.

In some examples, two successive electrical stimulation pulses can be characterized as being coupled to one another. A coupled pair of electrical stimulation pulses may include a first electrical stimulation pulse of one polarity (anodic or cathodic) followed immediately, or with some fixed delay, by second electrical stimulation pulse of opposite polarity. When the coupled pair of electrical stimulation pulses are charge balanced, the charge of the first pulse is equal to but opposite of that of the charge of the second pulse. Notably, unlike uncoupled pulses, the timing of the delivery of two stimulus pulses that are coupled to one another is fixed. For example, for a plurality of pulses including multiple coupled pairs of pulses in which each coupled pair includes a first anodic pulse followed by a second cathodic pulse that are charged balanced, each of the coupled pairs of pulses may be delivered relative to each other at a set frequency that may be varied. However, the temporal relationship of the each pulses in a pair of coupled pulses is unaffected by the chosen frequency for delivery of the each coupled pair of pulses relative to one another. For example, while the interval between the leading edges of successive pulses of the same polarity will be longer at lower selected pulse frequencies, and shorter at higher selected pulse frequencies, the temporal relationship of the pair of coupled pulses of each coupled pair is unaffected by the chosen pulse frequency. The time elapsed between the first pulse and the second pulse is fixed, (e.g., at approximately zero or some fixed time delay) regardless of the selected frequency at which the coupled pairs of pulses are delivered.

Figure 5:
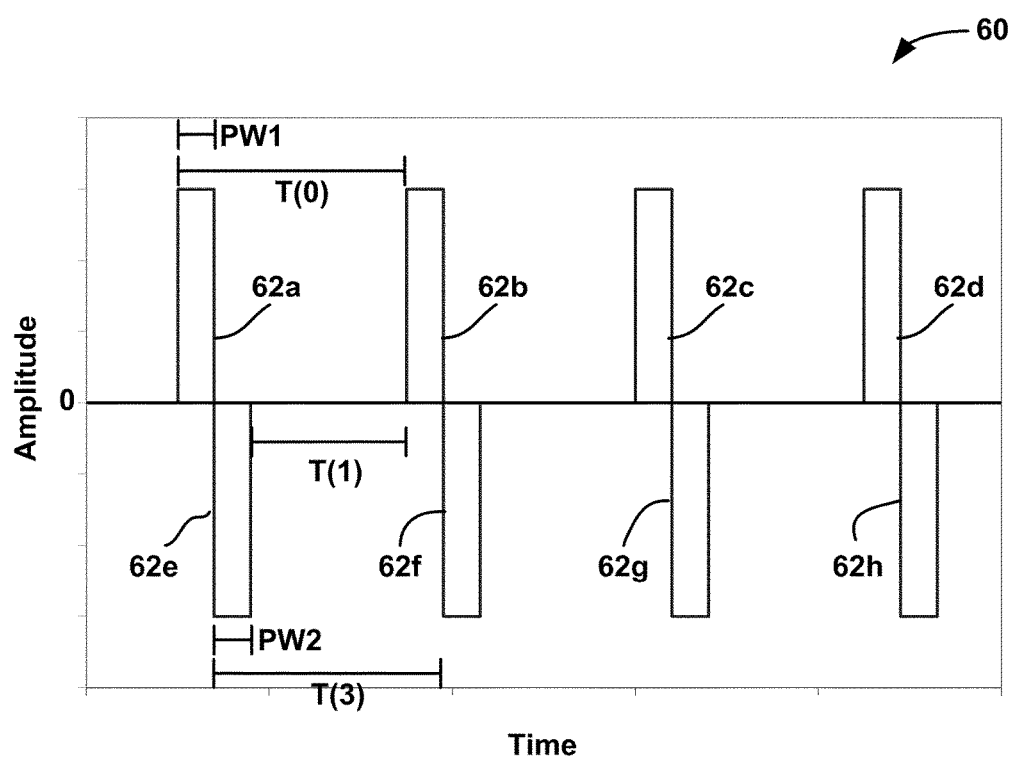
FIG. 5 is a plot illustrating an example waveform representing an example series of electrical stimulation pulses for delivery to a patient.

FIG. 5 is a plot illustrating an example waveform 60 representing an example series of electrical stimulation pulses for delivery to patient 16. In particular, in FIG. 5, waveform 60 includes first stimulation pulse 62a, second stimulation pulse 62b, third stimulation pulse 62c, fourth stimulation pulse 62d, fifth stimulation pulse 62e, sixth stimulation pulse 62f, seventh stimulation pulse 62g, and eighth stimulation pulse 62h (collectively "series of stimulation pulses 62"). IMD 12 may generate and deliver gastric electric stimulation to stomach 22 of patient 16 via electrodes 24 and 26 carried on leads 18 and 20 respectively, where the gastric electric stimulation includes the series of electrical stimulation pulses 62 represented by waveform 60. In some examples, such electric stimulation may treat one or more patient conditions, e.g., by inducing the distention of stomach 22 of patient 16. Although the series of stimulation pulses 62 represented by waveform 60 are shown to include stimulation pulses 62a-62h, the gastric electric stimulation generated and delivered to patient 16 by IMD 12 may include any number of stimulation pulses that provide effective treatment to patient 16.

As shown in FIG. 5, the series of stimulation pulses 62 is a plurality of pulses including pairs of individual pulses that are coupled to one another. In particular, first pulse 62a is coupled with fifth pulse 62e, second pulse 62b is coupled with sixth pulse 62f, third pulse 62c is coupled with seventh pulse 62g, and fourth pulse 62d is coupled with eighth pulse 62h. As such, the temporal relationship between each pulse of a coupled pair of pulses is fixed. In the example shown in FIG. 5, the temporal relationship between each pulse of coupled pairs of pulses (e.g., pulses 62a and 62e, pulses 62b and 62f, and so forth) is such that the second pulse of the coupled pair (e.g., pulses 62e, 62f, 62g, and 62h) is delivered substantially immediately after the first pulse of the coupled pair (e.g., pulses 62a, 62b, 62c, and 62d, respectively) ends. The pulse width of each first pulse (i.e., pulses 62a-d) of the coupled pairs of pulses (which is equal to pulse width PW 1) is substantially equal to the pulse width of each second pulse (i.e., pulses 62e-h) of the coupled pairs of pulses (which is equal to pulse width PW2). Each first pulse (i.e., pulses 62a-d) of a coupled pair has substantially the same amplitude but opposite polarity of each second pulse (i.e., pulses 62e-h) of a coupled pair. In some examples, the fixed time delay between pulses of coupled pulse pairs may be less than the pulse width of the pulses of the pulse pair, e.g., less than pulse width PW1 of first pulse 62a.

In waveform 60, the coupled pairs of pulses (pulses 62a and 62e, pulses 62b and 62f, and so forth) are delivered at a set frequency, which is consistent with time interval T(0). As described above, the frequency that the coupled pairs of pulses are delivered does not change the timing that between each pulse in a coupled pair. After IMD 12 delivers fifth pulse 62e to stomach 22 of patient 16, there is a delay interval T(1) prior to the beginning of the subsequent coupled pulse pair (pulses 62b and 62f). Unlike that of the fixed relationship between pulses of coupled pulse pairs, the timing between the delivery of respective coupled pulse pairs varies with the set frequency. For example, if the frequency of the delivery of coupled pulse pairs increases, then time intervals T(0), T(1) and T(3) decrease. Conversely, if the frequency of the delivery of coupled pulse pairs decreases, then time intervals T(0), T(1) and T(3) increase. However, the timing between each pulse of a coupled pulse pair does not change in either case.

Such a pattern is repeated throughout series of pulses 62 represented by waveform 60. IMD 12 may generate and deliver gastric electric stimulation to stomach 22 of patient 16 via electrodes 24 and 26 carried on leads 18 and 20 respectively, where the gastric electric stimulation includes the series of electrical stimulation pulses 62 represented by waveform 60. In some examples, such electric stimulation may treat one or more patient conditions, e.g., by inducing the distention of stomach 22 of patient 16. Although the series of stimulation pulses 62 represented by waveform 60 are shown to include eight stimulation pulses 62a-62h, comprising four coupled pairs of pulses delivered at a constant frequency, the gastric electric stimulation generated and delivered to patient 16 by IMD 12 may include any number of stimulation pulses and pairs of pulses that provide effective treatment to patient 16.

As represented by waveform 60, IMD 12 delivers stimulation pulses 62a-h in direct succession with one another. All of stimulation pulses 62a-d have the same polarity (all cathodic or all anodic), and all of stimulation pulses 62e-h have the same polarity, which is opposite from that of the polarity of pulses 62a-d. Furthermore, each pulse of the series of pulses 62 has approximately the same amplitude and pulse width, although the polarity of the pulses alternates as indicated in FIG. 5. As such, for the series of pulses 62, the charge of each of pulses 62a-d is approximately equal to and opposite of that of the charge each of pulses 62e-h, i.e., the area between the amplitude curve and the zero amplitude line for each of pulses 62a-62d is approximately equal to the corresponding area between the amplitude curve and zero amplitude for each of pulses 62e-h. Accordingly, each coupled pair of pulses of the series of pulse 62 is charge balanced and the entire series of pulses 62 may be considered charge balanced.

In some examples, waveform 60 may be described as "symmetric rectangular biphasic" or, simply "symmetric biphasic". Increasing the constant frequency of coupled pair pulses in FIG. 5 would decrease T(0), T(1) and T(3), but would not change the temporal relationship between the respective pulses of each coupled pulse pair. In the example shown in FIG. 5, such a frequency change would not change the fact that the first pulse of a coupled pulse pair is followed substantially immediately by a recharge pulse. Likewise, decreasing the constant frequency of coupled pulse pairs in FIG. 5 would increase T(0), T(1) and T(3), but would leave the temporal relationship between the first pulse and second pulse of a coupled pulse pair unaltered. While in the example in FIG. 5 the time between each pulse of a coupled pulse pair is substantially zero, this interval is often fixed at some fixed positive value, generally much less than the pulse width PW1.

FIG. 6A is a plot illustrating another example waveform 64 representing an example series of electrical stimulation pulses for delivery to patient 16. In particular, first stimulation pulse 66a, second stimulation pulse 66b, third stimulation pulse 66c, and fourth stimulation pulse 66d (collectively "series of stimulation pulses" 66) are represented by waveform 64. IMD 12 may generate and deliver gastric electric stimulation to stomach 22 of patient 16 via electrodes 24 and 26 carried on leads 18 and 20 respectively, where the gastric electric stimulation includes the series of electrical stimulation pulses 66 represented by waveform 64.

In some examples, such electric stimulation may effectively treat one or more patient conditions, e.g., by increasing the distension of stomach 22 of patient 16. Although series of stimulation pulses 66 represented by waveform 64 are shown to include four stimulation pulses 66a-d, the gastric electric stimulation generated and delivered to patient 16 by IMD 12 may include any number of stimulation pulses that provide effective treatment to patient 16.

As represented by waveform 64, IMD 12 delivers first stimulation pulse 66a, second pulse 66b, third stimulation pulse 66c, and fourth stimulation pulse 66d in direct succession with one another and in the order listed. In the series of stimulation pulses 66, each pulse has a polarity that is opposite of the polarity of the directly preceding pulse and the directly following pulse. For example, as delivered by IMD 12, first stimulation pulse 66a has a first polarity, which may be either anodic or cathodic, second stimulation pulse 66b has polarity opposite from that of first pulse 66a, third stimulation pulse 66c has a polarity opposite from that of second stimulation pulse 66b, and so forth.

Unlike waveform 60 (FIG. 5), in waveform 64 (FIG. 6A), a time interval that is greater than zero separates each respective pulse in the series of pulses 66. For example, a time interval T(4) greater than zero separates the trailing edge of first pulse 66a and leading edge of second pulse 66b. Similarly, a time interval T(5) greater than zero separates the trailing edge of second pulse 66b and leading edge of third pulse 66c.

Furthermore, unlike the series of pulses 62 represented by waveform 60 (FIG. 5), pulses 66a-66d do not form coupled pulse pairs with one another. Instead, the temporal relationship between each individual pulse in the series of pulses is dependent on the stimulation pulse frequency. In particular, time intervals T(4), T(5) and T(6) are depend on the frequency that the series of pulses are delivered and the pulse width of each pulse. If series of pulses 66 are delivered at an increased frequency while the pulse width is constant, then time intervals T(4), T(5) and T(6) all decrease. Conversely, if series of pulses 66 are delivered at an decreased frequency while the pulse width is constant, then time intervals T(4), T(5) and T(6) all increase.

In some examples, time intervals T(4), T(5) and T(6) may be substantially equal to one another such that pulses 66a-d are evenly spaced. In other examples, time interval T(4) may be different than that of time interval T(5) and/or time interval T(6). However, in each case, time intervals T(4), T(5) and T(6) are dependent on the frequency at which the series of pulses 66 are delivered since none of pulses 66a-d form coupled pulse pairs. In examples in which T(4), T(5) and T(6) are approximately equal to one another and pulses 66a-d each have approximately the same pulse width, the pulse frequency of series of pulses 66 may be determined by the time interval between the leading edge of each pulse, e.g., time interval T(7) between first pulse 66a and second pulse 66b. In some examples, the interpulse interval between directly successive pulses is not less than the pulse width of the successive pulses. For example, time interval T(4) may be greater than or equal to PW3 and PW4. In some examples, the interpulse intervals defined by the series of pulses 66 (i.e., time intervals T(4)-T(6)) may be greater than approximately 1 millisecond, such as, e.g., greater than 2 milliseconds or greater than 10 milliseconds or greater than 50 milliseconds. Unlike that of the fixed interval of time between pulses of the same coupled pulse pair in FIG. 5, the interpulse interval between each of pulses 70a-d is dependent on the pulse frequency and pulse width that the series of pulses 70a-d are delivered.

The overall charge of the series of pulses 66 of waveform 64 may be approximately zero. The charge of each pulse is dependent on the amplitude and pulse width of each respective pulse of the series of pulses 66. In some examples, the pulse width and amplitude of each respective pulse 66a-d may be selected such that the charge of first pulse 66a may be approximately equal to and opposite of that of the charge of second pulse 66b, and the charge of third pulse 66c may be approximately equal to and opposite of that of the charge of fourth pulse 66d. In some examples, each pulse of the series of pulses 66 may have approximately the same amplitude and pulse width. In other examples, the pulse width and amplitude may differ between pulses. In any case, the series of pulse 66 may be described as charged balanced even though the first pulse 66a is not followed substantially immediately by a second pulse 66b with an equal and opposite charge, as was the case in waveform 60 (FIG. 5). Instead, second pulse 66b is delivered after time interval T(4) greater than zero after the end first pulse 66a.

In some examples, waveform 66 may be referred to as representing "alternating monophasic rectangular pulses" or simple "alternating monophasic pulses". In the example in FIG. 5, the pulses in the sequence may have a constant width, such that PW3, PW4, PW5, and PW6 are substantially equal, and the pulses are being issued at a constant frequency, such that the time elapsed from the leading edge of one pulse in the sequence to the leading edge of the next pulse, T(7), is constant throughout the series of pulses. In the example shown in FIG. 5, T(7) may be 25 milliseconds, implying a constant pulse frequency of 40 hertz. Likewise, the constant pulse frequency implies that the intervals between successive pulses, during which the amplitude of stimulation delivered to the patient is approximately zero, are also of substantially equal duration, such that T(4), T(5) and T(6) in this example are substantially equal.

Unlike the symmetric biphasic waveform 60 (FIG. 5) the interval between every successive pulses of opposite polarity in waveform 64 (FIG. 6) may vary with the pulse frequency selected. This is because each pair of adjacent rectangular pulses with opposite polarity in waveform 64 are two uncoupled stimulus pulses, rather than some of the pulses forming coupled pulse pairs. An increase in pulse frequency for the alternating monophasic waveform 64 will cause the intervals between successive stimulus pulses of opposing polarity to decrease in duration, while a decrease in the selected pulse frequency will cause these intervals between successive pulses of opposite polarity to increase.

Figure 6B:
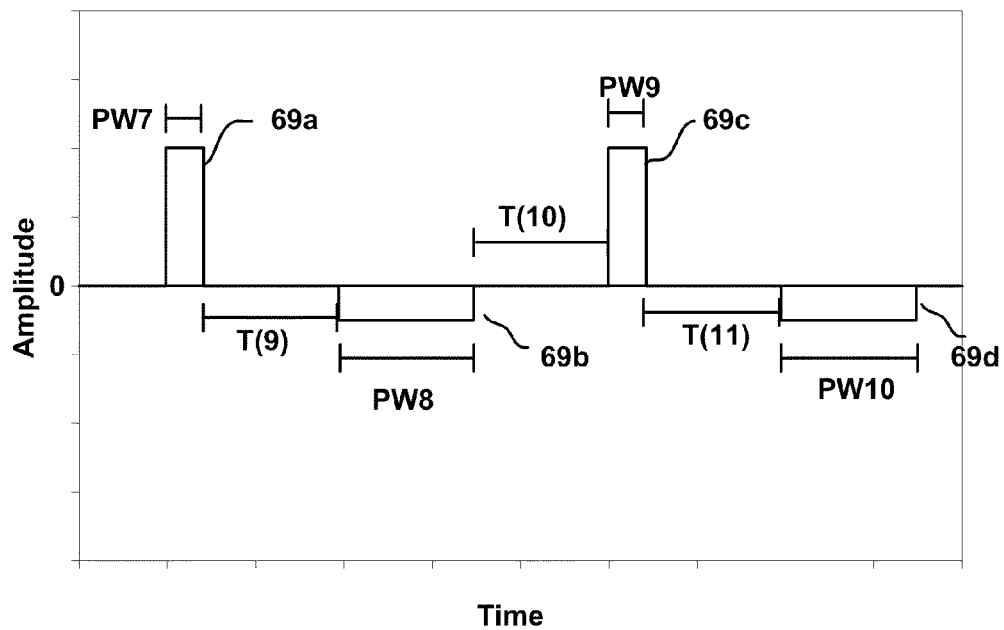
FIG. 6B is a plot illustrating another example waveform representing an example series of electrical stimulation for delivery to a patient.

FIG. 6B is a plot illustrating another example waveform 65 representing an example series of electrical stimulation pulses for delivery to patient 16. In particular, first stimulation pulse 69a, second stimulation pulse 69b, third stimulation pulse 69c, and fourth stimulation pulse 69d (collectively "series of stimulation pulses" 69) are represented by waveform 65. The series of pulses 69 of waveform 65 are substantially the same as the series of pulses 66 of waveform 64 in FIG. 6A. For example, none of pulses 66a-d form coupled pulse with each other. Instead, the temporal relationship between each of 66a-d is dependent on the frequency at which the series of pulses 66 is delivered. In some examples, time intervals T(9), T(10) and T(11) may be substantially the same, and may vary based on the frequency at which the series of pulses 69 are delivered to patient 16.

However, unlike that shown in FIG. 6A, the pulse width and pulse amplitude of the series of pulses 69 is not the same for each respective pulse 69a-d. In particular, first pulse 69a and third pulse 69c have substantially the same amplitude, which is greater than the amplitude of second pulse 69b and fourth pulse 69d, which also have substantially the same amplitude. Moreover, the pulse width PW 7 of first pulse 69a and pulse width PW9 of second third pulse 69c is substantially the same and less than that of the pulse width PW8 of second pulse 69b and PW 10 of fourth pulse 69d, which are also substantially the same as one another. Despite the difference in pulse widths and pulse amplitude, the pulse width and amplitude of each respective pulse may be selected such that the series of pulses 69 are substantially charge balanced. For example, first pulse 69a may have substantially the same but opposite charge from the charge of second pulse 69b.

IMD 12 may deliver the series of pulses represented by waveforms 64 and 65 to patient 16, e.g., to stomach 22, according to any suitable value for each of pulse width, pulse amplitude, and pulse frequency. In some examples, one or more of the stimulation parameters may be selected such that the electrical stimulation delivered by IMD 12 to stomach 22 of patient 16 causes the distension of stomach 22 to increase. In some examples, for constant current applications, pulses 66a-d may have a pulse amplitude greater than zero but less than or approximately equal to 25.0 milliamps, such as, e.g., a pulse amplitude between approximately 1 milliamp and approximately 12.0 milliamps, or between approximately 2 milliamps and approximately 25 milliamps. In some examples, for constant voltage applications, pulses 66a-d may have a pulse amplitude greater than zero but less than or approximately equal to 25.0 volts, such as, e.g., a pulse amplitude between approximately 1 volt and approximately 12.0 volts, or between approximately 2 volts and approximately 25 volts. Constant current and constant voltage applications refer to applications in which the current or voltage, respectively, is regulated or controlled to provide a desired level which could be constant or could be shaped, although in most cases the pulse may have a constant current or voltage. In some examples, pulses 66a-d may have a pulse width between approximately 0.05 milliseconds and approximately 1000 milliseconds, such as, e.g., between approximately 0.5 milliseconds and approximately 50 milliseconds. In some examples, pulses 66a-d may have a pulse width between approximately 0.5 milliseconds and approximately 20 milliseconds, such as, e.g., between approximately 1 millisecond and approximately 20 milliseconds. In other examples, pulses 66a-d may have a pulse width between approximately 0.1 milliseconds and approximately 20 milliseconds, such as, e.g., between approximately 1 millisecond and approximately 20 milliseconds. In some examples, pulses 66a-d may be delivered at a pulse frequency between approximately 0.05 Hz and the approximate value determined by dividing 1000 by 2 times the pulse width (in milliseconds) Hz, such as, e.g., between approximately 0.5 Hz and the approximate value determined by dividing 1000 by 2 times the pulse width (in milliseconds) Hz. In some examples, pulses 66a-d may be delivered at a pulse frequency between approximately 0.05 Hz and approximately 40 Hz, such as, e.g., between approximately 1 and approximately 40 Hz. In examples in which IMD 12 deliver electrical stimulation including series of pulse 66a-66d according to duty cycle, electrical stimulation may "on" between approximately 5% and approximately 100% of the time. Other values for each electrical stimulation parameters are contemplated. In each case, IMD 12 may generated and deliver electrical stimulation to patient 16 to cause substantial gastric distention and a sensation of fullness, which may result in reduced food intake and, ultimately, weight loss. In some examples, IMD 12 may deliver the series of pulses represented by waveforms 60 to patient 16 according to one or more of the above-described parameters.

In some examples, such pulses may be delivered via a lead-borne electrode (e.g., as a cathode) and an IMD housing electrode (can electrode) (e.g., as an anode) in a unipolar arrangement, or between bipolar or multipolar lead-borne electrodes. Furthermore, such pulses may be delivered as a continuous pulse train, or the pulses may be contained in periodic or aperiodic bursts of multiple pulses, or in periodic or aperiodic pulse burst envelopes containing multiple pulse bursts. The pulse bursts may be of the same duration or different durations. In some examples, IMD 12 may deliver electrical stimulation with a burst frequency between approximately 2 and approximately 15 bursts per minute. In some examples, IMD 12 may deliver bursts having a duration of between approximately 0.1 seconds and approximately 15 seconds.

FIG. 7 is a plot illustrating another example waveform 68 representing an example series of electrical stimulation pulses for delivery to patient 16. In particular, waveform 68 includes first stimulation pulse 70a, second stimulation pulse 70b, third stimulation pulse 70c, fourth stimulation pulse 70d, fifth stimulation pulse 70e, sixth stimulation pulse 70f, seventh stimulation pulse 70g, and eighth stimulation pulse 70h (partially shown) (collectively "series of stimulation pulses 70"). IMD 12 may generate and deliver gastric electric stimulation to stomach 22 of patient 16 via electrodes 24 and 26 carried on leads 18 and 20 respectively, where the gastric electric stimulation includes the series of electrical stimulation pulses 70 represented by waveform 68. In some examples, such electric stimulation may effectively treat one or more patient conditions, e.g., by increasing the distension of stomach 22 of patient 16. Although series of stimulation pulses 70 represented by waveform 68 are shown to include eight stimulation pulses 70a-h, the gastric electric stimulation generated and delivered to patient 16 by IMD 12 may include any number of stimulation pulses that provide effective treatment to patient 16.

As represented by waveform 68, IMD 12 delivers stimulation pulses 70a-h in direct succession with one another. Each of stimulation pulses 70a-d have the same polarity (all cathodic or all anodic), and each of stimulation pulses 70e-h have the same polarity, which is opposite from that of the polarity of pulses 70a-d. As shown in FIG. 7, similar to that of waveform 60 (FIG. 5), each of pulses 70a-d is followed substantially immediately by pulses 70e-h, respectively. However, unlike waveform 60 (FIG. 5), in some examples, the pulse width of each of pulses 70e-g in waveform 68 (FIG. 7) is such that each pulse 70e-g is followed substantially immediately by pulses 70b-d, respectively. In such examples, IMD 12 delivers series of pulses 70 to patient 16 such that there is substantially no time interval between each successive pulse. Furthermore, unlike that of waveform 60 (FIG. 5), the amplitude of pulses 70a-d is different than that of the amplitude of pulses 70e-h. In particular, as shown in FIG. 7, the amplitude of pulses 70a-d is greater than that of pulses 70e-h.

Similar to that of the series of pulses 62 of waveform 60 (FIG. 5), in some examples, the series of stimulation pulses 70 is a plurality of pulses including pairs of individual pulses that are coupled to one another. In particular, first pulse 70a is coupled with fifth pulse 70e, second pulse 70b is coupled with sixth pulse 70f, third pulse 70c is coupled with seventh pulse 70g, and fourth pulse 70d is coupled with eighth pulse 70h. As such, the temporal relationship between each pulse of a couple pair of pulses is fixed. In the example shown in FIG. 7, the temporal relationship between each pulse of coupled pairs of pulses (e.g., pulses 70a and 70e, pulses 70b and 70f, and so forth) is such that the second pulse of the coupled pair (e.g., pulses 70e, 70f, 70g, and 70h) is delivered substantially immediately after the first pulse of the coupled pair (e.g., pulses 70a, 70b, 70c, and 70d, respectively) ends. In some examples, a fixed time delay may separate respective pulses of a coupled pair of pulses. For example, there may be a fixed delay of approximately 10 microseconds to approximately 100 microsecond between pulse 70a and pulse 70e. Such a fixed delay may be the same for each coupled pulse pair.

In some examples, series of pulses 70a-h may be substantially charged balanced. For example, first pulse 70a may have an equal and opposite charge from that of fifth pulse 70e. Notably, first pulse 70a and fifth pulse 70e may be charged balanced even though the amplitude of first pulse 70a is greater than that of fifth pulse 70e. To achieve substantial charge balance, the pulse width PW12 of fifth pulse 70e may be selected such that fifth pulse 70e extends from the trailing edge of first pulse 70a to the leading edge of second pulse 70b. Such timing may depend on the interval of time T(12) between start of first pulse 70a and second pulse 70b, in addition to the pulse width PW11 of first pulse 70a. The amplitude of fifth pulse 70e may be selected such that fifth pulse 70e has substantially the same charge as first pulse 70a when having a pulse width PW12. In such as case, fifth pulse 70e may have approximately the minimum amplitude allowed to maintain charge balance with first pulse 70a. For example, the area between the amplitude curve and the zero amplitude line for a first pulse 70a is approximately equal to the area between the amplitude curve and the zero amplitude line for the fifth pulse 70e.

In some examples, the difference in amplitude (current amplitude or voltage amplitude) of pulses 70a-d and pulses 70e-f may be such that the influence that the delivery of pulses 70a-d has on tissue at the target site is different than that of the influence that pulses 70e-f has on the same tissue at the target site. For example, pulses 70a-d may have a pulse amplitude that provides a pulse energy that is above the threshold required to depolarize one or more cells at the target tissue site, while pulses 70e-g, which have a lower pulse amplitude from that of pulses 70a-d, may have a pulse amplitude that provides a pulse energy that is below that threshold required to depolarize the cells at the target tissue site. In such a situation, pulses 70e-h may provide for charge balanced stimulation without interfering with the physiological response of tissue to pulses 70a-d. By selecting the pulse width of pulse 70e-h to extend substantially from the end of the directly preceding pulse to the beginning of the following pulse, the amplitude of pulse 70e-h is minimized while still allowing series of pulses 70a-h to be substantially charged balanced. In some examples, there may be a time delay between the second pulse of a coupled pair and the first pulse of the next coupled pair, e.g., between pulses 70e and 70b, although in such a case, the amplitude of pulse 70e is not minimized as described for some examples.

IMD 12 may deliver the series of pulses represented by waveform 68 to patient 16, e.g., to stomach 22, according to any suitable value for each of pulse width, pulse amplitude, and pulse frequency. In some examples, one or more of the stimulation parameters may be selected such that the electrical stimulation delivered by IMD 12 to stomach 22 of patient 16 causes the distension of stomach 22 to increase. In some examples, for constant current applications, pulses 70a-d may have a pulse amplitude greater than zero but less than or approximately equal to 25.0 milliamps, such as, e.g., a pulse amplitude between approximately 1 milliamp and approximately 12.0 milliamps, or between approximately 2 milliamps and approximately 25 milliamps. In some examples, for constant voltage applications, pulses 70a-d may have a pulse amplitude greater than zero but less than or approximately equal to 25.0 volts, such as, e.g., a pulse amplitude between approximately 1 volt and approximately 12.0 volts, or between approximately 2 volts and approximately 25 volts. Constant current and constant voltage applications refer to applications in which the current or voltage, respectively, is regulated or controlled to provide a desired level which could be constant or could be shaped, although in most cases the pulse may have a constant current or voltage. In some examples, pulses 70a-d may have a pulse width between approximately 0.05 milliseconds and approximately 1000 milliseconds, such as, e.g., between approximately 0.5 milliseconds and approximately 50 milliseconds. In some examples, pulses 66a-d may have a pulse width between approximately 0.5 milliseconds and approximately 20 milliseconds, such as, e.g., between approximately 1 millisecond and approximately 20 milliseconds. In other examples, pulses 70a-d may have a pulse width between approximately 0.1 milliseconds and approximately 20 milliseconds, such as, e.g., between approximately 1 millisecond and approximately 20 milliseconds. In some examples, pulses 70a-d may be delivered at a pulse frequency between approximately 0.05 Hz and the approximate value determined by dividing 1000 by 2 times the pulse width (in milliseconds) Hz, such as, e.g., between approximately 0.5 Hz and the approximate value determined by dividing 1000 by 2 times the pulse width (in milliseconds) Hz. In some examples, pulses 70a-d may be delivered at a pulse frequency between approximately 0.05 Hz and approximately 40 Hz, such as, e.g., between approximately 1 and approximately 40 Hz. In examples in which IMD 12 deliver electrical stimulation including series of pulse 70a-d according to duty cycle, electrical stimulation may "on" between approximately 5% and approximately 100% of the time. Other values for each electrical stimulation parameters are contemplated. In each case, IMD 12 may generated and deliver electrical stimulation to patient 16 to cause substantial gastric distention and a sensation of fullness, which may result in reduced food intake and, ultimately, weight loss.

In some examples, such pulses may be delivered via a lead-borne electrode (e.g., as a cathode) and an IMD housing electrode (can electrode) (e.g., as an anode) in a unipolar arrangement, or between bipolar or multipolar lead-borne electrodes. Furthermore, such pulses may be delivered as a continuous pulse train, or the pulses may be contained in periodic or aperiodic bursts of multiple pulses, or in periodic or aperiodic pulse burst envelopes containing multiple pulse bursts. The pulse bursts may be of the same duration or different durations. In some examples, IMD 12 may deliver electrical stimulation with a burst frequency between approximately 2 and approximately 15 bursts per minute. In some examples, IMD 12 may deliver bursts having a duration of between approximately 0.1 seconds and approximately 15 seconds.

Figure 8:
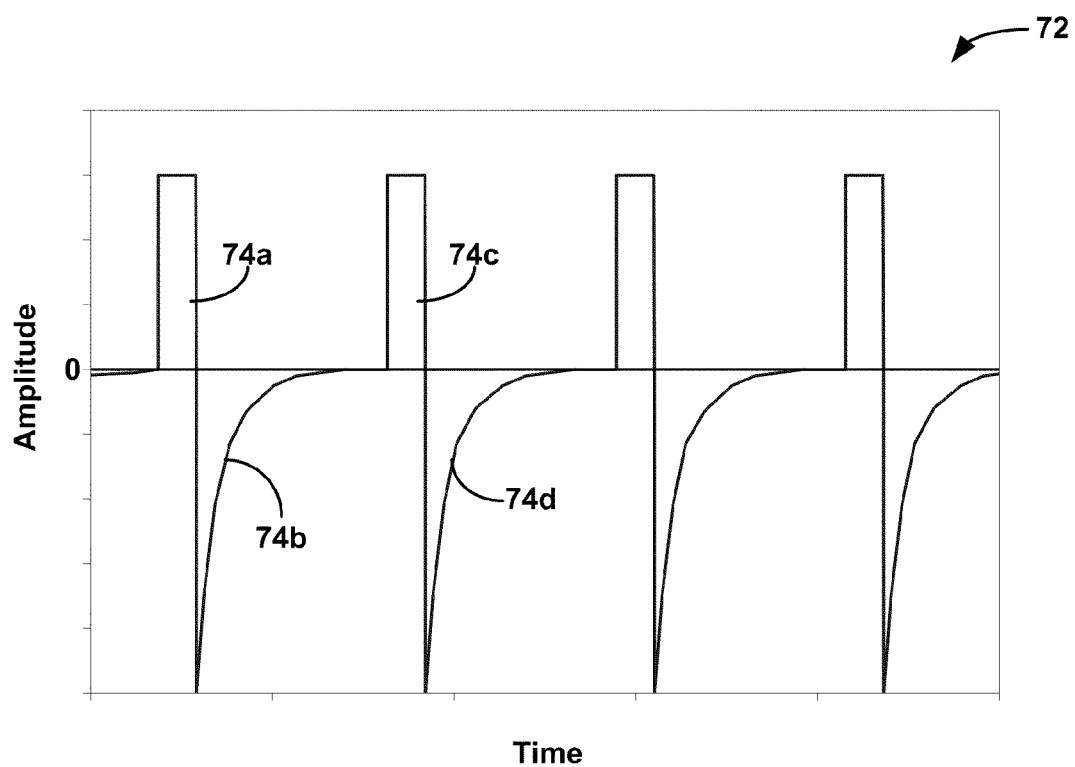
FIG. 8 is a plot illustrating another example waveform representing an example series of electrical stimulation for delivery to a patient.

FIG. 8 is a plot illustrating another example waveform 72 representing an example series of electrical stimulation pulses for delivery to patient 16. Waveform 72 includes first pulse 74a, second pulse 74b, third pulse 74c, and fourth pulse 74d, which are delivered in direct succession with one another. As shown, first pulse 74a and third pulse 74c are rectangular pulses, and second pulse 74b and fourth pulse 74d are hyperbolic pulses. First pulse 74a and third pulse 74c have opposite polarity from that of second pulse 74b and fourth pulse 74d. IMD 12 delivers second pulse 74b substantially immediately after the end of first pulse 74a. Third pulse 74c is delivered to be substantially non-overlapping with second pulse 74b.

In some examples, first pulse 74a and second pulse 74 are coupled pulse pairs and third pulse 74c and fourth pulse 74d are coupled pulse pairs. As such, the temporal relationship between the delivery of first pulse 74a and second pulse 74b does not change as the frequency of the delivery of pulses 74a and 74c is changed. In the example shown, the fixed time interval between coupled pair pulses, e.g., between first pulse 74a and second pulse 74b, is approximately zero. In other examples, there may be a fixed time delay between approximately 10 microseconds and approximately 100 microseconds.

First pulse 74a has an approximately equal and opposite charge of that of second pulse 74b. As such first and second pulses 74a and 74b may be considered charge balanced with one another. In some examples, the shape of second pulse 74b reflects the passive recharge of capacitors in which stimulation generator 28 (FIG. 2) accumulates the charge to be delivered in third pulse 74c. The exact shape of second pulse 74b may vary with the amount of charge delivered in the first and third pulses 74a and 74c, in addition to the characteristics of the one or more capacitors of stimulation generator 28.

Figure 9:
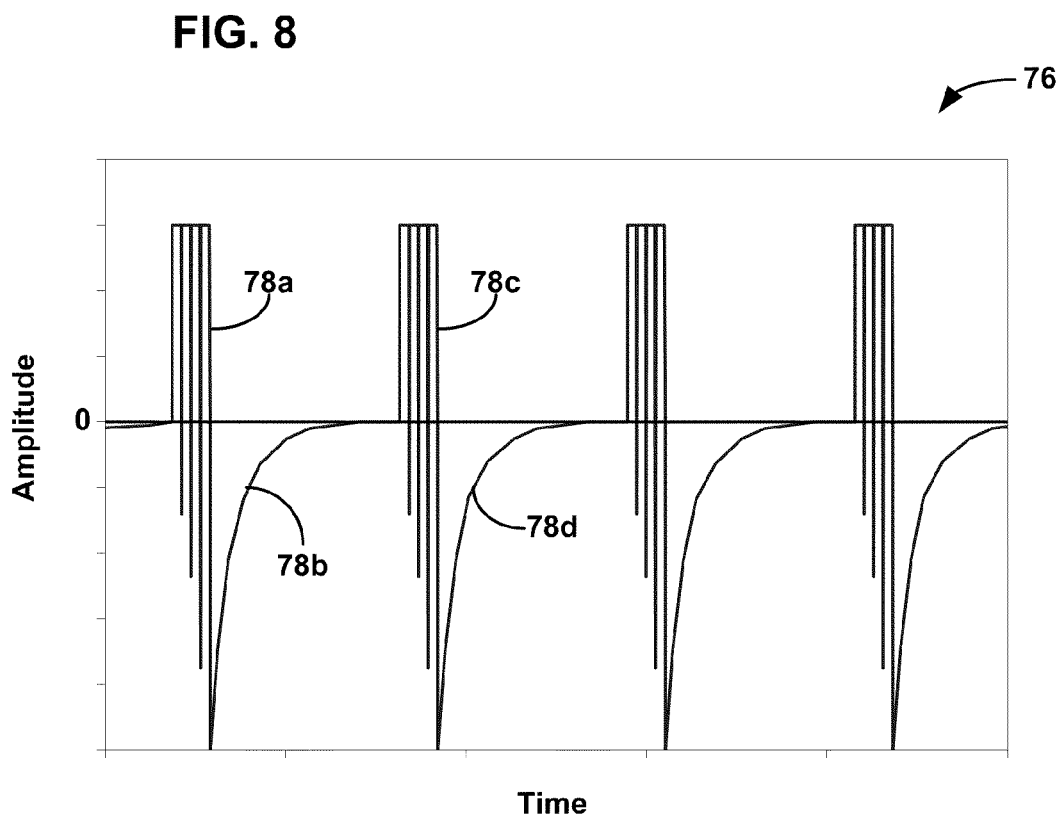
FIG. 9 is a plot illustrating another example waveform representing an example series of electrical stimulation for delivery to a patient.

FIG. 9 is a plot illustrating another example waveform 76 representing an example series of electrical stimulation pulses for delivery to patient 16. Waveform 76 includes first pulse 78a, second pulse 78b, third pulse 78c, and fourth pulse 78d, which are delivered in direct succession with one another. As shown, first pulse 78a and third pulse 78c are rectangular pulses, and second pulse 78b and fourth pulse 78d are hyperbolic pulses. First pulse 78a and third pulse 78c have opposite polarity from that of second pulse 78b and fourth pulse 78d. IMD 12 delivers second pulse 78b substantially immediately after the end of first pulse 78a. Third pulse 78c is delivered to be substantially non-overlapping with second pulse 78b.

In some aspects, waveform 76 is substantially the same as waveform 74 (FIG. 8). First and second pulses 74a and 74b may be considered charge balanced with one another. In some examples, the shape of second pulse 74b reflects the passive recharge of capacitors in which stimulation generator 28 (FIG. 2) accumulates the charge to be delivered in third pulse 74c. The exact shape of second pulse 74b may vary with the amount of charge delivered in the first and third pulses 74a and 74c, in addition to the characteristics of the one or more capacitors of stimulation generator 28. Furthermore, first pulse 78a and second pulse 78b may be a coupled pulse pair, and third pulse 78c and fourth pulse 78d may be a coupled pulse pair.

However, as shown in FIG. 9, first pulse 78a and third pulse 78c are each stacked pulses. The stacked pulses are a sequence of four rectangular pulses with small intervening gaps (e.g., between 10 to 50 microseconds). However, within each gap, a passive recharge may occur, which is apparent from the downward spikes in first pulse 78a and second pulse 74c. Such stacked pulses may be useful for stimulators including a stimulation generator that is not capable of generating a single pulse having the amplitude and pulse width of non-stacked rectangular stimulus phase pulse 74a (FIG. 8).

As described above, IMD 12 may deliver electrical stimulation to stomach 22 of patient 16 via electrodes 24 and 26 to treat a gastric disease or disorder. For example, IMD 12 may deliver electrical stimulation to patient 16 to produce one or more desirable conditions in patient 16 to treat the patient disease or disorder. The electrical stimulation delivered by IMD 12 to stomach 22 may include a series of pulses, such as, e.g., the series of pulse 66 that are represented by waveform 64 (FIG. 6A) and/or the series of pulses 70 that are represented by waveform 68 (FIG. 7). As will be illustrated in the below examples, the delivery of electrical stimulation using waveform 64 and/or waveform 68 may effectively induce distension of stomach 22 or, more generally, distension of one or more organs of the GI tract.

IMD 12 may be configured to deliver electrical stimulation including series of pulses 66 of waveform 64 and/or series of pulse 70 of waveform 68 on any suitable basis. For example, IMD 12 may generate and deliver electrical stimulation using waveform 64 or waveform 68 to stomach 22 of patient 16 on a substantially continuous basis. In such an example, IMD 12 may generate and deliver a plurality of pulses to stomach 22 on a continuous basis once stimulation has been activated.

Alternatively or additionally, IMD 12 may generate and deliver electrical stimulation using waveform 64 or waveform 68 on a cycling basis. In such an example, IMD 12 may generated and deliver a plurality of pulses to stomach 22, where the output is automatically gated on and off in a repeating pattern when the stimulation has been activated. In some examples, the "on" time may range from about 0.01 seconds to about 168 hours, and the "off" time may range from about 0.01 seconds to about 168 hours. In some examples, the electrical stimulation may be "on" approximately 5% to approximately 100% of time.

IMD 12 may be activated for delivery of electrical stimulation, e.g., on a continuous or cycling basis, using any suitable technique. In some examples, IMD 12 may be manually activated for electrical stimulation therapy by a user (e.g., patient 16) via programmer 14 (FIG. 1). In other examples, IMD 12 may be automatically or semi-automatically activated for electrical stimulation therapy. For example, IMD 12 may be activated for delivery of electrical stimulation therapy based on one or more physiological parameters (e.g., blood pressure, heart rate, blood flow, pH, and the like) the may be useful as direct or indirect indicators of appropriate times to deliver gastric electrical stimulation therapy. Stimulation 12 may monitor the one or more physiological parameters via one or more physiological sensors implanted within or external to patient 16.

IMD 12 may use the monitored physiological parameter to determine when to activate and deactivate the electrical stimulation. For example, IMD 12 may automatically activate electrical stimulation when the value of a monitored physiological parameter falls above or below a predefined threshold. Once activated, IMD 12 may remain active for a predefined period of time and/or until the value of the monitored physiological parameter fulfills some predefined benchmark. Alternatively or additionally, IMD 12 may use the monitored physiological parameter to modulate one or more electrical stimulation parameters on a closed loop basis. For example, processor 30 of IMD 12 may modify pulse amplitude, pulse width, pulse frequency, or the duration of stimulation according to the value of a sensed physiologic parameter.

In some examples, IMD 12 may deliver electrical stimulation using waveform 64 or waveform 68 on a scheduled basis. For example, memory 32 may store information regarding one or more pre-programmed schedules. Processor 30 may access the schedule information stored in memory 32 to determine when to generate and deliver electrical stimulation therapy to patient 16. Such schedule information may define certain times or time periods during which electrical stimulation should be active. In some examples, one or more active time periods may be programmed to correspond to times that patient 16 generally to eats a meal, so that IMD 12 may deliver electrical stimulation using waveform 64 or waveform 68 to induce increased distension of stomach to produce the feeling of fullness in patient 16. For example, IMD 12 may be configured to deliver electrical stimulation therapy delivery during time periods corresponding to ordinary breakfast, lunch and dinner times, as well as snack times, if necessary. A therapy window specifying the maximum continuous time for which stimulation may be delivered may be placed at different temporal positions within such a time period. In some examples, memory 44 of programmer 14 may store schedule information and processor 40 may communicate with IMD 12 via telemetry interface 50 to active and deactivate electrical stimulation therapy according to the pre-programmed schedule.

In some examples, IMD 12 may generate and deliver electrical stimulation using one or more of the waveforms described herein, e.g., waveform 64 or waveform 68, to a single target tissue site of patient 16 of a GI tract organ. In other examples, IMD 12 may generate and deliver electrical stimulation using waveform 64 or waveform 68 to multiple target tissue sites. Different electrode combinations may be used to deliver electrical stimulation to different target tissue sites. The electrodes for each combination may be carried on the same lead or different leads. The multiple target tissue sites may include two or more tissue sites on the same organ of the GI tract (e.g., as shown in FIG. 4B) or may include one or more tissue sites on two or more organs of the GI tract. In some examples, IMD 12 may deliver substantially the same electrical stimulation to each site (e.g., electrical stimulation having substantially the same stimulation parameters for each tissue site as defined by a therapy program). In other examples, IMD 12 may deliver different electrical stimulation to different target tissue sites. For example, IMD 12 may deliver electrical stimulation to a first target tissue site using a first waveform, and may deliver electrical stimulation to a second target tissue site using a second waveform.

In some cases, the electrical stimulation therapies delivered to different tissue sites are configured to produce a substantially identical therapeutic result, such as promotion of gastric distention, nausea or discomfort to discourage food intake by a patient. In other words, each electrode combination delivers stimulation with parameters selected to produce substantially the same therapeutic result, such as gastric distention. In other examples, the electrical stimulation therapy provided to different tissue sites may be configured to produce different therapeutic results.

As described, IMD 12 may deliver electrical stimulation using one or more example waveforms described herein to provide effective treatment for obesity. In such cases, prior to the delivery of electrical stimulation therapy using such waveforms or even the implantation of IMD 12 and/or leads 18 and 20 within patient 16, a clinician may identify patient 16 as being obese using any suitable technique. For example, the clinician may identify the patient as being obese based at least in part on the weight of patient 16. Based on the identification of patient 16 as obese, IMD 12 and lead 18 and 20 may be implanted in patient 16 to deliver electrical stimulation using one or more of the example waveform described herein to treat the patient obesity.

While example waveforms, such as, example waveforms 60, 64, 65, and 68 are shown to include substantially rectangular pulses, examples should are not limited to such pulse shapes but may include any suitable shape. In some examples, the pulses may include some decline from the leading edge to the trailing edge of each stimulus phase. Such pulse "droop" is may be present in some implantable pulse generators, and can be compensated for by increasing pulse amplitude to the point where the trailing edge amplitude equals that of the constant amplitude rectangular pulse being emulated.

Figure 10:
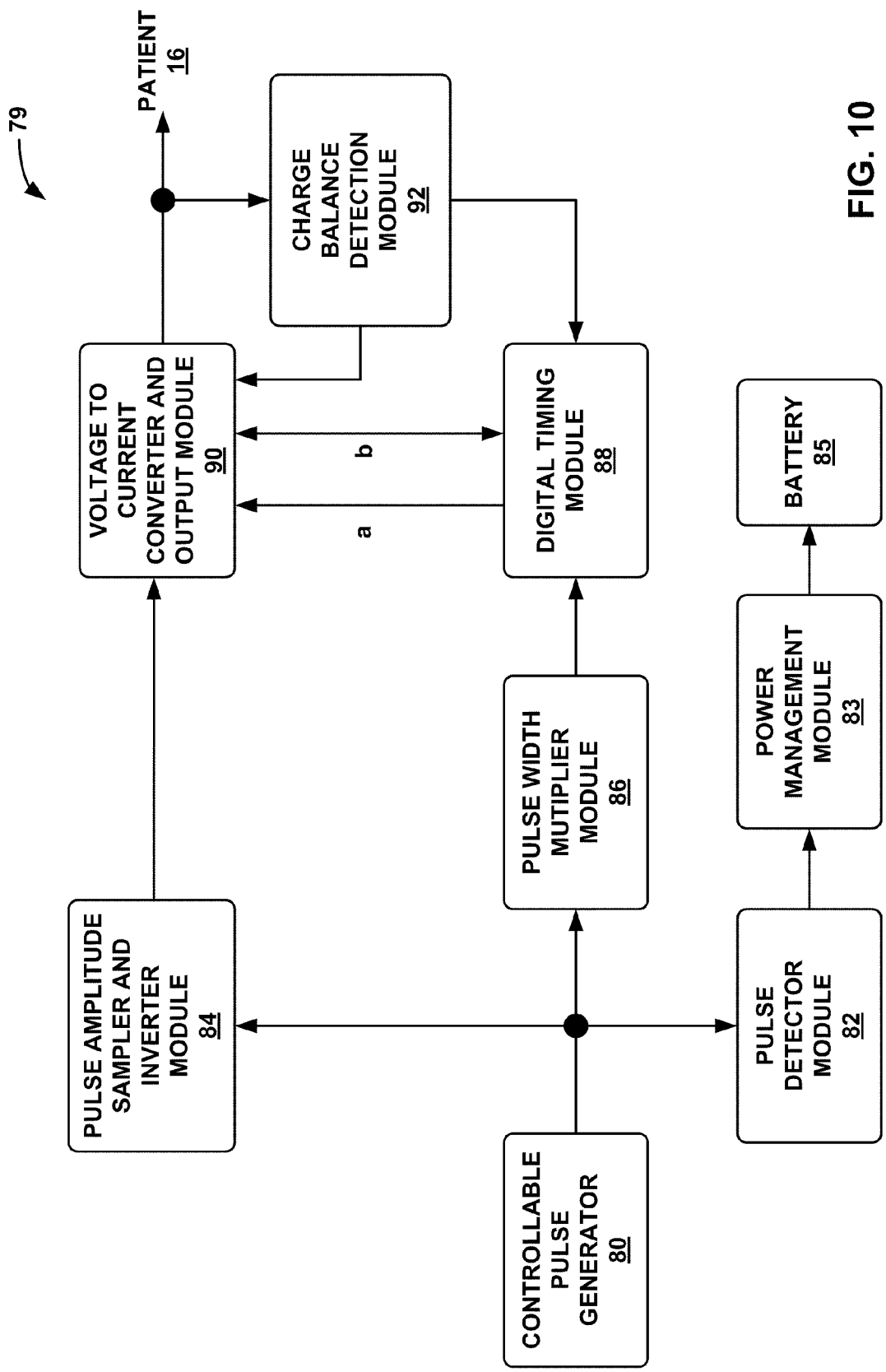
FIG. 10 is a block diagram illustrating an example stimulation generator for delivery of electrical stimulation therapy.

FIG. 10 is a block diagram of an example stimulation generator 79 that may be used to generate and deliver electrical stimulation therapy using one of more of the waveforms described in this disclosure. Stimulation generator 79 includes controllable pulse generator 80, pulse detector module 82, power management module 83, pulse amplitude sampler and inverter module 84, battery 85, pulse width multiplier module 86, digital timing module 88, voltage to current converter and output module 90, and charge balance module 92. The various components of FIG. 10 may be formed by any of a variety of discrete and/or integrated electrical circuitry, including logic circuitry such as one or more microprocessors, application specific integrated circuits (ASICs), field programmable gate arrays (FPGAs), or the like, or any combination of such circuitry.

Controllable pulse generator 80 generates an electrical signal waveform, which may comprise a series of pulses with a controlled pulse amplitude, pulse frequency, and pulse width. In some examples, controllable pulse generator 80 may be a stimulation generator that is not capable of generating one or more pulses with the particular morphology desired for delivery to patient 16, e.g., based on the desired pulse width. As will be described below, in some examples, controllable pulse generator 80 may include a Medtronic Restore implantable pulse generator, manufactured by Medtronic, Inc. of Minneapolis, Minn., USA. As will be apparent from the following description, the parameters of the pulse train generated by controllable pulse generator 80 may be used to control the pulse width, pulse frequency, and pulse amplitude of the pulses generated by converter and output module 90.

The electrical signal waveform generated by controllable pulse generator 80 propagates to pulse detector module 82, pulse width multiplier module 86, and pulse amplitude sampler and inverter module 84. Power management module 83 may include power supply circuitry that generates one or more regulated supply voltages from power provided by battery 85. Power management module 83 may provide power to various components of stimulation generator 79 of FIG. 10, including voltage to current converter and output module 90. Pulse detector module 82 may include a pulse detector that detects pulses generated by controllable pulse generator 80. If pulse detector module 82 does not detect pulses from controllable pulse generator 80, then pulse detector module 82 may control power management module 83 to turn off power to one or more components of stimulation generator 79, such as voltage to current converter and output module 90, or enter a power conservation mode.

Pulse amplitude sampler and inverter module 84 detects the pulses generated by controllable pulse generator 80. Controllable pulse generator 80 generates the pulses with a specific pulse amplitude value, pulse width, and frequency, which may be selected by a user such as a physician or patient using an external programmer such as a patient programmer or physician programmer. Pulse amplitude sampler and inverter module 84 may sample and measure the amplitude of the pulses generated by controllable pulse generator 80, and output a control signal and an inverted version of the control signal. The non-inverted and inverted control signals may have amplitude values proportional to the amplitude of the pulses generated by controllable pulse generator 80. In particular, based on the measured amplitude, pulse amplitude module 84 may generate non-inverted and inverted analog voltage signals which are received by voltage to current converter and output module 90 indicating the measured pulse amplitude.

Voltage to current converter and output module 90 receives the analog voltage signals from pulse amplitude sampler and inverter module 84, and selectively converts one of the voltage signals into current to generate a current pulse for delivery to patient 16. Digital timing module 88 controls voltage to current converter and output module 90 to output either a positive current pulse based on the non-inverted voltage signal or a negative current pulse based on the inverted voltage signal. For the example of an alternating monophasic waveform, e.g., as described with reference to FIG. 6, timing module 88 may control voltage to current converter and output module 90 to deliver positive and negative pulses on an alternating basis.

The amplitude of the current pulse is proportional to the amplitude of the inverted or non-inverted voltage signal, as applicable, that is provided by pulse amplitude sampler and inverter module 84. In turn, the amplitude of inverted or non-inverted voltage signal is proportional to the amplitude of the pulse obtained from controllable pulse generator 80. The pulse generated by controllable pulse generator 80 serves to control the current pulse generated by voltage to current converter and output module 90, which may act as a transconductance amplifier to convert voltage to current. As an illustration, if the amplitude of the pulse generated by pulse generator 80 is x volts, pulse amplitude sampler and inverter module 84 may generated inverted and non-inverted voltages representative of voltage level x. If the gain of voltage to current converter and output module 90 is y, then the output current pulse amplitude may be x*y amps.

As discussed above, module 90 generates electrical stimulation pulses with a pulse amplitude value that is defined based on the level of the analog voltage signal from pulse amplitude sampler and inverter module 84. Again, the level of the analog signal from pulse amplitude module 84 is proportional to the amplitude of the pulse from controllable pulse generator 80, which may be a controlled current or controlled voltage pulse. In this manner, the pulse amplitude (e.g., voltage pulse amplitude) generated by controllable pulse generator 80 may be used to specify the amplitude of a corresponding pulse (e.g., current pulse amplitude) to be generated by voltage to current converter and output module 90.

While pulse amplitude sampler and inverter module 84 controls the amplitude of the pulses to be delivered by voltage to current converter and output module 90, pulse width multiplier module 86 may determine the pulse width and frequency of the pulses, in conjunction with digital timing module 88. Pulse width multiplier module 86 detects the pulses generated by controllable pulse generator 80 having a controlled pulse width. Pulse width multiplier 86 may be configured to determine the pulse width of the received pulse and multiply that pulse width by a preset value n (e.g., n=5). Pulse width multiplier 86 then transmits a signal to digital timing module 88 indicating the calculated pulse width. As an example, assuming that pulse width multiplier module 86 is configured to multiply the pulse width of the signal from controllable pulse generator 80 by five, pulse width multiplier 86 may transmit a signal to timing module 88 indicating a pulse width of 5 milliseconds upon the detection of a pulse generated by controllable pulse generator 80 having a pulse width of 1 millisecond.

Based on the pulse width value indicated by pulse width multiplier module 86, digital timing module 88 indicates to module 90 the timing for the delivery of pulses from module 90 to stomach 22. For example, the timing may be expressed as a start and stop that defines a pulse width with a rising and falling edge. Timing module 90 also controls the polarity of the pulses delivered by module 90, e.g., by controlling the module to operate as either a current source or current sink. For a positive polarity pulse, for example, module 88 controls converter and output module 90 to operate as a current source using the non-inverted voltage from pulse amplitude sampler and inverter module 84 as an input signal. Conversely, for a negative polarity pulse, for example, module 88 controls converter and output module 90 to operate as a current sink using the in inverted voltage from pulse amplitude sampler and inverter module 84 as an input signal.

For the example of FIG. 6, digital timing module 88 may control output module 90 to deliver positive polarity pulses and negative polarity pulses on an alternating basis. To cause module 90 to deliver a positive pulse, module 88 may assert (e.g., enable or logic 1) and deassert (e.g., disable or logic 0) line a, where line a is asserted high for a period of time equal to the pulse width control signal generated by pulse width multiplier module 86 such that module 90 delivers the positive pulse for that period of time. To cause module 90 to deliver a negative pulse, module 88 may assert and deassert line b, where line a is asserted high for a period of time equal to the pulse width control signal generated by pulse width multiplier module 86 such that module 90 delivers the negative pulse for that period of time.

Module 90 may include parallel regulated current source and sink circuits that can be selectively activated to deliver positive and negative current pulses, respectively. The pulses may be delivered across a lead-borne electrode and an electrode of the IMD housing, in a unipolar arrangement, or between two or more lead-borne electrodes in a multipolar arrangement. As an example, the source or sink of module 90 may be selectively activated by digital timing module 88 using signals applied via lines a and b. Again, the time for which a source or sink is activated may be a function of the pulse width indicated by pulse width multiplier module 86, which scales up the pulse width of the pulse generated by pulse generator 80 to provide a longer pulse width. Although the output of module 90 is described as current pulses for purposes of illustration, in some examples, stimulator generators applying principles of this disclosure may alternatively deliver voltage pulses.

Charge balance module 92 may be provided to monitor the output of module 90 to determine that the charge of the pulses delivered from module 90 to stomach 22 is substantially balanced. For example, charge balance module 92 may detect a voltage across one of more output capacitors of module 90 to determine whether a charge imbalance remains following delivery of a stimulation pulse. Upon delivering a positive polarity pulse, for example, it may be desirable to restore the output voltage to a reference voltage, such as zero volts. For some waveforms, charge balance module 92 may transmit a signal to digital timing module 88 to indicate instances of imbalanced charge, and cause digital timing module 88 to adjust the pulse width of a negative polarity pulse such that it is truncated or shortened to provide a substantial charge balance with respect to a positive polarity pulse. In this case, digital timing module 88 may control pulse width based on the input of module 86 and module 92.

For other waveforms, charge balance module 92 may transmit a signal to module 90 to indicate instances of imbalanced charge and cause module 90 to reduce or increase an amplitude of the a negative polarity pulse such that it is increased or decreased to provide a substantial charge balance with respect to a positive polarity pulse. For some waveforms, charge balance module 92 may control both digital timing module 88 and module 90 to adjust pulse width and amplitude of a negative polarity pulse to provide a substantial charge balance with respect to a positive polarity pulse.

Stimulation generator 79 is only one example of a stimulation generator that may be used to generate and deliver stimulation pulses to a patient in a manner consistent with one or more waveforms described in this disclosure. Other example stimulation pulse generators capable of generating and delivering pulses with the desired morphology are contemplated. In other examples, a current regulator may be controlled to operate as a regulated current source or sink and to deliver current pulses with desired polarity, frequency and pulse width to provide any of the waveforms described in this disclosure. Alternatively, a voltage-based stimulation generator may be provided in other examples to delivery controlled voltage pulses instead of controlled current pulses. Accordingly, the example arrangement of FIG. 10 is provided for purposes of illustration as one example of the convenient use of a controllable pulse generator with one set of capabilities (such as pulse width) to drive and control another pulse generator to provide another set of capabilities (e.g., larger pulses widths). In the example of FIG. 10, the first pulse generator 80 has parameters that are controlled to, in turn, control the components of stimulation generator 79 as described. However, a single pulse generator (or multiple pulse generators provided for multiple electrodes) may be used. Therefore, the example of FIG. 10 should not be considered limiting of the disclosure.

The techniques described in this disclosure may be implemented in hardware, software, firmware or any combination thereof. For example, various aspects of the techniques may be implemented within one or more microprocessors, digital signal processors (DSPs), application specific integrated circuits (ASICs), field programmable logic arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions are executed to support one or more aspects of the functionality described in this disclosure.

EXAMPLES

Example 1

An experiment was undertaken to evaluate three different example waveforms by delivering three types of gastric electric stimulation (GES), each according to a different example waveform, to lean canines and then observing the results that electrical stimulation produced. For the experiment, platinum-iridium stranded wire electrodes were implanted in the muscularis of distal gastric antrum of five lean mongrel dogs. A gastric cannula was also implanted for balloon barostat measurements of gastric volume. Percutaneous lead wires and an external pulse generator were used to deliver gastric electrical stimulation using three different waveforms. The first waveform (referred to as "Waveform 1") was consistent with the example waveform illustrated in FIG. 6A. The second waveform (referred to as "Waveform 2") was consistent with the example waveform illustrated in FIG. 5. The third waveform (referred to as "Waveform 3") was consistent with the example waveform illustrated in FIG. 7. The pulse widths of the pulses of Waveforms 1 (e.g. PW3 of first pulse 66a) and the first pulses of Waveforms 2 and 3 (e.g., PW1 of first pulse 62a and PW11 of first pulse 70a, respectively) were fixed at approximately four milliseconds. Pulses for Waveform 1 were administered continuously at a frequency of approximately 40 hertz. Pulses of similar polarity for Waveforms 2 and 3 (e.g., pulses 62a-d and pulses 70a-d, respectively) were administered continuously at a frequency of approximately 40 hertz. There was substantially no time delay between the first and second pulses of the coupled pulse pairs in Waveforms 2 and 3. Pulse amplitude (e.g., the amplitude of first pulses 66a, 62a, and 70a) for each waveform was fixed across treatments for each dog at the highest asymptomatic level less than or equal to six milliamps determined during symptom testing conducted on a separate day prior to barostat testing. All pulses were delivered using a DS8000 pulse generator and DLS100 linear stimulus isolator (both available from World Precision Instruments, Sarasota, Fla.).

During testing, each dog received: 1) electrical stimulation using Waveform 1; 2) electrical stimulation using Waveform 2; and 3) electrical stimulation using Waveform 3. The electrical stimulation for each waveform was delivered on separate occasions. Three, forty-minute balloon barostat recordings of gastric volume—one for each waveform—were made in each dog. Measurements were made on separate days with the dogs in a fasted state, and consisted of a 10 minute baseline recording, followed by 10 minutes of recording during the delivery of gastric electrical stimulation (GES), and 10 minutes of recording after stimulation was shut off. Treatments were administered in one of three randomly assigned orders to control for test order effects. Barostat balloon volumes were recorded at a frequency of one hertz, yielding 1800 measurements per 30 minute testing session. These measurements were analyzed using a repeated measures model allowing for the dependence of volume recordings over time within each dog. Model estimates were used to test for differences in changes in mean balloon volume from baseline levels across treatments.

Figure 11:
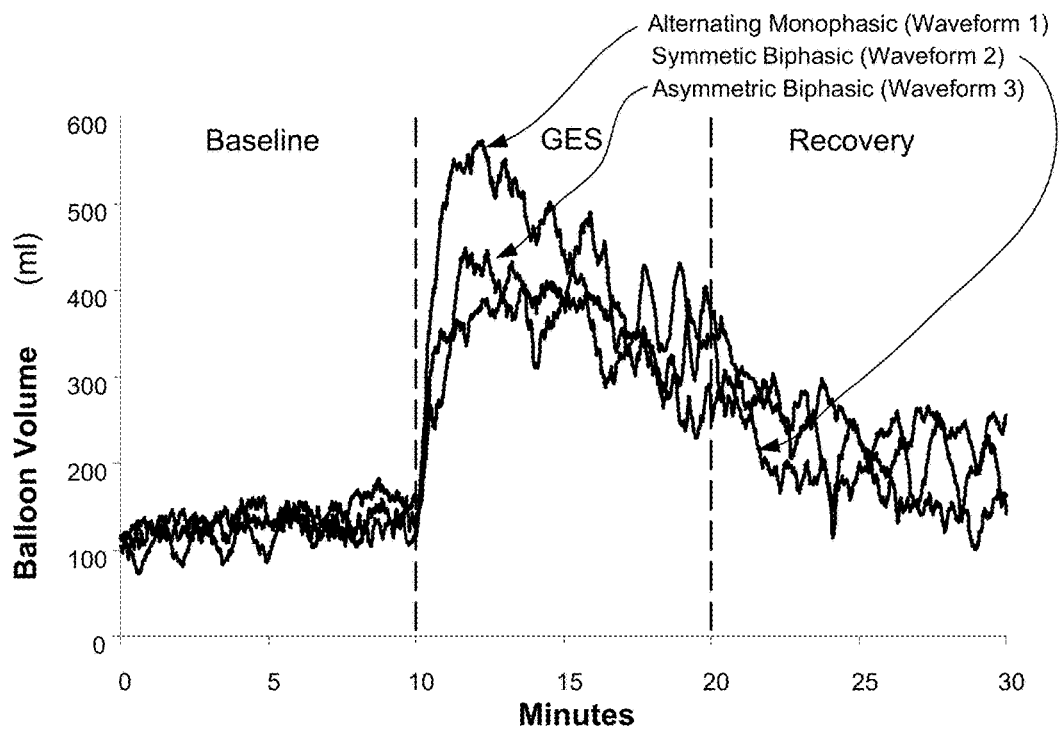
FIG. 11 is a plot illustrating measured barostat balloon volume versus time for example gastric electric stimulation (GES) using various example waveforms.

FIG. 11 is a plot illustrating measured barostat balloon volume versus time for each of Waveform 1-3. Each plotted value is the average of gastric barostat balloon volume measurements at a given time point across five sample dogs. As shown, the electrical stimulation using Waveform 1 produced larger increases in fasted gastric volume than either the electrical stimulation using Waveform 2 or the electrical stimulation using Waveform 3. The mean barostat balloon volume across the five sample dogs was higher at nearly every time point during the stimulation and recovery periods of the Waveform 1 stimulation testing sessions than during either testing sessions for the Waveform 2 stimulation and Waveform 3 stimulation.

Figure 12:
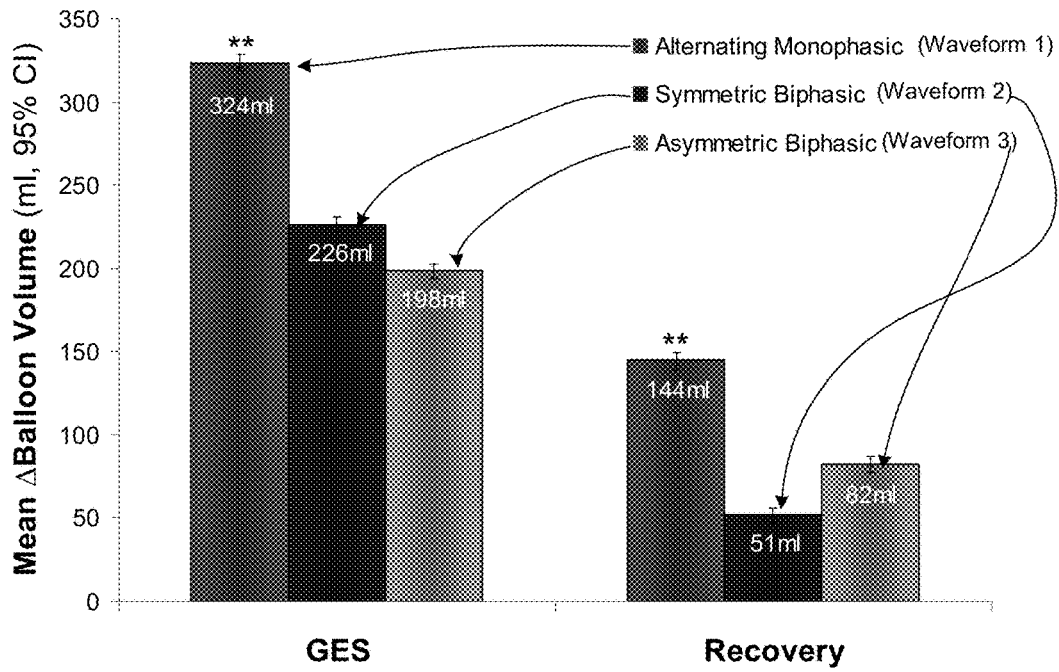
FIG. 12 is a plot illustrating mean change in barostat balloon volume during the delivery of example gastric electric stimulation (GES) and during the 10 minute recovery period for various experimental stimulation conditions.

FIG. 12 is a plot illustrating mean change in barostat balloon volume during the delivery of gastric electric stimulation (GES) and during the 10 minute recovery period for each of Waveforms 1-3. As shown, during the 10-minute active stimulation period, mean barostat balloon volume rose by approximately 324 milliliters from baseline levels under Waveform 1 stimulation, compared to approximately 226 milliliters and approximately 198 milliliters under Waveform 2 and Waveform 3 stimulation, respectively. The increase in balloon volume from basal levels was also larger during the post-stimulation recovery period following Waveform 1 stimulation than after either Waveform 2 or Waveform 3 stimulation (144 milliliters vs. 51 milliliters or 82 milliliters, respectively). During both the active stimulation and recovery periods, the volume-increase effectiveness advantage of Waveform 1 stimulation over either Waveform 2 or Waveform 3 stimulation was statistically significant ($p<0.0001$).

The GES-induced gastric distension reflected in increased barostat balloon volume has been found to activate neurons in brain nuclei linked to satiation and is one likely mechanism by which GES reduces food intake. Barostat-measured increases in gastric volume induced by GES have previously been found to be predictive of food intake responses to GES in canines, with larger GES-induced increases in gastric volume being associated with larger GES-induced reductions in feeding.

Example 2

An experiment was undertaken to evaluate Waveform 1 stimulation versus Waveform 3 stimulation with regard to food intake in lean dogs. Platinum-iridium stranded wire electrodes were implanted in the muscularis of the distal gastric antrum of five lean mongrel dogs, and externalized percutaneously on the dog's backs for connection to an external pulse generator. The sample dogs were acclimated for two weeks to feed in their home cages for 60 minutes each day with alligator clip wires attached to their external lead wires. A surplus of dry dog chow was provided during each feeding. After acclimation, the dogs entered a 3×3 Latin Square cross-over experiment in which each dog received four days of each of three comparison treatments during daily feedings in a randomly assigned sequence. Each treatment period was separated from the next by a three day washout period, during which the dogs continued the experimental feeding schedule without treatment.

The three comparison treatments in the experiment were: 1) sham stimulation control, in which the dogs were attached to the pulse generator but no stimulation was applied; 2) Waveform 1 stimulation; and 3) Waveform 3 stimulation. The pulse width, pulse amplitude and pulse frequency for Waveform 1 and Waveform 3 were the same as that described in Example 1. Pulses were administered continuously approximately 10 minutes prior to feeding. Stimulation was delivered using a World Precision Instruments DS8000 pulse generator and DLS100 linear stimulus isolators (World Precision Instruments, Sarasota, Fla.). Food intake was measured daily by weighing the food prior to feeding and weighing the residual food after feeding. The experiment generated a total of 60 daily observations on food intake, which were analyzed using a repeated measures regression including fixed treatment, dog, and time period effects.

Figure 13:
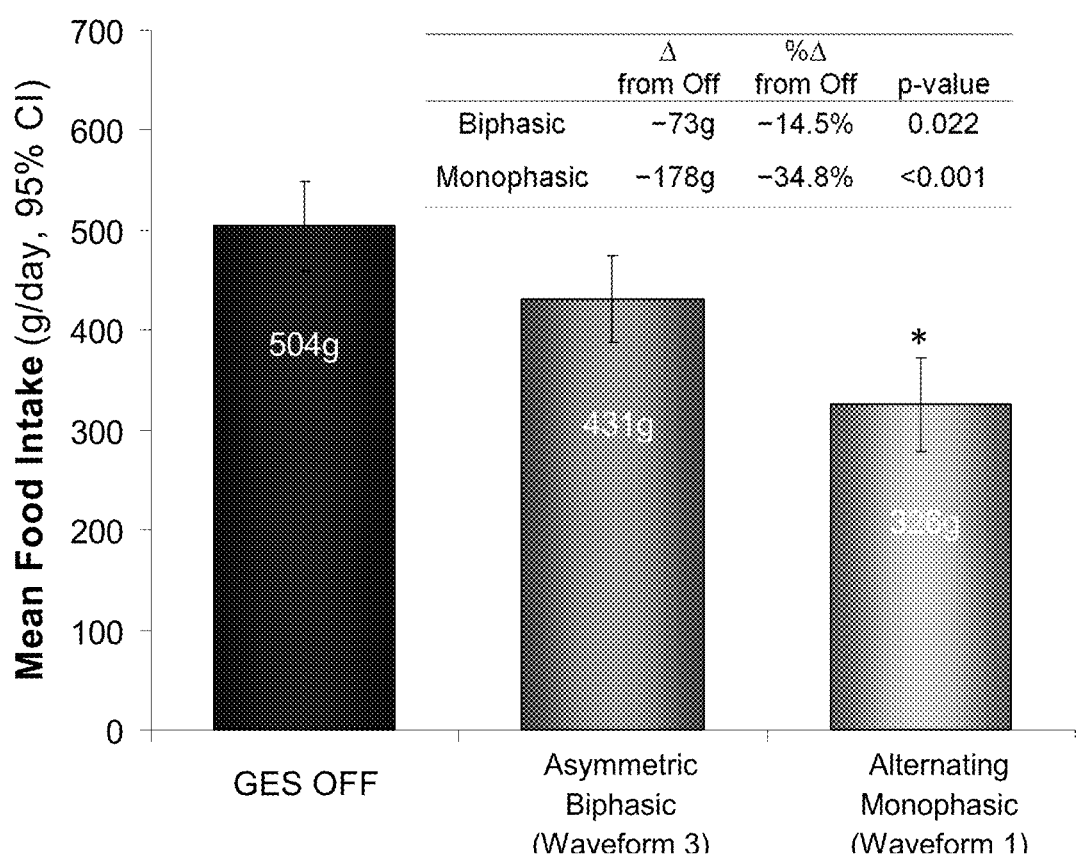
FIG. 13 is a plot illustrating measured mean food intake for various experimental conditions.

FIG. 13 is a plot illustrating the measured mean food intake for the GES-off period, the Waveform 1 stimulation period, and the Waveform 3 stimulation period. The values shown are least squares means from a repeated measures regression including fixed treatment, dog and time period effects. As shown in FIG. 13, mean daily food intake was reduced by approximately 178 grams or about 34.8% from the sham stimulation control level under the Waveform 1 stimulation treatment ($p<0.001$) and by approximately 73 grams or about 14.5% under the Waveform 3 stimulation treatment ($p=0.022$). The reduction in food intake was significantly greater ($p<0.001$) under the Waveform 1 stimulation treatment than under the Waveform 3 stimulation treatment.

Example 3

An experiment was undertaken to evaluate Waveform 1 stimulation versus Waveform 2 stimulation versus Waveform 3 stimulation with regard to food intake in obese rats. For the experiment, one pair of stranded, 0.2 mm diameter, platinum-iridium wire electrodes were implanted in the muscularis of the gastric antrum of 19 obese male Sprague-Dawley rats (aged 16-17 weeks, mean weight: approximately 551 grams, range: approximately 512-571 grams). Lead wires were externalized on the rats' backs for connection to an external pulse generator. The sample rats were of a diet induced obesity prone phenotype and were conditioned to obesity with 6 weeks of 24 hour ad libitum access to a standardized high fat diet (Research Diets D12451, 45% of kcal from fat). After surgical recovery, the rats underwent 21 days of conditioning to a restricted, two-hour-per-day feeding schedule in their home cages, followed by seven days of acclimation to feeding exclusively for two hours per day in a restrainer with alligator clip wires attached to their external lead wires. A surplus of high fat diet pellets was provided during each feeding period. The restrainers were used to limit each rat's movements enough to allow stimulation delivery during feeding.

Following conditioning to the restrainer feeding regimen, the sample rats entered a 4-week food intake experiment with a 4×4 Latin Square cross-over design. Each rat received 5 days of each comparison treatment during daily feedings in a randomly assigned order. Treatment periods were separated by two day washout periods. Treatments were: 1) sham stimulation control, under which the rats were attached to the pulse generator but no stimulation was applied; 2) Waveform 1 stimulation; 3) Waveform 2 stimulation; and 4) Waveform 3 stimulation. The pulse width and pulse frequency of Waveforms 1-3 were as described in Example 1, and the pulses were administered continuously. Pulse amplitude (e.g., the amplitude of first pulses 66a, 62a, and 70a) for each waveform was approximately six milliamps. All pulses were delivered using World Precisions Instruments DS8000 pulse generators and DLS100 linear stimulus isolators (World Precision Instruments, Sarasota, Fla.). Food intake was measured daily by weighing the food provided and the residual food remaining at the end of the two hour feeding.

Figure 14:
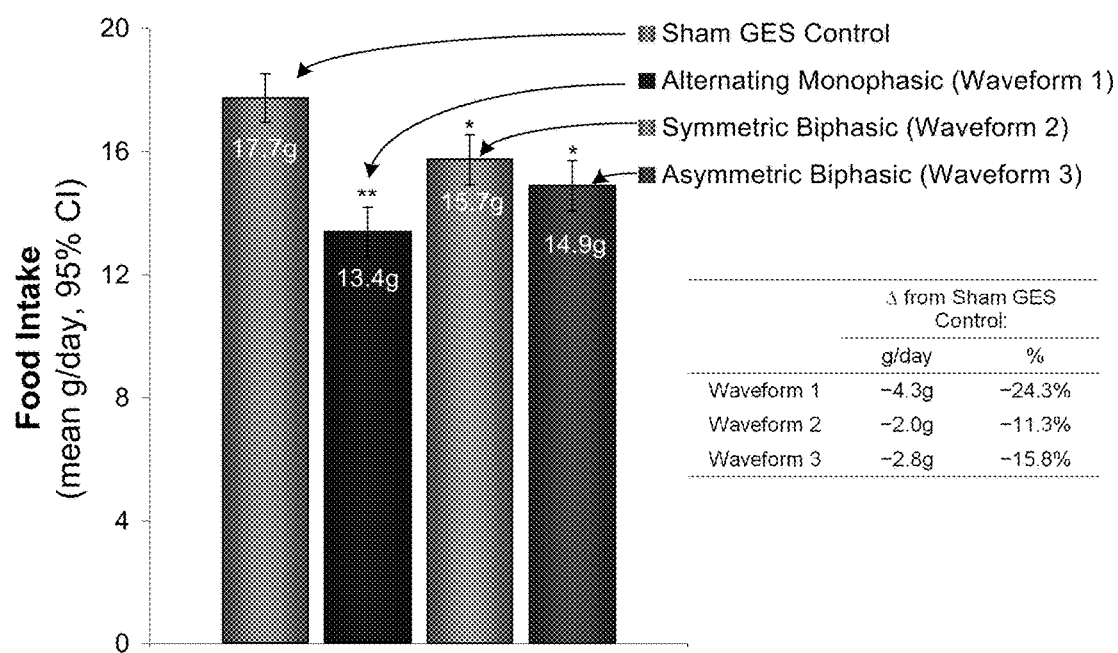
FIG. 14 is a plot illustrating measured mean food intake for various experimental conditions.

FIG. 14 is a plot illustrating the measured mean food intake for the sham stimulation period, Waveform 1 stimulation period, Waveform 2 stimulation period, and Waveform 3 stimulation period. The values shown are least squares means from a repeated measures regression including fixed treatment, rat and time period effects. The model was estimated using 380 daily observations on food intake in 19 sample rats. As shown, relative to the sham stimulation, mean daily food intake was reduced by about 24.3%, about 11.3% and about 15.8% under Waveform 1, Waveform 2, and Waveform 3 stimulation treatments, respectively ($p<0.0001$). Feeding suppression was significantly greater under the Waveform 1 stimulation treatment than either Waveform 2 and Waveform 3 stimulation treatments (p<0.0001), but did not differ significantly across Waveform 2 and 3 stimulation treatments (p=0.15).

Example 4

An experiment was undertaken to evaluate Waveform 1 stimulation using different pulse widths with regard to food intake and bodyweight in obese rats. For the experiment, one pair of stranded, stainless steel wire electrodes were implanted in the muscularis of the gastric antrum of in each of 16 obese male Sprague-Dawley rats (aged 16-17 weeks, mean weight: about 512 grams, range: about 439-640 grams). Lead wires were externalized on the rats' backs for connection to an external pulse generator. The sample rats were of a diet induced obesity prone phenotype and were conditioned to obesity with 6 weeks of 24 hour ad libitum access to a standardized high fat diet (Research Diets D12451, 45% of kcal from fat). After surgical recovery, the rats underwent 19 days of acclimation to feeding exclusively for two hours per day in a restrainer with alligator clip wires attached to their external lead wires. A surplus of high fat diet pellets was provided during each feeding period. The restrainers were used to limit the rats' movements enough to allow stimulation delivery during feeding.

After restrainer feeding acclimation, the rats were randomized into a 4×4 Latin Square cross-over design in which each rat received a sequence of four treatments in one of four assigned orders. Four sample rats were allocated to each ordering. Treatments included active stimulation using Waveform 1 with three different pulse widths (about 0.5, about 2.0, and about 5.0 milliseconds) and stimulation-Off control. Pulse amplitude was fixed at approximately six milliamps for all active treatments, and pulses were delivered at a frequency of approximately 40 hertz in two second bursts, separated by three second burst-off periods. Stimulation was delivered only during two hour restrainer feedings using World Precision Instruments Model A365 pulse generators with Model A395D stimulus isolators (World Precision Instruments, Sarasota, Fla.) connected to the externalized leads by alligator clip wires. Each treatment was delivered on four consecutive days and was separated from the next treatment by a three day washout period. The rats continued the restrainer feeding regimen without stimulation during washouts. Food intake was measured daily, and changes in bodyweight over each treatment period were calculated from bodyweights taken before feeding on the first day of each treatment period and on the first day of the subsequent washout.

Food intake and bodyweight change outcomes were analyzed with repeated-measures regressions including fixed effects for treatment, time period, and animal. Results are reported as least squares mean values (±SE) for food intake and weight change by treatment; and differences in these means across the active gastric stimulation conditions and the sham-stimulation control. The statistical significance of differences between treatment and control was assessed with model-based t-tests. Linear contrast F-tests were used to assess dose responses of food intake and bodyweight to increases in stimulation pulse width as evidenced by a statistically significant linear trend.

Figure 15:
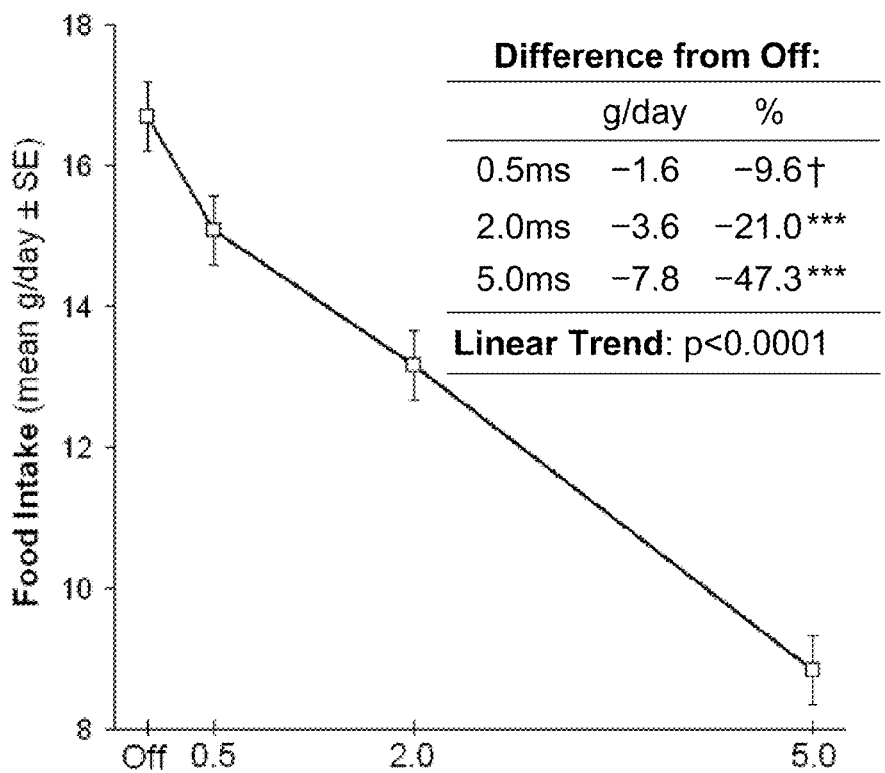
FIG. 15 is a plot illustrating measured mean food intake for various experimental conditions.

FIG. 15 is a plot illustrating the measured mean food intake for each of the four stimulation conditions. As shown, mean food intake was significantly lower under the active stimulation treatments than under sham (stimulation-Off) stimulation. Consistent with a pulse width dose response, there was a clear downward trend in food intake with increasing pulse width. Compared to the stimulation-Off control condition, mean restrainer food intake was about 9.6%, about 21.0% and about 47.3% lower during the 0.5, 2.0 and 5.0 millisecond pulse width treatment periods, respectively. The observed reductions in food intake were statistically significant for all three pulse widths (p<0.05 for 0.5; p<0.0001 for 2.0 and 5.0 milliseconds), as was the linear trend in food intake with pulse width (p<0.0001).

Figure 16:
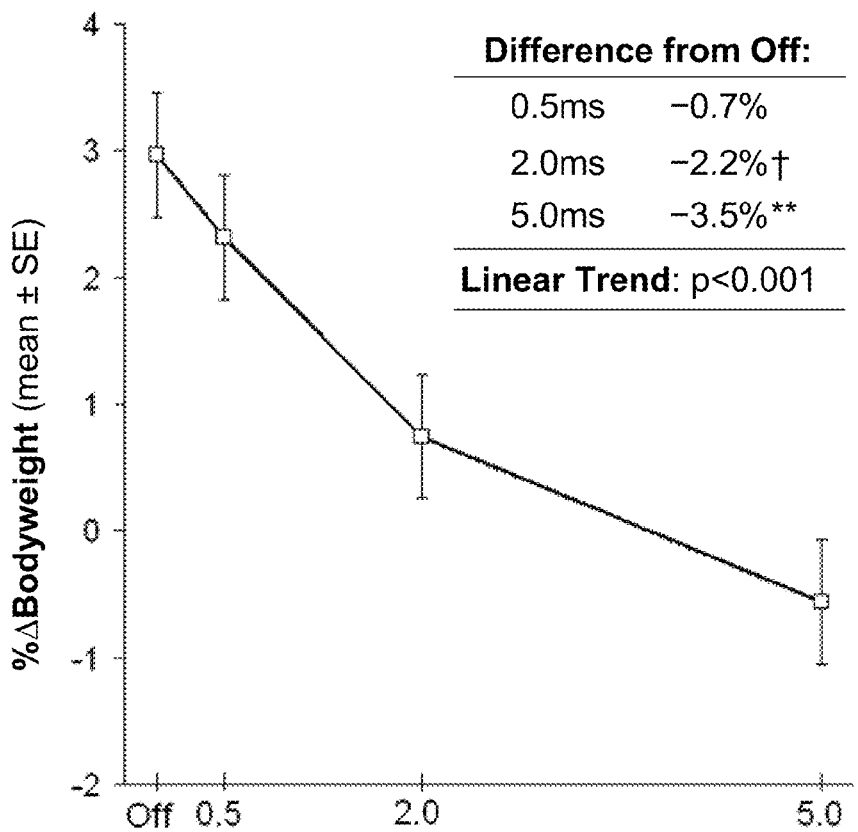
FIG. 16 is a plot illustrating measured percent change in body weight for various experimental conditions.

FIG. 16 is a plot illustrating measured percent change in body weight for each of the four stimulation conditions. As show, food intake suppression during active stimulation treatment was associated with a suppression of weight gain in a pulse-width-dependent fashion. While bodyweight increased an average of about 3.2% over the four-day sham (stimulation-Off) stimulation treatment periods, the mean gains over the 0.5 and 2.0 millisecond pulse width treatment periods amounted to only about 2.5% and about 1.0%, respectively, of bodyweight. Under the 5.0 millisecond pulse width treatment, the rats' bodyweights actually declined by an average of about 0.3%. Percentage weight change was significantly different from the sham stimulation control treatment under the 2.0 ms (p<0.05) and 5.0 ms (p<0.001) gastric stimulation treatments, but not under the 0.5 ms treatment (p=0.4811). The downward trend in percentage weight change with increasing stimulation pulse width was also statistically significant in the linear trend test (p<0.001).

For FIGS. 15 and 16, plotted values are least squares means (±SE) of food intake and percentage changes in bodyweight over four-day treatment periods from repeated measures regressions including fixed treatment, time and rat effects, and estimated using 256 rat-day observations on food intake and 128 pre- and post-treatment observations on bodyweight.

Example 5

An experiment was undertaken to evaluate Waveform 1 stimulation using different pulse amplitudes with regard to food intake, gastric volume, and gastric emptying in obese rats. For the experiment, one pair of stranded, 0.2 mm diameter, platinum-iridium wire electrodes were implanted in the muscularis of the gastric antrum in each of 17 obese male Sprague-Dawley rats (aged 16-17 weeks, mean weight: about 556 grams, range: about 460-671 grams). Lead wires were externalized on the rats' backs for connection to an external pulse generator. The sample rats were of a diet induced obesity prone phenotype and were conditioned to obesity with six weeks of 24 hour ad libitum access to a standardized high fat diet (Research Diets D12451, 45% of kcal from fat). After surgical recovery, the rats underwent 21 days of conditioning to a restricted, two-hour-per-day feeding schedule in their home cages, followed by five days of acclimation to feeding exclusively for two hours per day in a restrainer with alligator clip wires attached to their external lead wires. A surplus of high fat diet pellets was provided during each feeding period. The restrainers were used to limit the rats' movements enough to allow stimulation delivery during feeding.

Following conditioning to the restrainer feeding regimen, the sample rats entered into a food intake cross-over experiment, in which each rat received four days of each comparison treatment during daily feedings in a randomly assigned order. Treatment periods were separated by three day washout periods. Treatments were sham stimulation control, and active Waveform 1 stimulation with a pulse amplitude of about six milliamps and about 10 milliamps. Pulse width was fixed at about four milliseconds in both active treatments, and pulses were administered continuously at a frequency of approximately 40 hertz. All pulses were delivered using DS8000 pulse generators and DLS100 linear stimulus isolators (World Precision Instruments, Sarasota, Fla.), with stimulation beginning about 30 minutes prior to daily feedings and continuing throughout the two hour feeding period. Rats assigned to sham stimulation control had alligator clip wires attached to their externalized leads in the same fashion as rats assigned to active treatment, but no stimulation was delivered. Food intake was measured daily by weighing the food provided and the residual remaining at the end of each feeding. The experiment generated a total of 204 daily observations on food intake, which were analyzed using a repeated measures regression including fixed treatment, rat, and time period effects.

After completion of the food intake experiment, the sample rats were randomized to receive sham stimulation (N=5), the six milliamps pulse treatment (N=6) or the ten milliamps pulse treatment (N=6) for 105 minutes in the restrainer just prior to necropsy. Each rat was provided and consumed an approximately 2.5 gram solid meal following the first 15 minutes of active or sham stimulation. Substantially immediately after a 105 minute treatment period, each rat was sacrificed by pentobarbitol injection, the abdomen was opened, and the stomach was tied off with sutures and excised. The volume of the excised stomach was measured using a water displacement volumeter, and the contents of the stomach were carefully removed and air dried. Gastric emptying at about 90 minutes following the approximately 2.5 gram test meal was calculated as 100×[1−(dried contents, grams)/2.5]. The stomach of one sham stimulation rat was damaged during excision, and could not be used for post-mortem gastric volume or emptying measurements, thereby reducing the pre-necropsy sham stimulation control sample from five to four rats.

Figure 17:
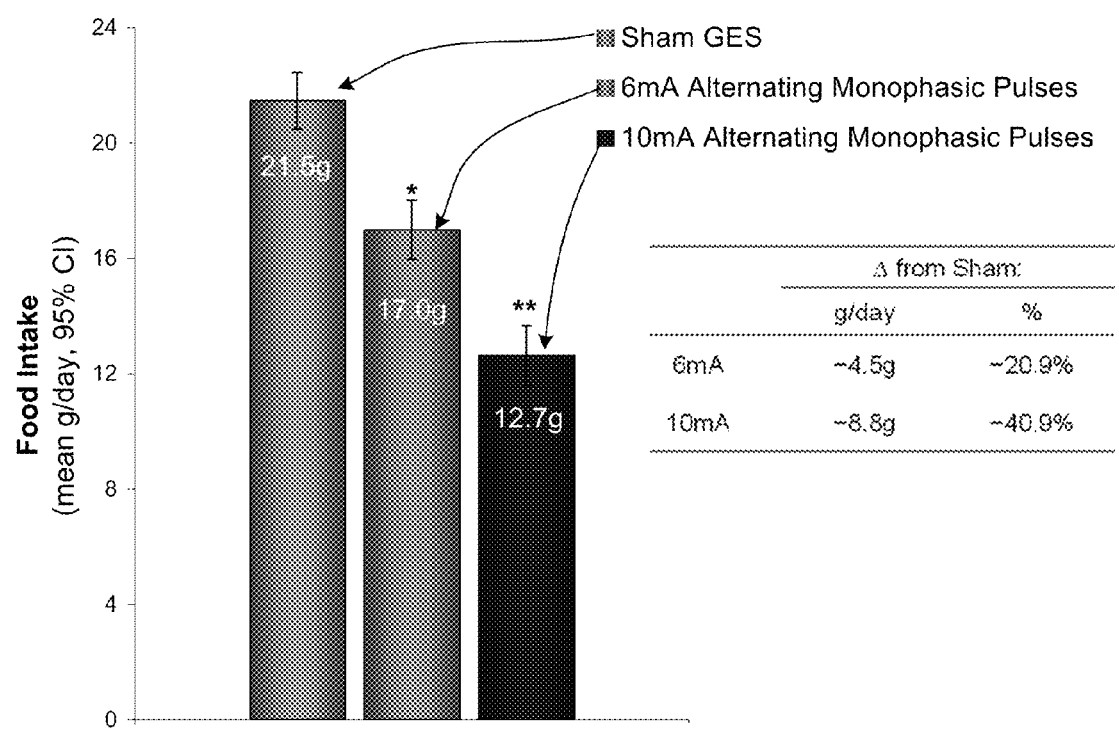
FIG. 17 is a plot illustrating measured food intake for each of the three example stimulation conditions.

FIG. 17 is a plot illustrating measured food intake for each of the three stimulation conditions. As shown in FIG. 17, mean daily food intake was reduced by approximately 4.5 grams or about 20.9% from the sham (stimulation-Off) stimulation control level under the approximately six milliamps Waveform 1 treatment (p<0.0001). Increasing the amplitude of the Waveform 1 stimulation pulses to approximately 10 milliamps increased the reduction in daily food intake from sham levels to approximately 8.8 gram or about 40.9% (p<0.0001). This reduction was significantly greater than that observed under the lower amplitude treatment (p<0.0001).

Figure 18:
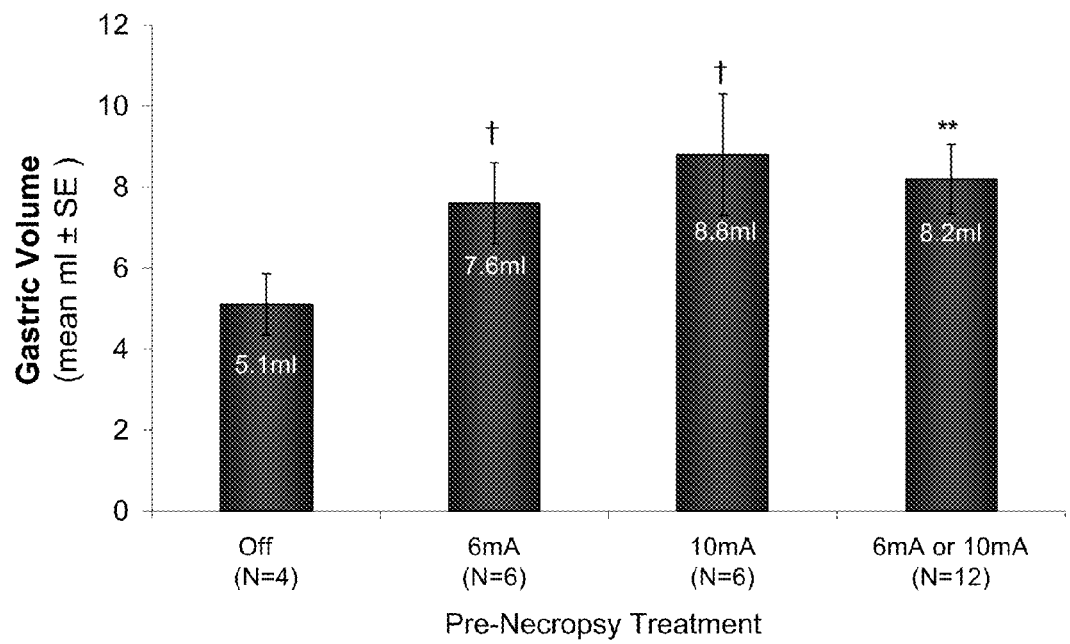
FIGS. 18 and 19 are plots illustrating measured gastric volume and gastric emptying, respectively, for various experimental conditions.
Figure 19:
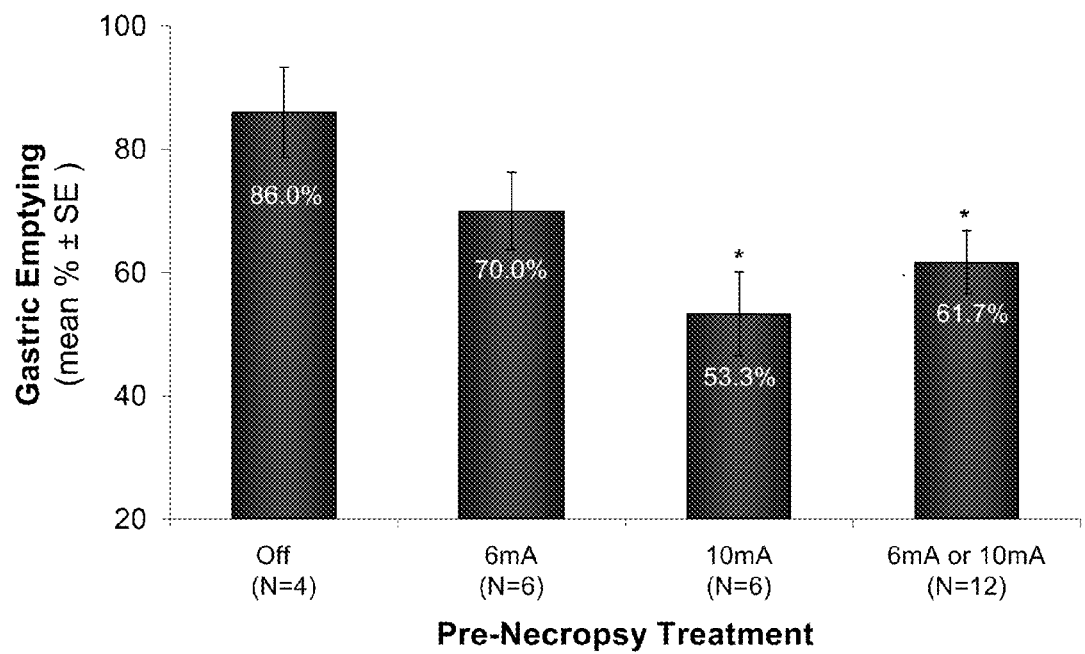

FIGS. 18 and 19 are plots illustrating measured gastric volume and gastric emptying, respectively, for each of each stimulation condition. The measurements shown were made following 105 minutes of pre-necropsy treatment with sham stimulation, or active Waveform 1 stimulation with pulse amplitudes of six or 10 milliamps. As shown, pre-necropsy treatment with Waveform 1 stimulation was associated with significantly higher gastric volume (p<0.025) and significantly lower gastric emptying (p<0.05) than pre-necropsy sham (stimulation-Off) stimulation. Mean gastric volume and emptying percentages also showed dose responses to stimulation amplitude, though these did not reach statistical significance.

Figure 20:
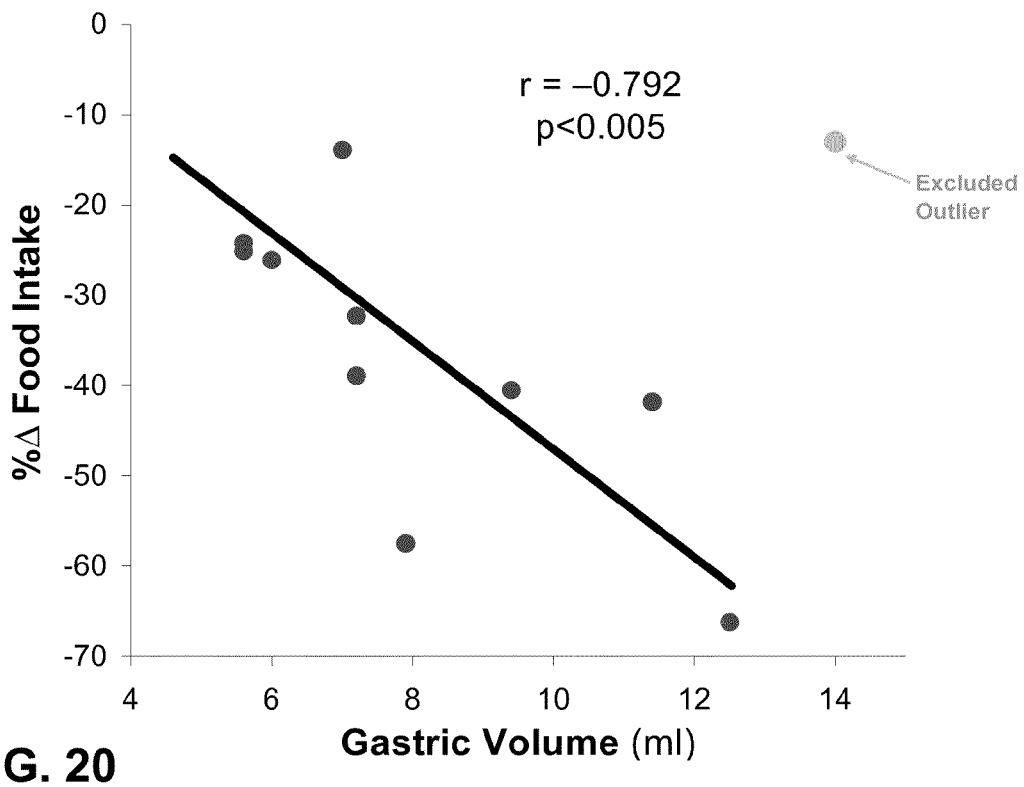
FIGS. 20 and 21 are plots illustrating measured food intake versus gastric volume and gastric emptying, respectively, for an experimental condition.
Figure 21:
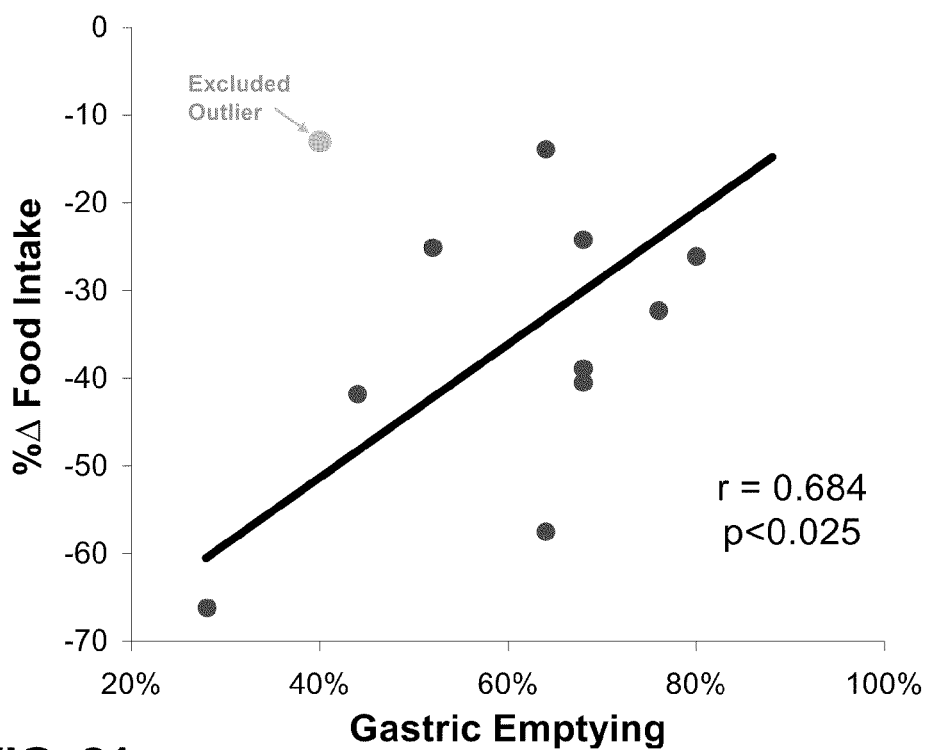

FIGS. 20 and 21 are plots illustrating measured food intake versus gastric volume and gastric emptying, respectively, for the twelve rats that received pre-necropsy, Waveform 1 stimulation. One of the twelve rats receiving active stimulation prior necropsy gastric volume and emptying responses at the upper tail of the sample distribution, but had little food intake response to stimulation during the preceding cross-over experiment. With this outlier excluded from the sample, however, both gastric emptying and gastric volume measurements in the remaining 11 rats receiving active stimulation prior to necropsy were highly correlated with their food intake responses to stimulation in the preceding cross-over experiment. Higher post-mortem gastric volume and lower gastric emptying were both associated with greater stimulation induced reductions in food intake. This is consistent with inhibition of gastric tone and delay of gastric emptying being components of the mechanism by which gastric stimulation reduces food intake.

Example 6

An experiment was undertaken to evaluate three different examples waveforms by delivering GES to lean canines in a manner similar to that of Example 1. Platinum-iridium stranded wire electrodes were implanted in the muscularis of the distal gastric antrum of four lean mongrel dogs. A gastric cannula was also implanted for balloon barostat measurements of gastric volume. Percutaneous lead wires and an external pulse generator were used to deliver gastric electrical stimulation using three different waveforms. Similar to that of Example 1, the first waveform used for GES was Waveform 3. However, instead of using Waveforms 1 and 2 as in Example 1, the second waveform (referred to as "Waveform 4") was consistent with the example waveform illustrated in FIG. 8. Further, the third waveform (referred to as "Waveform 5") was consistent with the example waveform illustrated in FIG. 9. The pulse widths and amplitude of the first pulses of Waveform 3 (e.g., pulses 70a-70d) and the rectangular pulses of Waveform 4 and Waveform 5 were fixed at approximately four milliseconds and approximately six milliamps. The first pulses of Waveform 3 and the rectangular pulses of Waveforms 4 and 5 were delivered continuously at a frequency of approximately 40 hertz.

Waveforms 3 and 4 were delivered using a World Precisions Instruments DS8000 pulse generator and DLS100 linear stimulus isolator (World Precision Instruments, Sarasota, Fla.). Waveform 5 was delivered using a Medtronic Restore implantable pulse generator (available from Medtronic, Inc., MN) with firmware modified from its commercial release version to permit stacking of four shorter rectangular pulses to mimic a single longer rectangular pulse, e.g., in a manner substantially similar to that described with regard to FIG. 10. The need for such stacking in order to generate a rectangular stimulus with a width of four milliseconds (as was used in this experiment) may be a design limitation of the Restore pulse generator. One aspect of the stacking, which may be disadvantageous in some situations, is that it includes short gaps between the stacked pulses, on the order of 10-50 microseconds, during which the pulse generator begins a passive recharge of its capacitors. This causes a brief spike in current of opposite polarity to occur between each stacked pulse event. The hyperbolic recharge pulses in Waveforms 4 and 5 are typical of the passive recharge mechanism used in some commercial implantable pulse generators. The exact shape of this hyperbolic pulse reflects the specific characteristics of the capacitors in the device.

One purpose of the experiment was to test whether the current spikes in the stacked Restore stimulus pulses (Waveform 5 stimulation) diminished their effectiveness in inducing gastric distension relative to a true rectangular stimulus pulse followed by a hyperbolic recharge (Waveform 4 stimulation). Another purpose of the experiment was to test whether a hyperbolic recharge following a rectangular pulse (Waveform 5 stimulation) diminishes its effectiveness in inducing gastric distension relative to a higher amplitude rectangular pulse followed by a rectangular pulse of the smallest absolute amplitude possible determined by the pulse frequency, as describe with regard to Waveform 3 stimulation.

Three, forty-minute balloon barostat recordings of gastric volume, one for each waveform, were made in each dog. Measurements were made on separate days with the dogs in a fasted state, and consisted of a 10 minute baseline recording, followed by 10 minutes of recording during gastric electrical stimulation, and 20 minutes of recording after stimulation was shut off. Treatments were administered in one of three randomly assigned orders to control for test order effects. Barostat balloon volumes were recorded at a frequency of one hertz, yielding 2400 measurements per 40 minute testing session. These measurements were analyzed using a repeated measures model allowing for the dependence of volume recordings over time within each dog. Model estimates were used to test for differences in changes in mean balloon volume from baseline levels across treatments.

Figure 22:
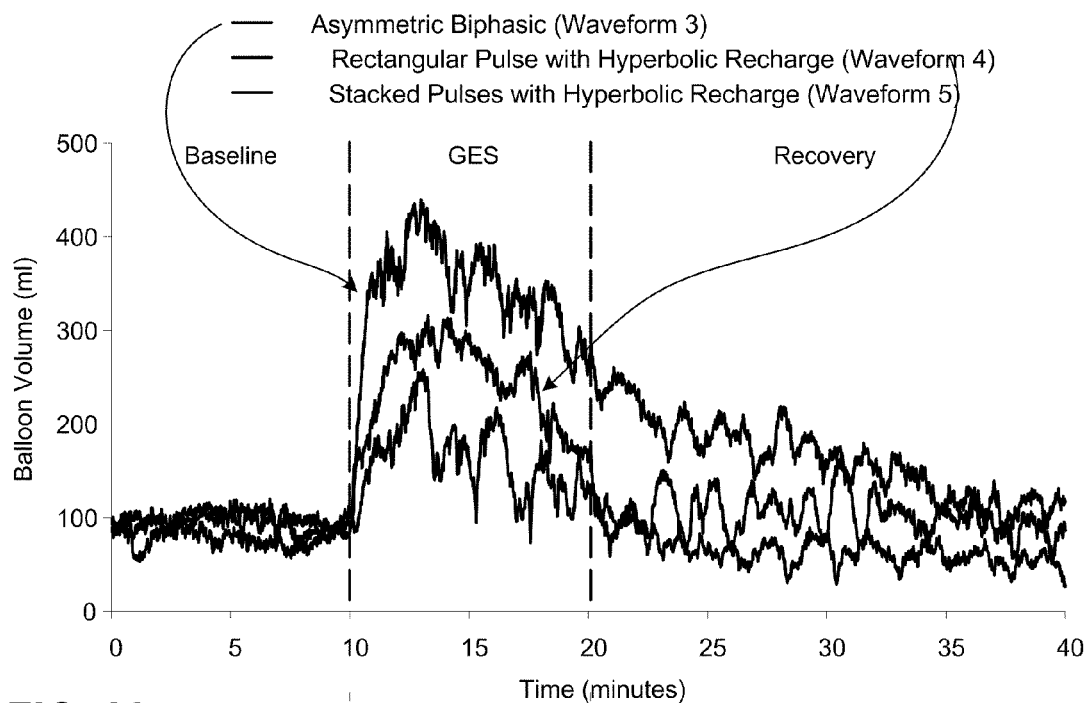
FIG. 22 is a plot illustrating measured barostat balloon volume versus time for various experimental stimulation conditions.

FIG. 22 is a plot illustrating measured barostat balloon volume versus time for each of Waveform 3-5. Each plotted value is the average of gastric barostat balloon volume measurements at a given time point across four sample dogs. As shown, Waveform 3 stimulation produced larger increases in fasted gastric volume than either Waveform 4 or Waveform 5 stimulation. The mean barostat balloon volume across the four sample dogs was higher at nearly every time point during the stimulation and recovery periods of the Waveform 3 stimulation sessions than during either Waveform 4 or 5 stimulation sessions.

Figure 23:
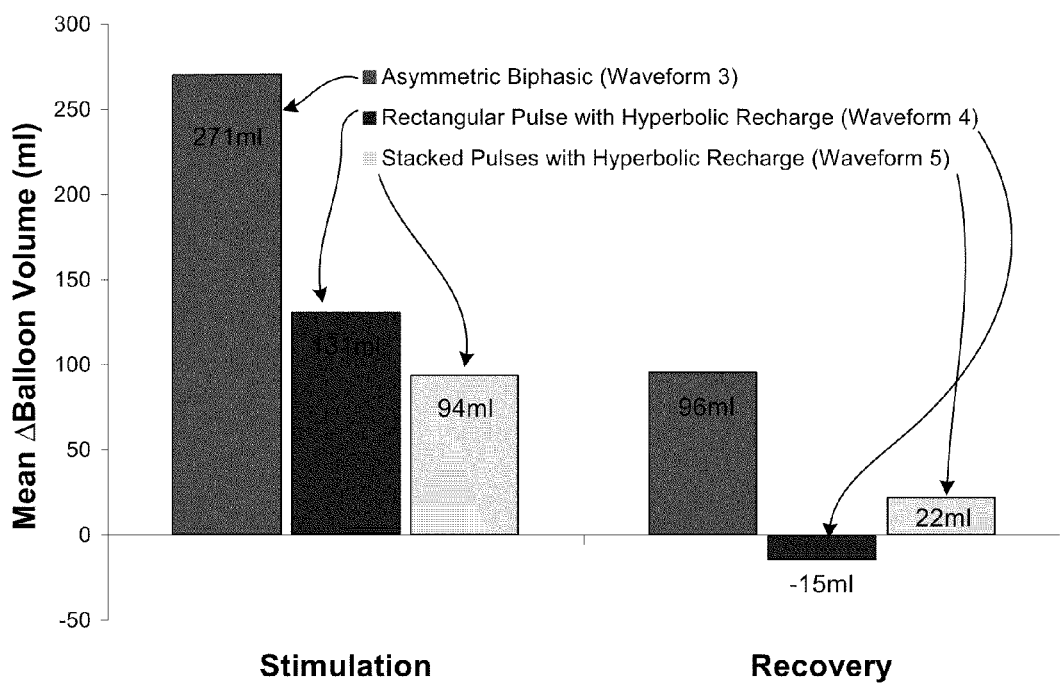
FIG. 23 is a plot illustrating mean change in barostat balloon volume during the delivery of gastric electric stimulation (GES) and during the 10 minute recovery period for various experimental stimulation conditions.

FIG. 23 is a plot illustrating mean change in barostat balloon volume during the delivery of gastric electric stimulation (GES) and during the 10 minute recovery period for each of Waveforms 3-5. During the 10-minute active stimulation period, mean barostat balloon volume rose by approximately 271 milliliters from baseline levels during stimulation with Waveform 3 stimulation, compared to only approximately 131 milliliters and approximately 94 milliliters during stimulation with Waveforms 4 and 5. The increase in balloon volume from basal levels was also larger during the post-stimulation recovery period following stimulation with Waveform 3 stimulation than after stimulation with either Waveform 4 or 5 (approximately 96 milliliters vs. approximately −16 milliliters or approximately 21 milliliters, respectively). During both the active stimulation and recovery periods, the volume-increase effectiveness advantage of Waveform 3 over either Waveform 4 and Waveform 5 was statistically significant ($p<0.0001$).

During the active stimulation period, the Waveform 4 stimulation was significantly more effective than the Waveform 5 stimulation generated by the Medtronic Restore with modified firmware. Thus, in some examples, there could be some gain in the gastric-distension inducing efficacy of stimulation with the Medtronic Restore if it could be modified to eliminate the amplitude spikes between stacked events in the stacked, rectangular pulse. The results of Example 6 suggest, however, that the hyperbolic recharge pulse of the Restore pulses is a larger detriment to its effectiveness in inducing gastric distension than the stacking of pulses in the stacked, rectangular pulse.

The GES-induced gastric distension reflected in increased barostat balloon volume has been found to activate neurons in brain nuclei linked to satiation and is one likely mechanism by which GES reduces food intake. Barostat measured increases in gastric volume induced by GES have previously been found to be predictive of food intake responses to GES in canines, with larger GES-induced increases in gastric volume being associated with larger GES-induced reductions in feeding.

Example 7

An experiment was undertaken to evaluate Waveform 1 in terms of weight change and food intake in obese rats. For the experiment, one pair of stranded, 0.2 mm diameter, platinum-iridium wire electrodes were implanted in the wall of the distal gastric antrum in each of thirty-two diet induced obese, male Sprague-Dawley rats (16 weeks of age, mean weight about 605 grams). Lead wires were externalized on the rats' backs, passing through a DC105 Dacron and silicone skin button and a SS105 stainless steel tether spring (Instech, Plymouth Meeting, Pa.) to a 205L electrical swivel (Mercotac, Carlsbad, Calif.) on a cage-top counterbalanced arm. Connecting wires attached to the counterbalanced arm were connected to DS8000 pulse generators and DLS100 linear stimulus isolators (World Precision Instruments, Sarasota, Fla.) for delivery of gastric electrical stimulation (GES). This setup allowed chronic home cage GES delivery while allowing the rats to move freely about their cages without twisting or becoming tangled in the implanted lead wires.

The rats were randomized in equal numbers to receive either active or sham GES treatment for 8 weeks while having 24 hour ad libitum access to a pelleted high fat diet (D12451 pellets, 45% of kcal from fat available from Research Diets, Inc., New Brunswick, N.J.). Active GES treatment was Waveform 1 stimulation with alternating rectangular monophasic pulses having a pulse width of approximately 5 milliseconds delivered continuously at a frequency of approximately 40 hertz for 16 hours each day. The pulses were evenly spaced, with approximately 25 milliseconds from the leading edge of one monophasic rectangular pulse to the next and approximately 20 millisecond delay between the end of one pulse and the start of the next. The daily 8 hour off period was chosen to coincide with the rats' sleep cycle. Pulse amplitude for the Active GES treatment stimulation was set to the highest asymptomatic value less than or equal to approximately 10 milliamperes, determined for each rat individually based on symptom testing conducted the day before the start of the experiment. The rats were weighed weekly, while food intake was measured continuously by a BioDaq automated monitor attached to the front of each cage (Research Diets, Inc., New Brunswick, N.J.). Experiment duration was chosen to be within the maximum useable longevity of the home cage tether implants, but long enough to provide evidence on the persistence of GES effects on food intake and body weight under chronic treatment. As a percentage of expected lifespan, 8 weeks for a Sprague-Dawley rat may be approximately equivalent to about 6 years for a human being.

Figure 24:
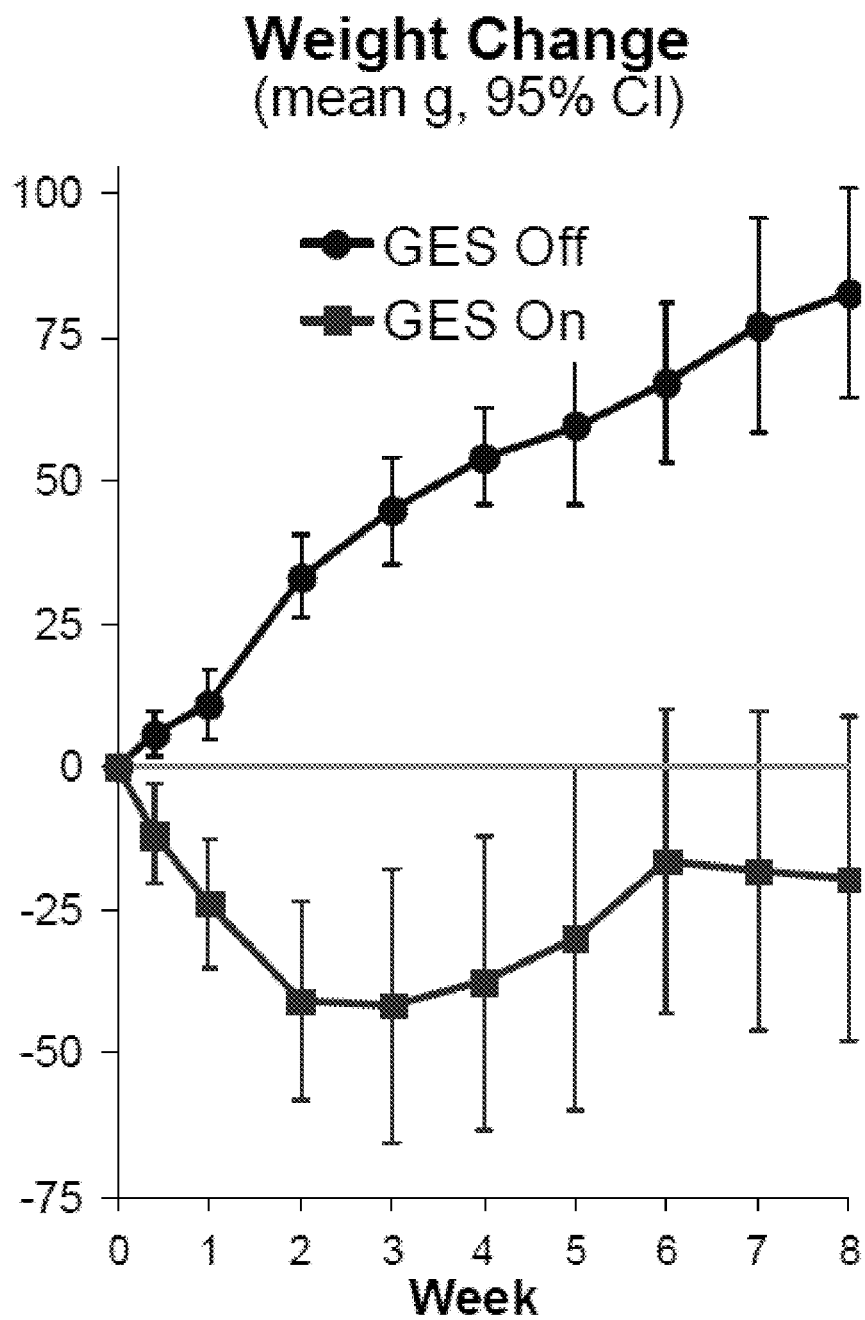
FIG. 24 is a plot of weight change versus time for an experimental condition.

FIG. 24 is a plot of weight change versus time for both the rats receiving the active GES stimulation (GES On) and the rats receiving sham GES stimulation (GES off). As shown, relative to the sham GES control group, mean body weight in the rats assigned to active GES treatment with Waveform 1 was reduced by about 16.9 percent or about 102 grams ($p<0.0001$) over 8 weeks.

Figure 25:
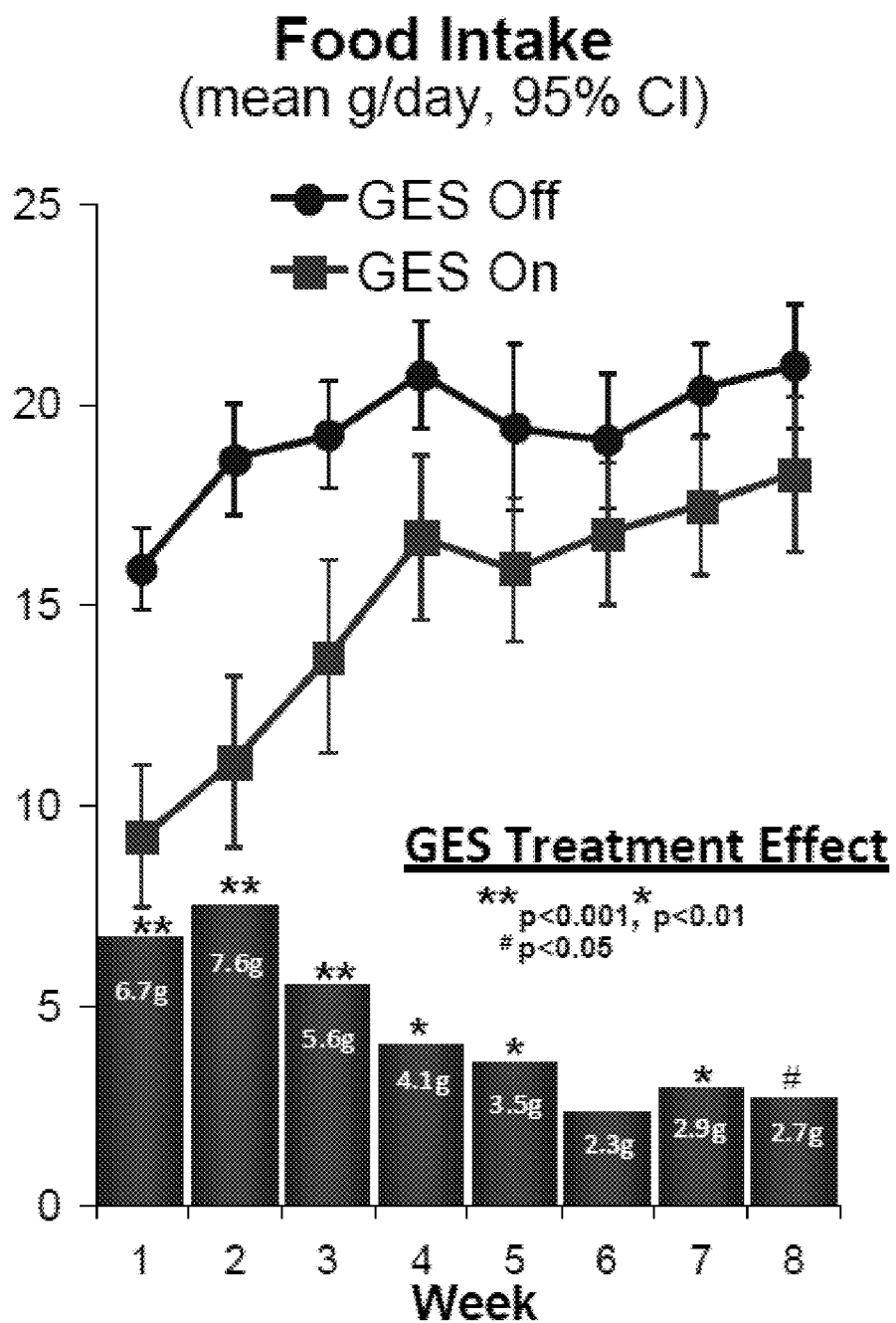
FIG. 25 is a plot of food intake versus time for an experimental condition.

FIG. 25 is a plot of food intake versus time for both the rats receiving the active GES stimulation (GES On) and the rats receiving sham GES stimulation (GES off). As shown, mean cumulative 8 week food intake was about 22.8 percent lower under active treatment than under control ($p<0.0001$).

While the magnitude of the food intake treatment effect may have declined over the course the 8-week experiment, there was still a statistically significant (p<0.05) suppression of food intake during the final week of the study.

Figure 26:
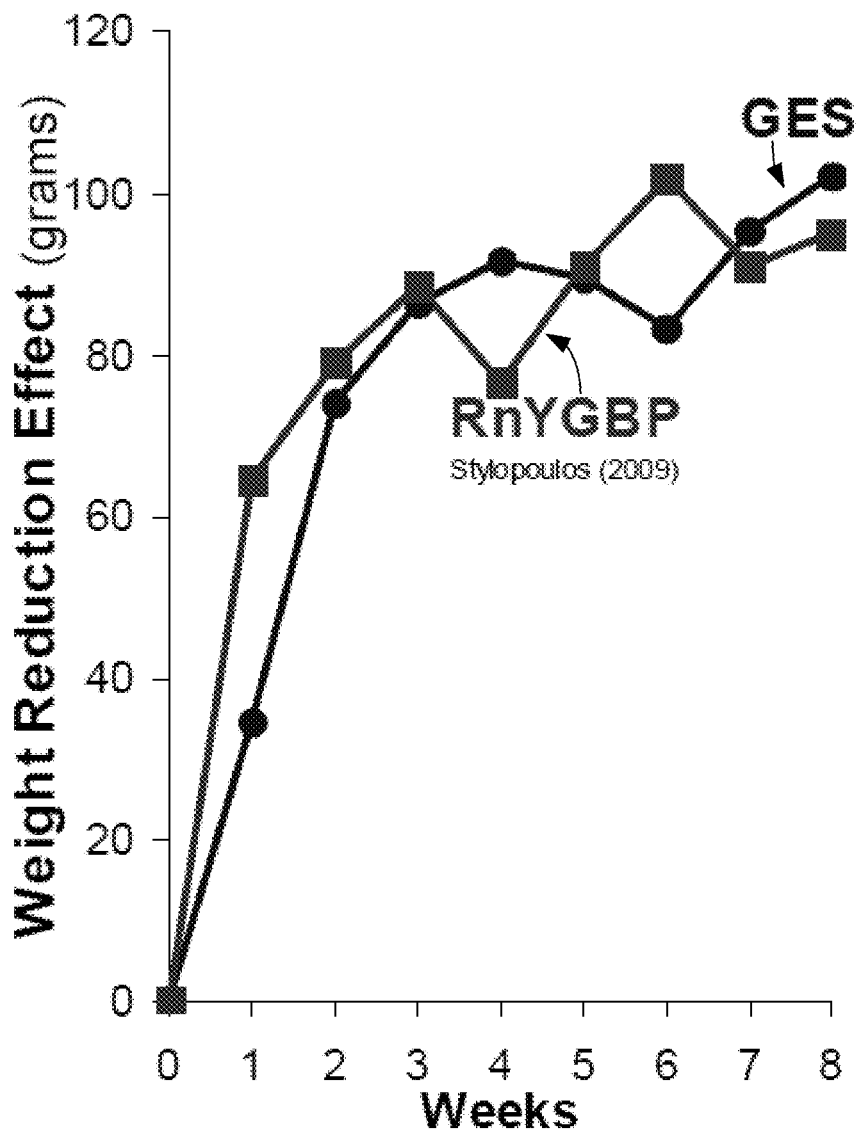
FIG. 26 is a plot of differences in weight in body weight versus time for various experimental conditions.

The GES induced reduction in body weight in this 8-week, chronic treatment experiment is substantially similar in some aspects to that reported in a 2009 study of Roux-en-Y gastric bypass conducted in the same diet induced obese Sprague-Dawley rat model (Stylopoulos et al., "Roux-en-Y gastric bypass enhances energy expenditure and extends lifespan in diet-induced obese rats," *Obesity*, 2009 17(10):1839-47.) FIG. 26 is a plot of differences in weight in body weight versus time comparing the results of the Example 7 to the Stylopoulos et al. (2009) study of Roux-en-Y gastric bypass cited above. In FIG. 26, the differences in weight change in grams from pre-surgery baseline levels across rats receiving gastric bypass and sham-surgery controls in this study is plotted by weeks from surgery for the study of Roux-en-Y gastric bypass (labeled as "RnYGBP Stylopoulos (2009)"). Also plotted in FIG. 26 are the differences in weight change in grams from pre-treatment baseline levels across rats receiving active GES using Waveform 1 and those receiving sham GES treatment for each week of the experiment of Example 7 (labeled as "GES"). As shown in FIG. 26, the plot of the GES body weight reduction effect from the experiment of FIG. 7 closely coincides with that observed in Stylopoulos et al. (2009) study of Roux-en-Y gastric bypass.

Another prevalent surgical treatment for obesity is gastric banding. Weight reduction effects relative to sham surgery controls have been reported in the following published studies of gastric banding in rat models: 1) Kanno H, et al., "Rat gastric banding model for bariatric surgery," *J Nippon Med Sch.* 2008 75(4):202-6; 2) Endo Y, et al., "An obese rat model of bariatric surgery with gastric banding," *Obes Surg.* 2007 17(6):815-9; 3) Monteiro M P, et al. "A rat model of restrictive bariatric surgery with gastric banding," *Obes Surg* 2006 16(1):48-51; 4) Monteiro M P, et al., "Rats submitted to gastric banding are leaner and show distinctive feeding patterns," *Obes Surg.* 2006 16(5):597-602; 5) Monteiro M P, et al., "Increase in ghrelin levels after weight loss in obese Zucker rats is prevented by gastric banding," *Obes Surg.* 2007 17(12):1599-607; and 6) Kampe J, et al., "A rodent model of adjustable gastric band surgery-implications for the understanding of underlying mechanisms," *Obes Surg* 2009 19(5):625-31.

Figure 27:
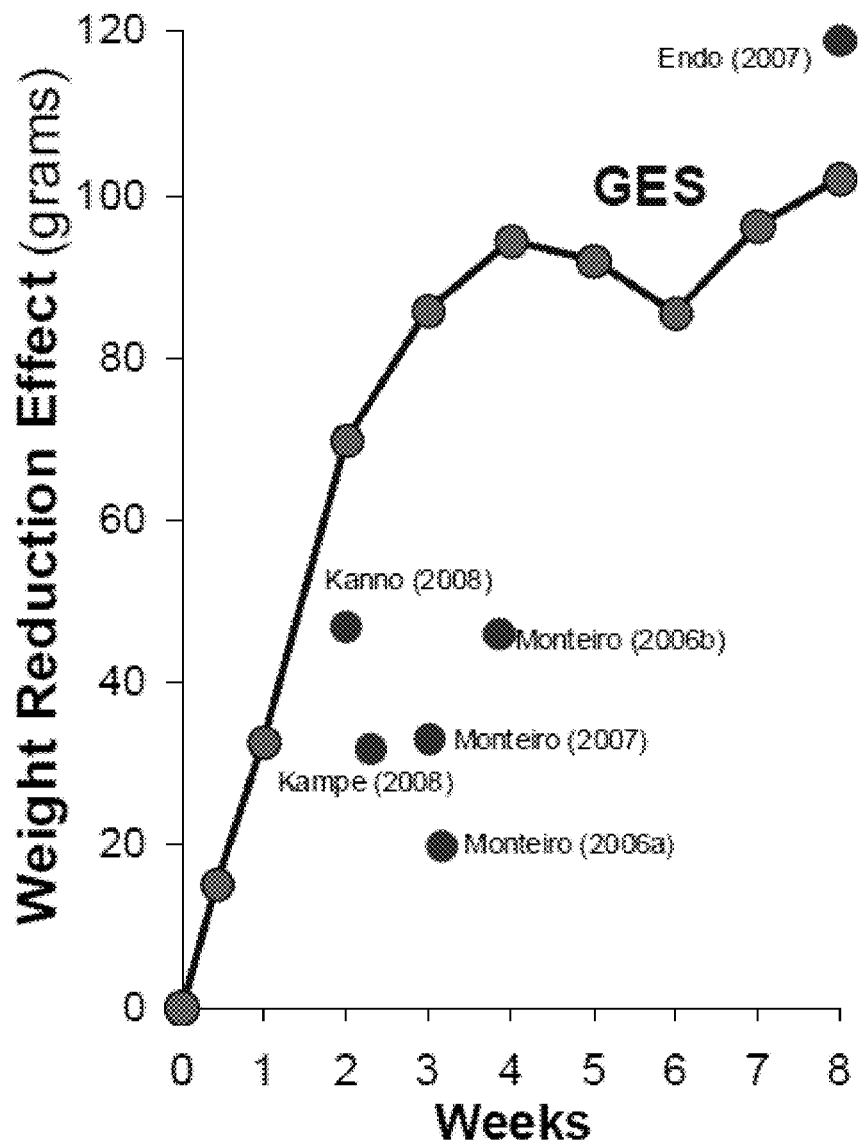
FIG. 27 is a plot of weight reduction effects versus time for various experimental conditions.

FIG. 27 is a plot of weight reduction effects versus time for each of the six published studies above and for the experiment of Example 7. As shown in FIG. 27, the weight reduction effects by week of GES treatment with Waveform 1 observed in Example 7 compare favorably with the weight reduction effects relative to sham surgery controls that were reported in the above published studies of gastric banding in rat models. With one exception (Endo et al.), all of the above gastric banding studies were of shorter duration than Experiment #7, but in all of these cases the reported end-of-experiment weight reduction effects of banding were less than the observed weight reduction effect of chronic GES treatment with Waveform 1 at comparable time points.

Various aspects of the disclosure have been described. In one aspect, the disclosure relates to a method comprising delivering a series of pulses to a series of pulses with alternating pulse polarities to a patient, wherein the series of pulses includes at least a first pulse of a first polarity, a second pulse of a second polarity, and a third pulse of the first polarity, wherein the first, second and third pulses are delivered in direct succession, in that order, wherein an amplitude of the second pulse is less than an amplitude of the first pulse and an amplitude of the third pulse, wherein the amplitude and pulse width of the second pulse is selected such that the first, second, and third pulses each have approximately the same charge.

In some examples, the pulse width of the second pulse is selected such that first, second, and third pulses are delivered without any substantial time delay between the pulses. In some examples, the amplitude of the second pulse is substantially uniform. In some examples, each of the series of pulses have a pulse width between approximately 0.05 milliseconds and approximately 1000 milliseconds. In some examples, the series of pulses are delivered at frequency between approximately 0.05 Hz and 40 Hz. In some examples, each of the series of pulses have an amplitude less than or equal to approximately 25 volts. In some examples, the method further comprising identifying the patient as obese, wherein the electrical stimulation is delivered to the patient based at least in part on the identification. In some examples, the first and second pulses comprise a coupled pulse pair. In some examples, the second pulse is delivered substantially immediately after the first pulse.

In some examples, delivering the series of pulses with alternating pulse polarities to the patient comprises delivering the series of pulses with alternating pulse polarities to a gastrointestinal tract of the patient. In some examples, delivering the series of pulses with alternating pulse polarities to a gastrointestinal tract of the patient comprises delivering the series of pulses a stomach of the patient. In some examples, the series of pulses are configured to increase the distention of a stomach of a patient.

In some aspects, the disclosure relates to a medical device system including a stimulation generator configured to generate and deliver a series of stimulation pulses to a patient, and a processor configured to control the series of pulses generated and delivered by the stimulation generator according to one or more examples described above. In some examples, the stimulation generator comprises an implantable stimulation generator. In some examples, the medical device system further comprises one or more electrodes configured to deliver the series of pulses to the patient, and/or one or more implantable leads. In some examples, the medical device system comprises an implantable medical device.

In some aspects, the disclosure relates to a medical device system comprising means for delivering a series of pulses to a series of pulses with alternating pulse polarities to a patient, wherein the series of pulses includes at least a first pulse of a first polarity, a second pulse of a second polarity, and a third pulse of the first polarity, wherein the first, second and third pulses are delivered in direct succession, in that order, wherein an amplitude of the second pulse is less than an amplitude of the first pulse and an amplitude of the third pulse, wherein the amplitude and pulse width of the second pulse is selected such that the first, second, and third pulses each have approximately the same charge.

Various aspects of the disclosure have been described. These and other aspects are within the scope of the following claims.

The invention claimed is:

1. A method comprising controlling, via at least one processor, delivery from a medical device to a target location of a gastrointestinal (GI) tract of a patient of a sequence of pulses at a specified frequency, with each pulse having a single polarity, with all even numbered pulses in the sequence having one polarity and all odd numbered pulses in the sequence having an opposite polarity, in a fashion such that respective intervals between consecutive pulses in the sequence increases with decreases in the specified frequency of delivery, and decreases with increases in the specified frequency of delivery.

2. A medical device system comprising:
a stimulation generator configured to generate and deliver a series of pulses having alternating pulse polarities to a patient; and
a processor configured to control the series of pulses generated and delivered by the stimulation generator,
wherein the device is configured to deliver the series of pulses to a target location of a gastrointestinal (GI) tract of a patient, wherein each pulse having a single polarity, with all even numbered pulses in the sequence having one polarity and all odd numbered pulses in the sequence having an opposite polarity, in a fashion such that respective intervals between consecutive pulses in the sequence increases with decreases in the specified frequency of delivery, and decreases with increases in the specified frequency of delivery.

3. A non-transitory computer-readable storage medium comprising instructions to cause a programmable processor to control a stimulation generator to deliver a series of pulse pairs with alternating pulse polarities from a medical device to a target location of a gastrointestinal (GI) tract of a patient, wherein each pulse has a single polarity, with all even numbered pulses in the sequence having one polarity and all odd numbered pulses in the sequence having an opposite polarity, in a fashion such that respective intervals between consecutive pulses in the sequence increases with decreases in the specified frequency of delivery, and decreases with increases in the specified frequency of delivery.

4. A method comprising controlling, via at least one processor, delivery of a series of pulses with alternating pulse polarities from a medical device to a target location of a gastrointestinal (GI) tract of a patient, wherein the series of pulses includes at least a first pulse of a first polarity, a second pulse of a second polarity, a third pulse of the first polarity, and a fourth pulse of the second polarity, wherein the first, second, third and fourth pulses are delivered to the target location in direct succession, in that order, wherein the first pulse and second pulse are separated by a first time delay, the second pulse and third pulse are separated by a second time delay, the third pulse and the fourth pulse are separated by a third time delay, and wherein an increase in a pulse frequency of the series of pulses causes the first time delay, the second time delay, and third time delay to decrease in duration, and a decrease in the pulse frequency of the series of pulses causes the first time delay, the second time delay, and third time delay to increase.

5. The method of claim 4, wherein each pulse of the series of pulses has a pulse width between approximately 0.05 milliseconds and approximately 1000 milliseconds.

6. The method of claim 4, wherein the series of pulses are delivered at a pulse frequency between approximately 0.05 Hz and approximately 40 Hz.

7. The method of claim 4, wherein each pulse of the series of pulses has an amplitude greater than zero but less than or equal to approximately 25 volts.

8. The method of claim 4, wherein the series of pulses are delivered with a controlled current, and each pulse of the series of pulses has an amplitude greater than zero but less than or equal to approximately 25 milliamps.

9. The method of claim 4, wherein the first time delay and second time delay are approximately equal and vary with the pulse frequency.

10. The method of claim 4, wherein first, second, third, and fourth pulses have approximately the same charge amount.

11. The method of claim 4, wherein delivering the series of pulses with alternating pulse polarities to the target location of the gastrointestinal tract of the patient comprises delivering the series of pulses to a stomach of the patient.

12. The method of claim 11, wherein the delivery of the series of pulses to the stomach of the patient increases distention of the stomach of the patient.

13. The method of claim 4, further comprising identifying the patient as obese, wherein the electrical stimulation is delivered to the patient based at least in part on the identification.

14. The method of claim 4, further comprising adjusting an amplitude of one or more of the pulses of the series of pulses to maintain charge balance.

15. The method of claim 4, further comprising adjusting a pulse width of one or more of the pulses of the series of pulses to maintain charge balance.

16. The method of claim 4, further comprising increasing the pulse frequency of the series of pulses, wherein increasing the pulse frequency comprises decreasing the first time delay, the second time delay, and third time delay.

17. The method of claim 4, further comprising decreasing the pulse frequency of the series of pulses, wherein decreasing the pulse frequency comprises increasing the first time delay, the second time delay, and the third time delay.

18. The method of claim 4, wherein each pulse of the series of pulses has a pulse width between approximately 1 milliseconds and approximately 5 milliseconds.

19. The method of claim 4, wherein the series of pulses are delivered at a pulse frequency between approximately 1 Hz and approximately 40 Hz.

20. The method of claim 4, wherein the first time delay, second time delay, and third time delay are approximately equal.

21. The method of claim 4, wherein a fourth time delay follows the fourth pulse.

22. The method of claim 21, wherein the increase in the pulse frequency of the series of pulses causes the fourth time delay to decrease in duration, and the decrease in the pulse frequency of the series of pulses causes the fourth time delay to increase.

23. The method of claim 21, wherein the second time delay and the fourth time delay are approximately equal.

24. A medical device system comprising:
a stimulation generator configured to generate and deliver a series of pulses having alternating pulse polarities to a patient; and
a processor configured to control the series of pulses generated and delivered by the stimulation generator,
wherein the device is configured to deliver the series of pulses to a target location of a gastrointestinal (GI) tract of a patient, wherein the series of pulses includes at least a first pulse of a first polarity, a second pulse of a second polarity, a third pulse of the first polarity, and a fourth pulse of the second polarity, wherein the first, second, third and fourth pulses are delivered to the target location in direct succession, in that order, wherein the first pulse and second pulse are separated by a first time delay, the second pulse and third pulse are separated by a second time delay, the third pulse and the fourth pulse are separated by a third time delay, and wherein an increase in a pulse frequency of the series of pulses causes the first time delay, the second time delay, and third time delay to decrease in duration, and a decrease in the pulse frequency of the series of pulses causes the first time delay, the second time delay, and third time delay to increase.

25. The medical device system of claim 24, further comprising at least one elongated lead including at least one electrode, the at least one lead configured to be attached to a wall of the GI tract of the patient, wherein the at least one electrode delivers the series of pulses to the GI tract of the patient from the stimulation generator when the at least one lead is anchored to the wall of the GI tract of the patient.

26. The medical device system of claim 24, wherein the processor controls each pulse of the series of pulses to have a pulse width between approximately 0.05 milliseconds and approximately 1000 milliseconds.

27. The medical device system of claim 24, wherein the processor controls the series of pulses to be delivered at a pulse frequency between approximately 0.05 Hz and approximately 40 Hz.

28. The medical device system of claim 24, wherein the processor controls each pulse of the series of pulses to have an amplitude greater than zero but less than or equal to approximately 25 volts.

29. The medical device system of claim 24, wherein the processor controls each pulse of the series of pulses to have an amplitude greater than zero but less than or equal to approximately 25 milliamps.

30. The medical device system of claim 24, wherein the processor controls the series of pulses such that the first time delay and second time delay are approximately equal and vary with the pulse frequency.

31. The medical device system of claim 24, wherein the processor controls the first, second, third, and fourth pulses to have approximately the same charge amount.

32. The medical device system of claim 24, wherein delivering the series of pulses with alternating pulse polarities to the target location of the gastrointestinal tract of the patient comprises delivering the series of pulses to a stomach of the patient.

33. The medical device system of claim 30, wherein the delivery of the series of pulses to the stomach of the patient to increases distention of the stomach of the patient.

34. The medical device system of claim 24, wherein the processor is configured to identify the patient as obese, and wherein the processor controls the delivery of the series of pulses to the patient based at least in part on the identification.

35. The medical device system of claim 24, wherein the stimulation generator comprises an implantable stimulation generator.

36. The medical device system of claim 24, further comprising one or more implantable leads configured to deliver the series of pulses to the target location of the GI tract of the patient.

37. The medical device system of claim 24, wherein the processor is configured to control the series of pulses to increase the pulse frequency, wherein the increase in pulse frequency causes a decrease the first time delay, the second time delay, and third time delay.

38. The medical device system of claim 24, wherein the processor is configured to control the series of pulses to decrease the pulse frequency, wherein the decrease in pulse frequency causes an increase in the first time delay, the second time delay, and the third time delay.

39. The medical device system of claim 24, wherein the processor is configured to control each pulse of the series of pulses to have a pulse width between approximately 1 milliseconds and approximately 5 milliseconds.

40. The medical device system of claim 24, wherein the processor is configured to control the series of pulses to be delivered at a pulse frequency between approximately 1 Hz and approximately 40 Hz.

41. The medical device system of claim 24, wherein the processor is configured to control the series of pulses such that the first time delay, second time delay, and third time delay are approximately equal.

42. The medical device system of claim 24, wherein a fourth time delay follows the fourth pulse.

43. The medical device system of claim 42, wherein the increase in the pulse frequency of the series of pulses causes the fourth time delay to decrease in duration, and the decrease in the pulse frequency of the series of pulses causes the fourth time delay to increase.

44. The medical device system of claim 42, wherein the processor is configured to control the series of pulses such that the second time delay, and the fourth time delay are approximately equal.

45. A non-transitory computer-readable storage medium comprising instructions to cause a programmable processor to control a stimulation generator to deliver a series of pulses with alternating pulse polarities from a medical device to a target location of a gastrointestinal (GI) tract of a patient, wherein the series of pulses includes at least a first pulse of a first polarity, a second pulse of a second polarity, a third pulse of the first polarity, and a fourth pulse of the second polarity, wherein the first, second, third and fourth pulses are delivered to the target location in direct succession, in that order, wherein the first pulse and second pulse are separated by a first time delay, the second pulse and third pulse are separated by a second time delay, the third pulse and the fourth pulse are separated by a third time delay, and wherein an increase in a pulse frequency of the series of pulses causes the first time delay, the second time delay, and third time delay to decrease in duration, and a decrease in the pulse frequency of the series of pulses causes the first time delay, the second time delay, and third time delay to increase.

46. The non-transitory computer-readable storage medium of claim 45, wherein the first time delay, second time delay, and third time delay are approximately equal.

47. The non-transitory computer-readable storage medium of claim 45, wherein a fourth time delay follows the fourth pulse.

* * * * *